US012767703B2

(12) United States Patent
Lee et al.

(10) Patent No.: US 12,767,703 B2
(45) Date of Patent: Oct. 20, 2026

(54) ANTIBODY BINDING SPECIFICALLY TO SARS-CoV-2 S PROTEIN OR ANTIGEN-BINDING FRAGMENT THEREOF, BISPECIFIC ANTIBODY, AND USES THEREOF

(71) Applicant: Kookmin University Industry Academy Cooperation Foundation, Seoul (KR)

(72) Inventors: Sukmook Lee, Seoul (KR); Ji Woong Kim, Seoul (KR); Kyun Heo, Seoul (KR); Yeabin Cho, Gyeonggi-do (KR); Hyun jung Kim, Seoul (KR); Hyelim Choi, Gyeonggi-do (KR); Harim Yang, Gyeonggi-do (KR); Ha Gyeong Shin, Seoul (KR); Ji Hyun Lee, Seoul (KR)

(73) Assignee: KOOKMIN UNIVERSITY INDUSTRY ACADEMY COOPERATION FOUNDATION, Seoul (KR)

( * ) Notice: Subject to any disclaimer, the term of this patent is extended or adjusted under 35 U.S.C. 154(b) by 469 days.

(21) Appl. No.: 18/383,595

(22) Filed: Oct. 25, 2023

(65) Prior Publication Data

US 2024/0043508 A1 Feb. 8, 2024

Related U.S. Application Data

(63) Continuation of application No. PCT/KR2022/010843, filed on Jul. 22, 2022, and a continuation of application No. PCT/KR2022/006054, filed on Apr. 27, 2022, and a continuation of application No. PCT/KR2022/006055, filed on Apr. 27, 2022.

(30) Foreign Application Priority Data

Apr. 27, 2021 (KR) ........................ 10-2021-0054590
Apr. 27, 2021 (KR) ........................ 10-2021-0054596
Apr. 27, 2021 (KR) ........................ 10-2021-0054600
Apr. 27, 2021 (KR) ........................ 10-2021-0054603
Apr. 27, 2021 (KR) ........................ 10-2021-0054606
Sep. 6, 2021 (KR) ........................ 10-2021-0118656
Feb. 14, 2022 (KR) ........................ 10-2022-0019199

(51) Int. Cl.

*C07K 16/104* (2026.01)
*A61K 39/00* (2006.01)
*A61P 31/14* (2006.01)
*G01N 33/569* (2006.01)

(52) U.S. Cl.

CPC ............ *C07K 16/104* (2026.01); *A61P 31/14* (2018.01); *G01N 33/56983* (2013.01); *A61K 2039/505* (2013.01); *C07K 2317/31* (2013.01); *G01N 2333/165* (2013.01); *G01N 2469/10* (2013.01)

(58) Field of Classification Search

None

See application file for complete search history.

(56) References Cited

U.S. PATENT DOCUMENTS

| | | | |
|---|---|---|---|
| 10,787,501 | B1 | 9/2020 | Babb et al. |
| 10,975,139 | B1 | 4/2021 | Babb et al. |
| 2021/0088517 | A1 | 3/2021 | Huang et al. |

FOREIGN PATENT DOCUMENTS

| | | | |
|---|---|---|---|
| EP | 3809137 | A1 | 4/2021 |
| KR | 10-2205028 | B1 | 1/2021 |
| KR | 10-2229225 | B1 | 3/2021 |
| KR | 10-2233689 | B1 | 3/2021 |
| KR | 2021-0134300 | A | 11/2021 |
| WO | WO-2021/045836 | A1 | 3/2021 |

OTHER PUBLICATIONS

International Search Report from corresponding PCT Application No. PCT/KR2022/010843, dated Nov. 7, 2022.

https://news.unn.net/news/articleView.html?idxno=233138 (Aug. 5, 2020), University News Network online newspaper article, Kookmin University's Research Team led by Professor Lee, Seok-Muk and Heo, Hyun, selected as a National Project to Develop Dual Antibodies.

International Search Report from corresponding PCT Application No. PCT/KR2022/006055, dated Aug. 10, 2022.

Premkumar, L., et al.; "The receptor-binding domain of the viral spike protein is an immunodominant and highly specific target of antibodies in SARS-CoV-2 patents" Science Immunology, Jun. 11, 2020, vol. 5, article No. eabc8413, inner pp. 1-9.

International Search Report from corresponding PCT Application No. PCT/KR2022/006054, dated Aug. 10, 2022.

Kim, C., et al.; "A therapeutic neutralizing antibody targeting receptor binding domain of SARS-Cov-2 spike protein", Nature Communications, Jan. 12, 2021, vol. 12, thesis No. 288, pp. 1-10.

Notice of Allowance from corresponding Korean Patent Application No. 10-2022-0019199, dated Apr. 25, 2022.

*Primary Examiner* — Oluwatosin A Ogunbiyi

(74) *Attorney, Agent, or Firm* — Harness, Dickey & Pierce, P.L.C.

(57) ABSTRACT

The present invention relates to an anti-SARS-CoV-2 S protein-specific antibody or an antigen-binding fragment thereof, and therapeutic and diagnostic uses thereof. The anti-SARS-CoV-2 S protein-specific antibody or antigen-binding fragment thereof according to the present invention can bind specifically to the S protein, which plays an important role in the infiltration of SARS-CoV-2 into host cells, to inhibit the infection of SARS-CoV-2, and thus can be advantageously used as a therapeutic agent for COVID-19 and as a diagnostic agent and diagnostic kit for COVID-19.

20 Claims, 53 Drawing Sheets

Specification includes a Sequence Listing.

| | Yield (mg/L) |
|---|---|
| RB4 | 90 |
| RB6 | 180 |
| RD3 | 190 |
| RD10 | 245 |
| RG6 | 90 |

FIG. 32

Table 1. Recovery of sandwich ELISA for SARS-CoV-2 RBD.

| Spiked level (ng/mL) | Intra-assay (n=6) | | | Inter-assay (n=6) | | |
|---|---|---|---|---|---|---|
| | Mean ±SD (ng/mL) | Recoveries (%) | CV (%) | Mean ±SD (ng/mL) | Recoveries (%) | CV (%) |
| 5 | 5.28 ± 0.45 | 105.57 | 8.46 | 4.93 ± 0.47 | 98.56 | 9.52 |

A

B

ANTIBODY BINDING SPECIFICALLY TO SARS-CoV-2 S PROTEIN OR ANTIGEN-BINDING FRAGMENT THEREOF, BISPECIFIC ANTIBODY, AND USES THEREOF

CROSS-REFERENCE TO RELATED APPLICATIONS

This application is a continuation of PCT Application No. PCT/KR2022/006054, filed on 27 Apr. 2022, PCT Application No. PCT/KR2022/006055, filed on 27 Apr. 2022 and PCT Application No. PCT/KR2022/010843, filed on 22 Jul. 2022, which claims benefit of Korean Patent Application Nos. 10-2021-0054590, 10-2021-0054596, 10-2021-0054600, 10-2021-0054603, and 10-2021-0054606, filed on 27 Apr. 2021, 10-2022-0019199, filed on 14 Feb. 2022 and 10-2021-0118656, filed on 6 Sep. 2021. The entire disclosures of the applications identified in this paragraph are incorporated herein by references.

SEQUENCE LISTING

This application contains references to amino acid sequences and/or nucleic acid sequences which have been submitted concurrently herewith as the sequence listing XML file entitled "000352uscoa_SequenceListing.XML", file size 72,200 bytes, created on 25 Oct. 2023. The aforementioned sequence listing is hereby incorporated by reference in its entirety pursuant to 37 C.F.R. § 1.52(e)(5).

TECHNICAL FIELD

The present disclosure was carried out under project identifier number 1711120289 and project number NRF-2020M3A9I2107093, supported by the Ministry of Science and ICT of the Republic of Korea. The research management agency for the project is the National Research Foundation of Korea. The name of the research project is "Bio-Medical Technology Development Project", and the title of the research task is "Development of novel bispecific antibodies effectively neutralizing SARS-CoV2 for clinical trials". The institution conducting the research is the Industry-Academic Cooperation Foundation of Kookmin University, and the research period spans from Jul. 1, 2020, to Dec. 31, 2022.

The present disclosure relates to an antibody binding specifically to SARS-CoV-2 S protein or an antigen binding fragment thereof, and a use thereof. More specifically, the present disclosure concerns an anti-SARS-CoV-2 S protein-specific antibody and an antigen binding fragment thereof, and a use thereof for diagnosing or treating SARS-CoV-2 infection.

Also, the present disclosure relates to a diagnostic composition or kit comprising an antibody binding specifically to an RBD of SARS-CoV-2 S protein. More specifically, the present disclosure is concerned with a diagnostic composition comprising an antibody binding specifically to an RBD of SARS-CoV-2 S protein, or a kit suitable for sandwich ELISA using same.

In addition, the present disclosure is concerned with a bispecific antibody binding specifically to SARS-CoV-2.

BACKGROUND ART

The COVID-19 infectious disease caused by the SARS-CoV-2 virus erupted in late December 2019, infecting over 100 million people worldwide and leading to the deaths of over 2 million in just a year. The spike protein (S protein), located on the surface of SARS-CoV-2, binds to the angiotensin-converting enzyme 2 (ACE2) receptor on the surface of host cells, serving as the critical marker inducing infection. Accordingly, the receptor binding region (RBD) of the spike protein is a primary target in the development of therapeutics to counteract infections caused by SARS-CoV-2. Antibody-based treatments are recognized for their efficacy due to their high affinity and specificity towards their targets. Although various vaccines and therapeutic methods have been developed, the rapid emergence of SARS-CoV-2 variants continues to pose a persistent challenge in controlling COVID-19. Therefore, there is an urgent need for the development of new treatments for COVID-19. Moreover, many researchers are exerting significant efforts to develop fast and efficient methods for diagnosing SARS-CoV-2 infections.

DISCLOSURE OF INVENTION

Technical Problem

Leading to the present disclosure, thorough and intensive research conducted by the present inventors with the aim of developing a pharmaceutical composition for prevention or treatment of COVID-19 constructed a novel anti-SARS-CoV-2 S protein-specific antibody or an antigen binding fragment thereof and resulted in the finding that the antibody or the antigen binding fragment has high affinity for S protein.

Accordingly, an aspect of the present disclosure is to provide an antibody binding specifically to SARS-CoV-2 S protein or an antigen binding fragment thereof.

Another aspect of the present disclosure is to provide a pharmaceutical composition comprising the antibody or the antigen binding fragment thereof, and a pharmaceutically acceptable carrier for prevention or treatment of SARS-CoV-2 infectious diseases.

A further aspect of the present disclosure is to provide a composition or kit for detecting SARS-CoV-2; or a composition or kit for diagnosing COVID-19, each comprising the antibody or the antigen binding fragment thereof.

Still another aspect of the present disclosure is to provide a bispecific antibody to SARS-CoV-2.

An additional further aspect of the present disclosure is to provide a pharmaceutical composition comprising a bispecific antibody to SARS-CoV-2 for the treatment of SARS-CoV-2 infections.

Solution to Problem

According to an aspect thereof, the present disclosure provides an antibody binding specifically to SARS-CoV-2 S protein or an antigen binding fragment thereof, selected from the group consisting of (i) an antibody comprising: a heavy chain variable region comprising CDR-H1 of SEQ ID NO: 1, CDR-H2 of SEQ ID NO: 2, and CDR-H3 of SEQ ID NO: 3; and a light chain comprising CDR-L1 of SEQ ID NO: 4, CDR-L2 of SEQ ID NO: 5, and CDR-L3 of SEQ ID NO: 6, or an antigen binding fragment thereof, (ii) an antibody comprising: a heavy chain variable region comprising CDR-H1 of SEQ ID NO: 10, CDR-H2 of SEQ ID NO: 11, and CDR-H3 of SEQ ID NO: 12; and a light chain variable region comprising CDR-L1 of SEQ ID NO: 13, CDR-L2 of SEQ ID NO: 14, and CDR-L3 of SEQ ID NO: 15, or an antigen binding fragment thereof, (iii) an antibody comprising: a heavy chain variable region comprising CDR-H1 of SEQ ID NO: 19, CDR-H2 of SEQ ID NO: 20, and CDR-H3 of SEQ ID NO: 21; and a light chain variable region comprising CDR-L1 of SEQ ID NO: 22, CDR-L2 of SEQ ID NO: 23, and CDR-L3 of SEQ ID NO: 24, or an antigen binding fragment thereof, (iv) an antibody comprising: a heavy chain variable region comprising CDR-H 1 of SEQ ID NO: 28, CDR-H2 of SEQ ID NO: 29, and CDR-H3 of SEQ ID NO: 30; and a light chain variable region comprising CDR-L1 of SEQ ID NO: 31, CDR-L2 of SEQ ID NO: 32, and CDR-L3 of SEQ ID NO: 33, or an antigen binding fragment thereof, and (v) an antibody comprising: a heavy chain variable region comprising CDR-H1 of SEQ ID NO: 37, CDR-H2 of SEQ ID NO: 38, and CDR-H3 of SEQ ID NO: 39; and a light chain variable region comprising CDR-L1 of SEQ ID NO: 40, CDR-L2 of SEQ ID NO: 41, and CDR-L3 of SEQ ID NO: 42, or an antigen binding fragment thereof.

In an embodiment of the present disclosure, the antibodies or the antigen binding fragments thereof selected from (i) to (v) are derived from the clones RG6, RB4, RB6, RD3, and RD10 selected from the working examples of the present disclosure, respectively.

In an embodiment of the present disclosure, the antibody or antigen binding fragment thereof (i) includes the heavy chain variable region of SEQ ID NO: 7 and the light chain variable region of SEQ ID NO: 8; the antibody or antigen binding fragment thereof (ii) includes the heavy chain variable region of SEQ ID NO: 16 and the light chain variable region of SEQ ID NO: 17; the antibody or antigen binding fragment thereof (iii) includes the heavy chain variable region of SEQ ID NO: 25 and the light chain variable region of SEQ ID NO: 26; the antibody or antigen binding fragment thereof (iv) includes the heavy chain variable region of SEQ ID NO: 34 and the light chain variable region of SEQ ID NO: 35; and the antibody or antigen binding fragment thereof (v) includes the heavy chain variable region of SEQ ID NO: 43 and the light chain variable region of SEQ ID NO: 44, but with no limitations thereto.

In an embodiment of the present disclosure, the antibody or antigen binding fragment thereof (i) includes the amino acid sequence of SEQ ID NO: 9, the antibody or antigen binding fragment thereof (ii) includes the amino acid sequence of SEQ ID NO: 18, the antibody or antigen binding fragment thereof (iii) includes the amino acid sequence of SEQ ID NO: 27, the antibody or antigen binding fragment thereof (iv) includes the amino acid sequence of SEQ ID NO: 36, and the antibody or antigen binding fragment thereof (v) includes the amino acid sequence of SEQ ID NO: 45, but with no limitations thereto.

In an embodiment of the present disclosure, the anti-SARS-CoV-2 S protein-specific antibody or the antigen binding fragment thereof according to the present disclosure binds to a receptor binding domain (RBD) of SARS-CoV-2 S protein (spike protein).

In an embodiment of the present disclosure, the RBD of SARS-CoV-2 S protein includes the amino acid sequence of SEQ ID NO: 51.

In an embodiment of the present disclosure, the anti-SARS-CoV-2 S protein-specific antibody or the antigen binding fragment thereof according to the present disclosure inhibits binding of the RBD of SARS-CoV-2 S protein to human ACE2 (angiotensin converting enzyme 2).

In an embodiment of the present disclosure, the anti-SARS-CoV-2 S protein-specific antibody or antigen binding fragment thereof the present invention binds to S1 domain of SARS-CoV-2 S protein.

In an embodiment of the present disclosure, the S1 domain of SARS-CoV-2 S protein includes the amino acid sequence of SEQ ID NO: 52.

In an embodiment of the present disclosure, the S2 domain of SARS-CoV-2 S protein includes the amino acid sequence of SEQ ID NO: 53.

In an embodiment of the present disclosure, the anti-SARS-CoV-2 S protein-specific antibody or antigen binding fragment thereof the present disclosure binds to the full-length spike protein of SARS-CoV-2 S protein.

In an embodiment of the present disclosure, the full-length spike protein of SARS-CoV-2 includes the amino acid sequence of SEQ ID NO: 54.

In an embodiment of the present disclosure, the anti-SARS-CoV-2 S protein-specific antibody or antigen binding fragment thereof the present disclosure binds specifically to a mutant virus having a mutation in SARS-CoV-2 S protein.

In an embodiment of the present disclosure, the anti-SARS-CoV-2 S protein-specific antibody or antigen binding fragment binds specifically to a mutant virus having a mutation in an RBD region of SARS-CoV-2 S protein.

In a further embodiment of the present disclosure, the mutant virus, having a mutation in an RBD region of SARS-CoV-2 S protein, to which the anti-SARS-CoV-2 S protein-specific antibody or antigen binding fragment specifically binds, is a mutant virus that possesses mutation V431A at position 431, F342L at position 342, V367F at position 367, R408I at position 408, A435S at position 435, W436R at position 436, G476S at position 476, V483A at position 483, or N354D/D364Y at positions 354/364 in the RBD region, but with no limitations thereto.

In an embodiment of the present disclosure, the anti-SARS-CoV-2 S protein-specific antibody or the antigen binding fragment thereof binds specifically to a mutant virus having a mutation in a site other than SARS-CoV-2 S protein.

In an embodiment of the present disclosure, the anti-SARS-CoV-2 S protein-specific antibody or the antigen binding fragment thereof binds specifically to the S protein of SARS-CoV.

In some particular embodiments of the present disclosure, the anti-SARS-CoV-2 S protein-specific antibody or antigen binding fragment binds specifically to an RBD region of S protein in SARS-CoV.

In some particular embodiments of the present disclosure, the RBD region of S protein includes the amino acid sequence of SEQ ID NO: 55, but with no limitations thereto.

The antibodies of the present disclosure can be produced using various phage display methods known in the art, as disclosed in [Brinkman et al., 1995, J. Immunol. Methods, 182:41-50]; [Ames et al., 1995, J. Immunol. Methods, 184, 177-186]; [Kettleborough et al. 1994, Eur. J. Immunol, 24, 952-958]; [Persic et al., 1997, Gene, 187, 9-18]; and [Burton et al., 1994, Adv. Immunol., 57, 191-280]; WO 90/02809; WO 91/10737; WO 92/01047; WO 92/18619; WO 93/11236; WO 95/15982; and WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; and 5,969,108.

As used herein, the term "antibody" refers to an antibody specific for SARS-CoV S protein and is intended to encompass an antigen-binding fragment thereof the antibody molecule as well as an intact antibody form.

An intact antibody consists of two full-length light chains and two full-length heavy chain, with disulfide linkages therebetween. Heavy chain constant regions are classified into gamma (γ), mu (μ), alpha (α), delta (δ), and epsilon (ε) types, with the subclassification of the gamma type into gamma 1 (γ1), gamma 2 (γ2), gamma 3 (γ3), and gamma 4 (γ4), and the alpha type into alpha 1 (α1) and alpha 2 (α2). Antibodies can be further classified by kappa (κ) and lambda (λ) types for light chain constant regions (Cellular and Molecular Immunology, Wonsiewicz, M. J., Ed., Chapter 45, pp. 41-50, W. B. Saunders Co. Philadelphia, Pa. (1991); Nisonoff, A., Introduction to Molecular Immunology, 2nd Ed., Chapter 4, pp. 45-65, Sinauer Associates, Inc., Sunderland, Mass. (1984)).

As used herein, the term "antigen-binding fragment" means a fragment retaining the function of binding to an antigen and is intended to encompass Fab, F(ab'), $F(ab')_2$, chemically linked $F(ab')_2$, Fv, and so on. Of the antibody fragments, Fab has one antigen-binding site which takes on the structure composed of light chain and heavy chain variable regions, a light chain constant region, and the first constant region (CH1 region) of the heavy chain. Fab' is different from Fab in that the former has a hinge region containing at least one cysteine residue at the C terminus of the heavy chain CH1 region. An $F(ab')_2$ antibody is produced in such a way that a cysteine residue of the hinge region of Fab' forms disulfide bonding. Fv is a minimum antibody fragment having only a heavy chain variable region and a light chain variable region. A recombination technology for producing an Fv fragment is disclosed in the International Patent Publication filed under the patent cooperation treaty (PCT) WO 88/10649, WO 88/106630, WO 88/07085, WO 88/07086, and WO 88/09344. In case of two-chain Fv, a heavy chain variable region and a light chain variable region are linked to each other by means of non-covalent bonding while single-chain Fv consists of a heavy chain variable region and a single chain variable region which are linked to each other by means of covalent bonding generally via a peptide linker, or directly linked to each other at C-terminus, and thus may form a structure like a dimer, as shown in the two-chain Fv. Such antibody fragments may be obtained by using protease (for example, Fab may be obtained by performing restriction digestion of a whole antibody with papain, while $F(ab')_2$ fragment may be obtained by doing so with pepsin), and may be prepared by means of a gene recombination technology.

The antibody in the present disclosure is particularly in the form of scFv or in an intact form. In addition, the heavy chain constant region may be any one isotype selected from gamma (γ), mu (μ), alpha (α), delta (δ), and epsilon (ε). Preferably, the constant region may be a gamma 1 (IgG1), gamma 2 (IgG2), gamma 3 (IgG3), or gamma 4 (IgG4) isotype, with most preference for gamma 4 (IgG4) isotype. The light chain constant region may be a kappa or lambda isotype, with preference for kappa isotype.

In an embodiment of the present disclosure, the antibody of the present disclosure may be in the form of scFv or IgG4 comprising a kappa light chain or a gamma 4 heavy chain. In another embodiment of the present disclosure, a particular antibody of the present disclosure may be in the form of scFv or IgG1 comprising a kappa light chain and a gamma 1 heavy chain.

The term "heavy chain", as used herein, refers to a full-length heavy chain comprising: a variable region $V_H$, which comprises amino acid sequences having enough variable region sequences to allow the specificity to an antigen; and the three constant regions, $C_H1$, $C_H2$, and $C_H3$, and to any fragment thereof. As used herein, the term "light chain" refers to a full-length light chain comprising: a variable region $V_L$, which comprises amino acid sequences having enough variable region sequences to allow the specificity to an antigen; and a constant region, $C_L$ and to any fragment thereof.

The term "CDR" (complementarity determining region), as used herein, refers to an amino acid sequence in a hypervariable region of an immunoglobulin heavy chain or light chain (Kabat et al., *Sequences of Proteins of Immunological Interest,* 4th Ed., U.S. Department of Health and Human Services, National Institutes of Health (1987)). Three CDRs exist in each of the heavy chain (CDR-H1, CDR-H2, and CDR-H3) and the light chain (CDR-L1, CDR-L2, and CDR-L3). CDRs provide contact residues which play an important role in binding the antibody to an antigen or an epitope.

Herein, the antibody or antigen-binding fragment thereof encompasses not only full-length or intact polyclonal or monoclonal antibodies, but also antigen-binding fragments thereof (e.g., Fab, Fab', $F(ab')_2$, Fab3, Fv, and variants thereof), fusion proteins containing one or more antibody portions, humanized antibodies, chimeric antibodies, minibodies, diabodies, triabodies, tetrabodies, linear antibodies, single-chain antibodies (scFv), scFv-Fc, bispecific antibodies, multi-specific antibodies, and any other modified configuration of the immunoglobulin molecule that contains an antigen recognition site of the required specificity, comprising glycosylated variants of antibodies, amino acid sequence variants of antibodies, and covalently modified antibodies. Concrete examples of the modified antibodies and antigen-binding fragments thereof include nanobodies, AlbudAbs, DARTs(dual affinity re-targeting), BiTEs(bispecific T-cell engager), TandAbs(tandem diabodies), DAFs(dual acting Fab), two-in-one antibodies, SMIPs(small modular immunopharmaceuticals), FynomAbs(fynomers fused to antibodies), DVD-Igs(dual variable region immunoglobulin), CovX-bodies(peptide modified antibodies), duobodies, and triomAbs, but with no limitations to the listing of such antibodies and antigen-binding fragments thereof.

The term "framework" or "FR", as used herein, refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL/Vk):

(a) FRH1 (Framework region 1 of Heavy chain)-CDRH1 (complementarity determining region 1 of Heavy chain)-FRH2-CDRH2-FRH3-CDRH3-FRH4; and (b) FRL1 (Framework region 1 of Light chain)-CDRL1 (complementarity determining region 1 of Light chain)-FRL2-CDRL2-FRL3-CDRL3-FRL4.

The term "variable region" or "variable domain" refers to the domain of an antibody heavy or light chain responsible for binding the antibody to antigen. The variable domains of the heavy chain and light chain (VH and VL, respectively) of a native antibody generally have similar structures, with each domain comprising four conserved framework regions (FRs) and three hypervariable regions (HVRs). (Kindt et al. Kuby Immunology, $6^{th}$ ed., W.H. Freeman and Co., page 91 (2007)). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively.

The term "specifically binds" or similar expressions mean that an antibody or an antigen-binding fragment thereof, or another construct such as an scFv, forms a complex with an antigen that is relatively stable under physiologic conditions. Specific binding can be characterized by an equilibrium dissociation constant of at least about $1\times10^{-6}$ M or less (e.g., $9\times10^{-7}$ M, $8\times10^{-7}$ M, $7\times10^{-7}$ M, $6\times10^{-7}$ M, $5\times10^{-7}$ M, $4\times10^{-7}$ M, $3\times10^{-7}$ M, $2\times10^{-7}$ M, or $1\times10^{-7}$ M), preferably $1\times10^{-7}$ M or less (e.g., $9\times10^{-8}$ M, $8\times10^{-8}$ M, $7\times10^{-8}$ M, $6\times10^{-8}$ M, $5\times10^{-8}$ M, $4\times10^{-8}$ M, $3\times10^{-8}$ M, $2\times10^{-8}$ M, or $1\times10^{-8}$ M), and more preferably $1\times10^{-8}$ M or less (e.g., $9\times10^{-9}$ M, $8\times10^{-9}$ M, $7\times10^{-9}$ M, $6\times10^{-9}$ M, $5\times10^{-9}$ M, $4\times10^{-9}$ M, $3\times10^{-9}$ M, $2\times10^{-9}$ M, or $1\times10^{-9}$ M) (a smaller $K_D$ denotes a tighter binding). Methods for determining whether two molecules specifically bind are well known in the art and include, for example, equilibrium dialysis, surface plasmon resonance, and the like.

As used herein, the term "affinity" refers to total strength of noncovalent interactions between a single binding site of a molecule (e.g., an antibody) and its binding partner (e.g., an antigen). Unless specified otherwise, "binding affinity", as used herein, refers to intrinsic binding affinity which reflects a 1:1 interaction between members of a binding pair (e.g., antibody and antigen). The affinity of a molecule X for its partner Y can generally be represented by the equilibrium dissociation constant ($K_D$). Affinity can be measured by common methods known in the art, comprising those disclosed herein.

As used herein, the term "human antibody" refers to an antibody which possesses an amino acid sequence which corresponds to that of an antibody produced by a human or a human cell or derived from a non-human source that utilizes human antibody repertoires or other human antibody-encoding sequences. This definition for a human antibody specifically excludes a humanized antibody, which includes non-human antigen-binding residues.

The term "chimeric" antibody, as used herein, refers to an antibody in which a portion of the heavy and/or light chain is derived from a particular source or species, while the remainder of the heavy and/or light chain is derived from a different source or species.

As used herein, the term "humanized antibody" refers to a chimeric immunoglobulin which includes the minimal sequence derived from non-human immunoglobulin of non-human (e.g., mouse) antibodies, an immunoglobulin chain or fragment thereof (e.g., Fv, Fab, Fab', $F(ab')_2$, or other antigen-binding subsequences of the antibody). In most cases, humanized antibodies are human immunoglobulins (recipient antibodies) in which residues from a complementarity-determining region (CDR) of the recipient are replaced by residues from a CDR of a non-human species (donor antibody), such as mouse, rat or rabbit having desired specificity, affinity, and capacity. In some instances, Fv framework region (FR) residues of the human immunoglobulin are replaced by corresponding non-human residues. In addition, humanized antibodies may include residues which are found neither in the recipient antibody nor in the imported CDR or framework sequences. These modifications are made to further improve and optimize antibody performance. In general, the humanized antibody will include substantially all of at least one, and typically two, variable domains, in which all or substantially all of the CDR regions correspond to CDR regions of a non-human immunoglobulin and all or substantially all of the FR regions have sequences of FR regions of a human immunoglobulin sequence. The humanized antibody includes at least a portion of an immunoglobulin constant region (Fc region), typically a constant region (Fc region) of a human immunoglobulin.

The term "substantial identity" or "substantially identical," as used herein in the context of the variants, indicates that two peptide sequences, when optimally aligned, such as by the programs GAP or BESTFIT using default gap weights, share at least about 90% sequence identity and more preferably about 95%, 98%, or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution.

Such amino acid variations may be provided on the basis of a relative similarity of amino acid side chains, e.g., hydrophobicity, hydrophilicity, charge, and size. By the analysis for size, shape, and type of the amino acid side chains, it is clear that all of arginine, lysine, and histidine residues are those having positive charge; alanine, glycine, and serine have a similar size; phenylalanine, tryptophan, and tyrosine have a similar shape. Accordingly, based on these considerable factors, arginine, lysine and histidine; alanine, glycine and serine; and phenylalanine, tryptophan, and tyrosine may be considered to be functional equivalents biologically.

In the introduction of variations, the hydropathic index of amino acids may be considered. Each amino acid has been assigned a hydropathic index on the basis of hydrophobicity and charge characteristics thereof: isoleucine (+4.5); valine (+4.2): leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5): aspartate (−3.5); asparagine (−3.5); lysine (−3.9); and arginine (−4.5).

The hydrophobic amino acid indexes are very important in assigning interactive biological functions of proteins. It is known in the art that certain amino acids may be substituted by other amino acids having a similar hydropathic index and still result in similar biological activity. In cases where a variation is introduced with reference to the hydrophobic indexes, the substitution is made between amino acids having a difference in the hydrophobic index within preferably ±2, more preferably ±1, and still more preferably ±0.5.

Meanwhile, it is also well known that substitutions between amino acids having similar hydrophilicity values result in proteins with equivalent biological activity. As disclosed in U.S. Pat. No. 4,554,101, each amino acid residue has been assigned the following hydrophilicity values: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In cases where variations are introduced with reference to the hydrophilicity values, substitutions may be made between amino acids that exhibit a hydrophilicity value difference of preferably within ±2, more preferably within ±1, and even more preferably within ±0.5.

Amino acid exchanges in proteins which do not entirely alter activity of a molecule are known in the art (H. Neurath, R. L. Hill, The Proteins, Academic Press, New York, 1979). The most common occurring exchanges are exchanges between amino acid residues Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly.

In an embodiment of the present disclosure, the antibody or the antigen binding fragment thereof according to the present disclosure, which binds specifically to SARS-CoV-2 S protein, are expressed as RG6, RB4, RB6, RD3, or RD10.

In an embodiment of the present disclosure, the antibody or antigen binding fragment has an equilibrium dissociation constant $K_D$ of $7.2\times10^{-10}$ M or less for the RBD of the S protein.

In another embodiment of the present disclosure, the antibody or antigen binding fragment has an equilibrium dissociation constant $K_D$ of $3.2\times10^{-9}$ M for the S1 antigen of the S protein.

In an embodiment of the present disclosure, RG6, RB4, RB6, RD3, and RD10, which are the antibody or the antigen binding fragment thereof binding specifically to SARS-CoV-2 S protein, binds specifically to RBD of S protein in SARS-CoV as well as to the RBD antigen of S protein in SARS-CoV-2.

The anti-SARS-CoV-2 S protein-specific antibody or the antigen binding fragment thereof according to the present disclosure may include a little change in the amino acid sequence, i.e., a modification that has little effect on the tertiary structure and function of the antibody. Therefore, although not identical to the aforementioned sequence, an anti-SARS-CoV-2 S protein-specific antibody or an antigen binding fragment thereof in accordance with some embodiments may at least 100%, 93%, 95%, 96%, 97%, or 98% similarity.

In an embodiment of the present disclosure, the anti-SARS-CoV-2 S antibody or the antigen binding fragment thereof according to the present disclosure includes, but are not limited to, monoclonal antibodies, bispecific antibodies, multispecific antibodies, human antibodies, humanized antibodies, chimeric antibodies, single-chain Fvs (scFv), single-chain antibodies, Fab fragments, F(ab') fragments, disulfide-linked Fvs (sdFv), anti-idiotypic (anti-Id) antibodies, and epitope-binding fragments of the antibodies, each comprising a heavy chain variable region and light chain variable region comprising CDRs of the sequences described above. In another embodiment of the present disclosure, the anti-SARS-CoV-2 S protein-specific antibody or the antigen binding fragment thereof is an anti-SARS-CoV-2 S protein scFv.

In a concrete embodiment of the present disclosure, the heavy chain variable region and light chain variable region included in the antibody or the antigen binding fragment thereof are linked to each other via a linker such as $(Gly\text{-}Ser)_n$, $(Gly_2\text{-}Ser)_n$, $(Gly_3\text{-}Ser)_n$, or $(Gly_4\text{-}Ser)_n$. Here, n is an integer of 1 to 6 and specifically 3 or 4, but with no limitations thereto. The light chain variable region and heavy chain variable region in scFv may be arranged as follows: light chain variable region-linker-heavy chain variable region or heavy chain variable region-linker-light chain variable region.

Another aspect of the present disclosure provides a nucleic acid molecule encoding the anti-SARS-CoV-2 S protein-specific antibody or the antigen binding fragment thereof.

As used herein, the term "nucleic acid molecule" is intended to comprehensively encompass RNA molecules as well as DNA (gDNA and cDNA), and nucleotides, which account for a basic unit of nucleic acid molecules, include not only natural nucleotides, but also analogues having modified sugar or base moieties (Scheit, *Nucleotide Analogs*, John Wiley, New York (1980); Uhlman and Peyman, *Chemical Reviews,* 90:543-584(1990)).

It would be obvious to a person skilled in the art that the nucleotide sequence encoding the antibody or the antigen binding fragment thereof according to the present disclosure is any nucleotide coding for the amino acid sequence constituting the antibody or the antigen binding fragment thereof and is not limited to any particular nucleotide sequence.

The reason is that even if the nucleotide sequence undergoes mutation, the expression of the mutated nucleotide sequence into a protein may not cause a change in the protein sequence. This is called the degeneracy of codons. Therefore, the nucleotide sequence includes nucleotide sequences containing functionally equivalent codons, codons encoding the same amino acids (e.g., due to the degeneracy of codons, the number of codons for arginine or serine being six), or codons containing biologically equivalent amino acids.

Considering biologically equivalent variations described in the foregoing, the nucleic acid molecule coding for the amino acid sequence accounting for the antibody or antigen-binding fragment thereof the present disclosure is construed to encompass sequences having substantial identity to them. Sequences having the substantial identity show at least 60% (e.g., 61%, 62%, 63%, 64%, 65%, 66%, 67%, 68%, or 69%), particularly at least 70% (e.g., 71%, 72%, 73%, 74%, 75%, 76%, 77%, 78%, or 79%), more particularly 80% (e.g., 81%, 82%, 83%, 84%, 85%, 86%, 87%, 88%, or 89%), even more particularly at least 90% (e.g., 91%, 92%, 93%, 94%, 95%, 96%, 97%, 98%, or 99%), most particularly at least 95% (e.g., 95%, 96%, 97%, 98%, or 99%) similarity to the nucleic acid molecule of this disclosure, as measured by using one of the sequence comparison algorithms for the sequences of the present disclosure aligned to any sequence, with maximum correspondence therebetween. With respect to % similarity, all integers from 60% to 100% and minor numbers existing therebetween fall within the scope of the present disclosure.

Methods of alignment of sequences for comparison are well-known in the art. Various programs and alignment algorithms are disclosed in: Smith and Waterman, *Adv. Appl. Math.* 2:482(1981); Needleman and Wunsch, *J. Mol. Bio.* 48: 443(1970); Pearson and Lipman, *Methods in Mol. Biol.* 24:307-31(1988); Higgins and Sharp, *Gene* 73:237-44 (1988); Higgins and Sharp, *CABIOS* 5:151-3(1989); Corpet et al., *Nuc. Acids Res.* 16:10881-90(1988); Huang et al., *Comp. Appl. BioSci.* 8:155-65(1992) and Pearson et al., *Meth. Mol. Biol.* 24:307-31(1994). The NCBI Basic Local Alignment Search Tool (BLAST) (Altschul et al., *J. Mol. Biol.* 215:403-10 (1990)) is accessible from the NBCI (National Center for Biotechnology Information) and on the Internet and may be used in connection with sequence analysis programs such as blastp, blastn, blastx, tblastn and tblastx. BLAST may be accessed through the BLAST webpage of the NCBI's website. The method for comparing sequence homology using such a program is available from the BLAST help page of the NCBI's website.

According to some particular embodiments of the present disclosure, polypeptides of the antibodies to SARS-CoV-2 S protein or antigen binding fragments thereof, e.g., polypeptides of heavy and light chains, e.g., heavy chain CDRs, light chain CDRs, heavy chain variable regions, light chain variable regions, etc., and nucleotide sequences coding therefor are given in the annexed sequence listings.

Provided according to another aspect of the present disclosure is a recombinant vector carrying the nucleic acid molecule coding for the anti-SARS-CoV-2 S protein-specific antibody or antigen binding fragment.

As used herein, the term "vector" refers to a means for expressing a target gene in a host cell and is intended to encompass a variety of vectors comprising: plasmid vectors; cosmid vectors; and viral vectors such as bacteriophage vectors, adenovirus vectors, retrovirus vectors, and adeno-associated virus vectors.

According to an embodiment of the present disclosure, the nucleic acid molecule coding for the heavy chain variable region and the nucleic acid molecule coding for the heavy chain variable region are operatively linked to a promoter in the vector of the present disclosure.

As used herein, "operatively linked" means that an expression control sequence (e.g., a promoter, a signal sequence, or an array of transcriptional regulatory factors) and a nucleic acid of interest are linked so that the transcription and/or translation of the nucleic acid of interest can be governed by the control sequence.

The recombinant vector system of the present disclosure can be constructed by various methods known in the art. For concrete methods, reference may be made to Sambrook et al., Molecular Cloning, A Laboratory Manual, Cold Spring Harbor Laboratory Press (2001), which is incorporated in its entirety herein by reference.

The vector of the present disclosure may be typically constructed as a vector for cloning or expression. In addition, the vector of the present disclosure may be constructed with a prokaryotic cell or an eukaryotic cell serving as a host.

For example, when the vector of the present disclosure is an expression vector, with a eukaryotic cell serving as a host, advantage is taken of a promoter derived from the genome of a mammalian cell (e.g., metallothionein promoter, beta-actin promoter, human hemoglobin promoter, and human muscle creatine promoter) or a promoter derived from mammalian viruses (e.g., adenovirus late promoter, vaccinia virus 7.5K promoter, SV40 promoter, cytomegalovirus promoter, tk promoter of HSV, mouse mammary tumor virus (MMTV) promoter, LTR promoter of HIV, promoter of Moloney virus, promoter of Epstein-Barr virus (EBV), and promoter of Rous sarcoma virus (RSV)), with a polyadenylated sequence commonly employed as a transcription termination sequence in the vector.

The vector of the present disclosure may be fused with the other sequences to facilitate the purification of the antibody expressed therefrom. Examples of the fusion sequence include glutathione 5-transferase (Pharmacia, USA), maltose binding protein (NEB, USA), FLAG (IBI, USA), and 6× His (hexahistidine; Qiagen, USA).

Since the protein expressed by the vector of the present disclosure is an antibody, the expressed antibodies can be easily purified through protein A column or the like even without additional sequences for purification.

Meanwhile, the expression vector of the present disclosure includes, as a selective marker, an antibiotic agent-resistant gene that is ordinarily used in the art, examples of which include resistant genes against ampicillin, gentamycin, carbenicillin, chloramphenicol, streptomycin, kanamycin, geneticin, neomycin, and tetracycline.

Optionally, the vector may additionally carry a gene encoding a reporter molecule (e.g., luciferase and glucuronidase).

According to an embodiment of the present disclosure, the expression vector is a recombinant vector for host cell expression, into which a nucleotide sequence encoding the anti-SARS-CoV-2 S antibody or antigen binding fragment thereof is inserted, wherein the vector carries: a promoter, which is operatively linked to the nucleotide sequence and forms an RNA molecule in host cells; and a poly A signal sequence, which acts on the host cells to cause polyadenylation of the 3'-terminus of the RNA molecule.

According to another aspect thereof, the present disclosure provides an isolated host cell transformed with the recombinant vector.

So long as it is capable of performing continuous cloning and expression while stabilizing the vector of the present disclosure, any host cell known in the art may be used and, for instance, examples of eukaryotic host cells suitable for the vector include monkey kidney cells 7 (COS7), NSO cells, SP2/0, Chinese hamster ovary (CHO) cells, W138, baby hamster kidney (BHK) cells, MDCK, myeloma cell lines, HuT 78 cells, and HEK-293, but are not limited thereto.

As used herein, the term "transformed", "transduced", or "transfected" refers to pertaining to the delivery or introduction of a foreign nucleic acid into a host cell. The "transformed", "transduced", or "transfected" cells are cells into which a foreign nucleic acid is transformed, transduced, or transfected. Within the scope of the transformed, transduced, or transfected cells, the cells themselves and progeny cells thereof obtained through passages fall.

When host cells are eukaryotic cells, the vector may be injected into the host cells by microinjection (Capecchi, M. R., Cell, 22:479(1980)), calcium phosphate precipitation (Graham, F. L. et al., Virology, 52:456(1973)), electroporation (Neumann, E. et al., EMBO J., 1:841(1982)), liposome-mediated transfection (Wong, T. K. et al., Gene, 10:87 (1980)), DEAE-dextran treatment (Gopal, Mol. Cell Biol., 5:1188-1190(1985)), gene bombardment (Yang et al., Proc. Natl. Acad. Sci., 87:9568-9572(1990)), and the like.

Herein, the recombinant vector injected into the host cells can express the recombined polypeptide or polypeptide complex in the host cells, and in such a case, a large amount of polypeptides or polypeptide complexes are obtained. For example, when the vector contains a lac promoter, gene expression can be induced by treatment of host cells with IPTG.

The culturing is usually carried out under aerobic conditions by, for example, a shaking culture or a rotation by a rotator. The culturing temperature is preferably in a range of 10-40° C., and the culturing time is generally for 5 hours to 7 days. The pH of the medium is preferably maintained at 3.0-9.0 during culturing. The pH of the medium can be adjusted with an inorganic or organic acid, an alkali solution, urea, calcium carbonate, ammonia, or the like. For maintenance and expression of recombinant vectors, if necessary, antibiotics, such as ampicillin, streptomycin, chloramphenicol, kanamycin, and tetracycline, may be added during culturing. When host cells transformed by a recombinant expression vector having an inducible promoter is cultured, an inducer suitable for a medium may be added if necessary. For example, isopropyl-β-D-thiogalactopyranoside (IPTG)

may be added when the expression vector contains a lac promoter, and indoleacrylic acid may be added when the expression vector contains a trp promoter.

Provided according to another aspect of the present disclosure is a polypeptide complex in which i) the anti-SARS-CoV-2 S protein-specific antibody or the antigen binding fragment thereof and ii) and an additional polypeptide are linked to each other.

The ii) additional polypeptide is the aforementioned antibody or antigen binding fragment, or a "target binding polypeptide" or a "polypeptide of target" rather than an antibody or an antigen binding fragment.

The antibody or antigen binding fragment or the target binding polypeptide or the polypeptide of target as ii) the additional polypeptide may bind to the same antigen as for i) the anti-SARS-CoV-2 S protein-specific antibody or the antigen binding fragment thereof or to a different antigen from that therefor. When i) the anti-SARS-CoV-2 S protein-specific antibody or the antigen binding fragment thereof targets the same antigen as for ii) the additional polypeptide, the antigen preferably has different epitopes.

As used herein, the term "target-binding polypeptide" refers to a non-immunoglobulin polypeptide molecule which exhibits binding affinity for a target antigen or a hapten, like an antibody, but is structurally relevant to an antibody. The target-binding polypeptides, also called antibody-like molecules or antibody mimetics, generally have a molecular weight of 3-20 kDa, unlike antibodies, which have a molecular weight of about 150 kDa. Examples of the target-binding polypeptide include, but are not limited to, an affibody derived from Z-domain of protein A, an affilin derived from gamma-B crystallin or ubiquitin, affimer derived from cystatin, an affitin derived from Sac7d of *Sulfolobus acidocaldarius*, an alphabody derived from triple helix coiled coil, an anticalin derived from lipocalin, an avimer derived from a cell membrane receptor domain, DARPin derived from an ankyrin repeat motif, Fynomer derived from the SH3 domain of Fyn, a Kunits domain peptide derived from the Kunits domain of protease inhibitor, a monobody derived from the $10^{th}$ type III domain of fibronectin, and nanoCLAMP derived from carbohydrate binding module 32-2 of NagH in *Clostridium perfringens*. Through various screening methods known in the art, such as phage display, ribosome display, etc., the target-binding polypeptide may be engineered to have binding affinity for any target antigen or hapten.

In an embodiment of the present disclosure, the target binding polypeptide may be a polypeptide derived from a host cell toward which SARS-CoV-2, the target of the present disclosure, is directed. By way of example, when the target binding polypeptide is an ACE2 receptor in a host cell, the ACE receptor linked to the anti-SARS-CoV-2 S protein-specific antibody or the antigen binding fragment thereof is associated with SARS-CoV-2, followed by the neutralization of the SARS-CoV-2, with the consequent prevention of SARS-CoV-2 from entry into host cells.

As used herein, the term "polypeptide of target" refers to a polypeptide derived from SARS-CoV-2, the target of the present disclosure, which binds to a different polypeptide as a constituent of SARS-CoV-2. The polypeptide of target is associated with a different polypeptide that is a constituent of SARS-CoV-2, thereby preventing the entry of SARS-CoV-2 into host cells. The polypeptide of target may be a polypeptide that SARS-CoV-2 employs in invading host cells and may be specifically a polypeptide as a constituent of the spike protein, but with no limitations thereto.

The polypeptide complex according to an aspect of the present disclosure has a multimeric form in which individual antibodies or antigen binding fragments and monomers of the polypeptide are linked to each other. The polypeptide complexes of the present invention are linked to each other via a covalent linkage. According to an embodiment of the present disclosure, the polypeptide complex may be implemented in the form of a fused protein or a conjugate.

According to an embodiment of the present invention, the polypeptide complex may be implemented in the form of a fused protein or a conjugate. Therefore, the antibody or the antigen binding fragment thereof may be linked by means of chemical conjugation (using known organic chemistry methods) or by any other means (for example, via the expression of the complex as a fusion protein, or either directly, or indirectly via a linker (e.g., an amino acid linker)).

According to some particular embodiments of the present disclosure, individual polypeptides constituting the polypeptide complex are connected via at least one linker. The linker may be composed of the amino acid sequence represented by the general formula (GnSm)p or (SmGn)p:

wherein n, m, and p are each independently an integer, n is an integer of 1 to 7;

m is an integer of 0 to 7;

with the sum of n and m being an integer of 8 or less; and p is an integer of 1 to 7.

In another particular embodiment of the present disclosure, the linker is (GnSm)p or (SmGn)p wherein n=1 to 5 or m=0 to 5. In a more particular embodiment, n=4 and m=1. In a further more particular embodiment, the linker is $(GGGGS)_3$. In another embodiment, the linker is GGGGS. In a further embodiment, the linker is VDGS. In a still further embodiment, the linker is ASGS.

In an embodiment of the present disclosure, the polypeptide complex may be a multispecific complex directing toward two or more targets.

In some particular embodiments of the present disclosure, the polypeptide complex of the present disclosure may include two or more antibodies or antigen binding fragments thereof selected from the following (i) to (v), but with no limitations thereto:

(i) an antibody binding specifically to SARS-CoV-2 S protein or an antigen binding fragment thereof, the antibody comprising: a heavy chain variable region comprising CDR-H1 of SEQ ID NO: 1, CDR-H2 of SEQ ID NO: 2, and CDR-H3 of SEQ ID NO: 3; and a light chain variable region comprising CDR-L1 of SEQ ID NO: 4, CDR-L2 of SEQ ID NO: 5, and CDR-L3 of SEQ ID NO: 6;

(ii) an antibody binding specifically to SARS-CoV-2 S protein or an antigen binding fragment thereof, the antibody comprising: a heavy chain variable region comprising CDR-H1 of SEQ ID NO: 10, CDR-H2 of SEQ ID NO: 11, and CDR-H3 of SEQ ID NO: 12; and a light chain variable region comprising CDR-L1 of SEQ ID NO: 13, CDR-L2 of SEQ ID NO: 14, and CDR-L3 of SEQ ID NO: 15;

(iii) an antibody binding specifically to SARS-CoV-2 S protein or an antigen binding fragment thereof, the antibody comprising: a heavy chain variable region comprising CDR-H1 of SEQ ID NO: 19, CDR-H2 of SEQ ID NO: 20, and CDR-H3 of SEQ ID NO: 21; and a light chain variable region comprising CDR-L1 of SEQ ID NO: 22, CDR-L2 of SEQ ID NO: 23, and CDR-L3 of SEQ ID NO: 24;

(iv) an antibody binding specifically to SARS-CoV-2 S protein or an antigen binding fragment thereof, the antibody comprising: a heavy chain variable region comprising CDR-H1 of SEQ ID NO: 28, CDR-H2 of SEQ ID NO: 29, and CDR-H3 of SEQ ID NO: 30; and a light chain variable region comprising CDR-L1 of SEQ ID NO: 31, CDR-L2 of SEQ ID NO: 32, and CDR-L3 of SEQ ID NO: 33; and (v) an antibody binding specifically to SARS-CoV-2 S protein or an antigen binding fragment thereof, the antibody comprising: a heavy chain variable region comprising CDR-H1 of SEQ ID NO: 37, CDR-H2 of SEQ ID NO: 38, and CDR-H3 of SEQ ID NO: 39; and a light chain variable region comprising CDR-L1 of SEQ ID NO: 40, CDR-L2 of SEQ ID NO: 41, and CDR-L3 of SEQ ID NO: 42.

In some particular embodiments of the present disclosure, the polypeptide complex comprising at least two antibodies or antigen binding fragments thereof selected from the group consisting of (i) to (v) set forth above may be expressed into a fusion protein as the at least two antibodies or antigen binding fragments selected from (i) to (v) are linked to each other via an amino acid linker or may be prepared by chemical conjugation into a conjugate.

Another aspect of the present disclosure provides a nucleic acid molecule encoding the polypeptide complex. The common contents between the nucleic acid according to an aspect of the present disclosure and the anti-SARS-CoV-2 S protein-specific antibody or antigen binding fragment thereof according to an aspect of the present disclosure are omitted in order to avoid undue redundancy leading to the complexity of the description.

Another aspect of the present disclosure provides a pharmaceutical composition for prevention or treatment of SARS-CoV-2 infectious diseases, the composition comprising the antibody binding specifically to SARS-CoV-2 S protein or an antigen binding fragment thereof, and a pharmaceutically acceptable carrier.

In an embodiment of the present disclosure, the SARS-CoV-2 causing SARS-CoV-2 infectious diseases is a mutant virus having a mutation in the S protein thereof.

In some particular embodiments of the present disclosure, the mutant virus has a mutation in an RBD region of the S protein.

In some more particular embodiments of the present disclosure, the mutant virus having a mutation in the RBD region of S protein may include the mutation V431A at position 431, F342L at position 342, V367F at position 367, R408I at position 408, A435S at position 435, W436R at position 436, G476S at position 476, V483A at position 483, or N354D/D364Y at positions 354 and 364 in the RBD region of S protein, but with no limitations thereto.

In some particular embodiments of the present disclosure, the monoclonal antibody of the present disclosure has the efficacy of reducing clinical severity for SARS-CoV-2 virus.

As will be elucidated, the monoclonal antibody of the present disclosure exhibits higher efficacy of reducing clinical severity of SARS-CoV-2 infectious diseases when being in the form of IgG4 than IgG1.

Also, another aspect of the present disclosure provides a pharmaceutical composition comprising the antibody binding specifically to SARS-CoV-2 S protein or the antigen binding fragment thereof for prevention or treatment of SARS-CoV infectious disease. The antibody binding specifically to SARS-CoV-2 S protein or the antigen binding fragment thereof according to the present disclosure binds specifically to the S protein of SARS-CoV as well as that of SARS-CoV-2 and thus can be advantageously used for preventing or treating SARS-CoV infectious diseases.

The pharmaceutical composition of the present disclosure employs the anti-SARS-CoV-2 S protein-specific antibody or antigen binding fragment thereof according to the present disclosure, and the common contents therebetween are omitted in order to avoid undue complexity of the description.

So long as it is typically used for formulation, any pharmaceutically acceptable carrier may be contained in the pharmaceutical composition of the present disclosure. Examples of the pharmaceutically acceptable carrier include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil, but are not limited thereto. The pharmaceutical composition of the present disclosure may further include a lubricant, a wetting agent, a sweetener, a flavorant, an emulsifier, a suspending agent, a preservative, and the like in addition to the above ingredients. With regard to suitable pharmaceutically acceptable carriers and preparations, reference may be made to Remington's Pharmaceutical Sciences ($19^{th}$ ed., 1995).

The pharmaceutical composition of the present disclosure may be administered orally or parenterally, for example, by intravenous injection, subcutaneous injection, intramuscular injection, intraperitoneal injection, intrasternal injection, topical administration, intranasal administration, intrapulmonary administration, and rectal administration.

Appropriate doses of the pharmaceutical composition of the present invention vary depending on various factors comprising a formulating method, a manner of administration, patient's age, body weight, sex, and morbidity, food, a time of administration, a route of administration, an excretion rate, and response sensitivity. An ordinarily skilled practitioner can easily determine and prescribe an effective dose for desired treatment or prevention. According to a preferable embodiment of the present disclosure, the daily dose of the pharmaceutical composition of the present disclosure is 0.0001-100 mg/kg. As used herein, the term "pharmaceutically effective amount" refers to an amount sufficient to prevent or treat the above-described diseases.

As used herein, the term "prevention" refers to a prophylactic or protective treatment of a disease or a disease condition. As used herein, the term "treatment" refers to a reduction, suppression, amelioration, or eradication of a disease condition.

The pharmaceutical composition of the present disclosure may be formulated into a unit dosage form or may be introduced into a multi-dose container by using a pharmaceutically acceptable carrier and/or excipient according to a method that can be easily implemented by a person having an ordinary skill in the art to which the present invention belongs. Here, the formulation may be in the form of a solution in an oily or aqueous medium, a suspension, an emulsion, an extract, a pulvis, a suppository, a powder, granules, a tablet, or a capsule, and may further contain a dispersant or a stabilizer.

According to an aspect thereof, the present disclosure provides a pharmaceutical composition for prevention or treatment of SARS-CoV-2 infectious diseases, the composition comprising: a polypeptide complex in which i) the anti-SARS-CoV-2 S protein-specific antibody or the antigen binding fragment thereof and ii) an additional polypeptide are linked to each other; and a pharmaceutically acceptable carrier.

In an embodiment of the present disclosure, the additional polypeptide may be an anti-SARS-CoV-2 antibody or an antigen binding fragment thereof, or a target-binding, non-antibody polypeptide specifically binding to SARS-CoV-2.

The anti-SASRS-CoV-2 antibody or the antigen binding fragment thereof may be the aforementioned antibody or antigen binding fragment thereof according to the present disclosure.

Therefore, the polypeptide complex may include two or more of the aforementioned antibodies or antigen binding fragments thereof according to present disclosure, but is not limited thereto.

Since the pharmaceutical composition of the present disclosure employs the polypeptide complex of the present disclosure as an active ingredient, common contents therebetween are omitted to avoid undue complexity of the description.

According to another aspect thereof, the present disclosure provides a composition for detecting SARS-CoV-2 viruses or a composition for diagnosing SARS-CoV- 2 infectious diseases (COVID-19), each comprising the antibody binding specifically to SARS-CoV-2 S protein or the antigen binding fragment thereof.

According to a further aspect thereof, the present disclosure provides a composition for detecting SARS-CoV-2 viruses or a composition for diagnosing SARS-CoV-2 infectious diseases (COVID-19), each comprising the antibody binding specifically to SARS-CoV-2 S protein or the antigen binding fragment thereof. Specifically binding to the S protein of SARS-CoV as well as SARS CoV-2, the antibody binding specifically to SARS-CoV-2 S protein or the antigen binding fragment thereof can also be advantageously used for preventing or treating SARS-CoV infectious diseases.

In an embodiment thereof, the present disclosure provides a composition for diagnosis of SARS-CoV-2 infection (COVID-19) or for detection of a SARS-CoV-2 antigen, the composition comprising a pair of the following antibodies or antigen binding fragments thereof, each antibody or fragment binding specifically to a receptor binding domain (RBD) of SARS-CoV-2 S protein:

(i) HCDR1 comprising the amino acid sequence of SEQ ID NO: 28, HCDR2 comprising the amino acid sequence of SEQ ID NO: 29, HCDR3 comprising the amino acid sequence of SEQ ID NO: 30, LCDR1 comprising the amino acid sequence of SEQ ID NO: 31, LCDR2 comprising the amino acid sequence of SEQ ID NO: 32, and LCDR3 comprising the amino acid sequence of SEQ ID NO: 33, or antigen binding fragments thereof; and (ii) HCDR1 comprising the amino acid sequence of SEQ ID NO: 19, HCDR2 comprising the amino acid sequence of SEQ ID NO: 20, HCDR3 comprising the amino acid sequence of SEQ ID NO: 21, LCDR1 comprising the amino acid sequence of SEQ ID NO: 22, LCDR2 comprising the amino acid sequence of SEQ ID NO: 23, and LCDR3 comprising the amino acid sequence of SEQ ID NO: 24, or antigen binding fragments thereof.

Provided according to an embodiment of the present disclosure is the composition for diagnosis of SARS-CoV-2 infection (COVID-19) or for detection of a SARS-CoV-2 antigen, wherein the antibody or the antigen binding fragment of (i) includes a heavy chain variable region (VH) comprising the amino acid sequence of SEQ ID NO: 34 and a light chain variable region (VL) comprising the amino acid sequence of SEQ ID NO: 35, and the antibody or the antigen binding fragment of (ii) includes a heavy chain variable region comprising the amino acid sequence of SEQ ID NO: 25 and a light chain variable region comprising the amino acid sequence of SEQ ID NO: 26.

In an embodiment of the present disclosure, the pair of antibodies or antigen binding fragments thereof in the composition is derived from the clones RD3 (=K102.1) and RB6 (K102.2) selected in the following working examples.

In an embodiment of the present disclosure, the antibody or antigen binding fragment of (i) comprises the amino acid sequence of SEQ ID NO: 36 and the antibody or antigen binding fragment of (ii) comprises the amino acid sequence of SEQ ID NO: 27, but with no limitations thereto.

In an embodiment of the present disclosure, the pair of the RBD antibodies of anti-SARS-CoV-2 S protein or an antigen binding fragments in the composition binds specifically to the receptor binding domain (RBD) of SARS-CoV-2 S protein. Therefore, the pair of antibodies or antigen binding fragments in the composition can be used for detecting SARS-CoV-2 S protein or diagnosing SARS-CoV-2 infection (COVID-19).

In a particular embodiment of the present disclosure, the pair of antibodies or antigen binding fragments in the composition is characterized by targeting different epitopes in the RBD of SARS-CoV-2 S protein.

As used herein, the term "epitope" is a specific antigen determinant that is recognized and bound by a paratope of an antibody to diagnose or detect the target. Specifically, antibodies with different antigenic determinants to the RBD of the SARS-CoV-2 S protein were selected for diagnosing or detecting the target SARS-CoV-2 virus. The utilization of the pairs of antibodies enables a faster and more accurate test.

In an embodiment of the present disclosure, the pair of antibodies and antigen-binding fragments thereof in the composition of the present disclosure specifically binds to variant viruses with mutations generated in the S protein of SARS-CoV-2.

In an embodiment of the present invention, the pair of antibodies and antigen-binding fragments thereof in the composition specifically binds to variant viruses where mutations have occurred in the RBD region of the S protein of SARS-CoV-2. The amino acid sequence of the RBD region is represented by SEQ ID NO: 19.

In a particular embodiment of the present disclosure, the variant virus with a mutation generated in the RBD region of SARS-CoV-2 to which the pair of antibodies or antigen binding fragments thereof in the composition bind is a virus where the mutation on the RBD region is selected from the group consisting of mutations A435S at position 435, N354D at position 354, G476S at position 476, V483A at position 483, F342L at position 342, V341I at position 341, N501Y at position 501, and L452R/T478K at positions 452/478, but with no limitations thereto.

In a more particular embodiment, the variant virus with a mutation generated in the RBD region of SARS-CoV-2 is selected from, but not limited to, the group consisting of the following viruses:

(i) a SARS-CoV-2 variant virus that bears mutation A435S and thus includes a variant RBD in which the alanine residue at position 435 on the amino acid sequence of SEQ ID NO: 56 for wild-type RBD is mutated to serine, wherein the mutation A435S RBD includes the amino acid sequence of SEQ ID NO: 57;

(ii) a SARS-CoV-2 variant virus that bears mutation N354D and thus includes a variant RBD in which the asparagine residue at position 354 on the amino acid sequence of SEQ ID NO: 56 for wild-type RBD is mutated to aspartic acid, wherein the mutation N354D RBD includes the amino acid sequence of SEQ ID NO: 58;

(iii) a SARS-CoV-2 variant virus that bears mutation G476S and thus includes a variant RBD in which the glycine residue at position 476 on the amino acid sequence of SEQ ID NO: 56 for wild-type RBD is mutated to serine, wherein the mutation G476S RBD includes the amino acid sequence of SEQ ID NO: 59;

(iv) a SARS-CoV-2 variant virus that bears mutation V483A and thus includes a variant RBD in which the valine residue at position 483 on the amino acid sequence of SEQ ID NO: 56 for wild-type RBD is mutated to alanine, wherein the mutation V483A RBD includes the amino acid sequence of SEQ ID NO: 60;

(v) a SARS-CoV-2 variant virus that bears mutation F342L and thus includes a variant RBD in which the asparagine residue at position 342 on the amino acid sequence of SEQ ID NO: 56 for wild-type RBD is mutated to leucine, wherein the mutation F342L RBD includes the amino acid sequence of SEQ ID NO: 61;

(vi) a SARS-CoV-2 variant virus that bears mutation V341I and thus includes a variant RBD in which the valine residue at position 341 on the amino acid sequence of SEQ ID NO: 56 for wild-type RBD is mutated to isoleucine, wherein the mutation V341I RBD includes the amino acid sequence of SEQ ID NO: 62;

(vii) a SARS-CoV-2 variant virus that bears mutation N501Y and thus includes a variant RBD in which the asparagine residue at position 501 on the amino acid sequence of SEQ ID NO: 56 for wild-type RBD is mutated to tyrosine, wherein the mutation N501Y RBD includes the amino acid sequence of SEQ ID NO: 63; and (viii) a SARS-CoV-2 variant virus that bears mutation L452R/T478K and thus includes a variant RBD in which the leucine and threonine residues at positions 452 and 478 on the amino acid sequence of SEQ ID NO: 56 for wild-type RBD are mutated to arginine and lysine, respectively, wherein the mutation L452R/T478K RBD includes the amino acid sequence of SEQ ID NO: 64.

The detecting composition or diagnostic composition of the present disclosure contains the anti-SARS-CoV-2 S protein-specific antibody or the antigen binding fragment thereof according to the present disclosure as constituents and is designed to detect the same virus or diagnose the same disease as for the pharmaceutical composition of the present disclosure. The common contents therebetween are omitted in order to avoid undue complexity of the description.

According to another aspect thereof, the present disclosure provides a kit for detecting SARS-CoV-2 viruses or for diagnosing SARS-CoV-2 infectious disease (COVID-19), the kit comprising the composition for detecting SARS-CoV-2 viruses or the composition for diagnosing SARS-CoV-2 infectious disease (COVID-19).

According to a further other aspect thereof, the present disclosure provides a kit for detecting SARS-CoV viruses or for diagnosing SARS-CoV infectious disease, the kit comprising the composition for detecting SARS-CoV viruses or the composition for diagnosing SARS-CoV infectious disease.

In an embodiment thereof, the present disclosure provides a kit for diagnosis of SARS-CoV-2 infection (COVID-19) or for detection of a SARS-CoV-2 antigen, the kit comprising a pair of the following antibodies or antigen binding fragments thereof, each antibody or fragment binding specifically to a receptor binding domain (RBD) of SARS-CoV-2 S protein:

(i) HCDR1 comprising the amino acid sequence of SEQ ID NO: 1, HCDR2 comprising the amino acid sequence of SEQ ID NO: 2, HCDR3 comprising the amino acid sequence of SEQ ID NO: 3, LCDR1 comprising the amino acid sequence of SEQ ID NO: 4, LCDR2 comprising the amino acid sequence of SEQ ID NO: 5, and LCDR3 comprising the amino acid sequence of SEQ ID NO: 6, or antigen binding fragments thereof; and (ii) HCDR1 comprising the amino acid sequence of SEQ ID NO: 9, HCDR2 comprising the amino acid sequence of SEQ ID NO: 10, HCDR3 comprising the amino acid sequence of SEQ ID NO: 11, LCDR1 comprising the amino acid sequence of SEQ ID NO: 12, LCDR2 comprising the amino acid sequence of SEQ ID NO: 13, and LCDR3 comprising the amino acid sequence of SEQ ID NO: 14, or antigen binding fragments thereof.

As used herein, "detection" refers to verifying the presence or absence of an infection related to a certain disease in subject or the presence or absence of a specific target in a sample by using the purpose of the substance or product of the present disclosure. Specifically, the term involves confirming and identifying the presence of the SARS-CoV-2 virus by using the composition or kit of the present disclosure.

In detail, the "detection" means determining the presence or absence of an antibody-antigen-antibody complex in the kit of the present disclosure using various labeling substances. The term "antibody-antigen-antibody complex", as used herein, refers to a conjugate between a SARS-CoV-2 RBD antigen and an antibody pair of the present disclosure which are reacted with each other to determine the presence or absence of SARS-CoV-2 virus in a sample. It also encompasses a conjugate between SARS-CoV-2 virus itself and an antibody pair of the present disclosure. The formation of the antibody-antigen-antibody may be confirmed by a method selected from the group consisting of a colorimetric method, an electrochemical method, a fluorometric method, luminometry, a particle counting method, absorbance measurement, a spectrometric method, a Raman spectroscopic method, a surface plasmon resonance method, visual assessment, and a scintillation counting method, but with no limitations thereto.

As used herein, the term "limit of detection" (LOD) refers to the lowest signal or the lowest corresponding quantity to be determined from the signal, which can be observed with a sufficient degree of confidence, completely distinct from the null (0) quantity or concentration.

The term "sensitivity", as used herein, refers to the ratio of changes in measured values in response to changes in the quantity or concentration of the analyte in the test sample. The greater the sensitivity (slope of the calibration curve) of the test method, the more easily subtle changes in the amount or concentration of the analyte can be detected.

As used herein, the term "sample" is intended to encompass a "biological sample" and a "non-biological sample". The "biological sample" includes, but is not limited to, nasal swab, nasopharyngeal lavage fluid, bronchoalveolar lavage fluid, pleural effusion, sputum, tissues, cells, whole blood, serum, plasma, saliva, cerebrospinal fluid, and urine. The "non-biological samples" include environmental samples such as soil, water, air, food, etc., and other samples.

SARS-CoV-2 virus can be detected by reacting these samples, whether either manipulated or not, with a pair of antibodies or antigen-binding fragments thereof included in the composition of the present disclosure, or by using the kit of the present disclosure.

As used herein, the term “kit” refers to an assembly of means, such as a solid support plate or a test strip, for diagnosing the presence or absence of a target or for detecting a target. Thus, a kit consists of one or more different component compositions, solutions or devices suitable for diagnostic and analytical methods.

The kit can be fabricated using methods typically used in the art. Specifically, because the kit contains a pair of antibodies or antigen-binding fragments thereof, it inherently enables the diagnosis or detection of the SARS-CoV-2 virus through the antigen-antibody binding reaction. Therefore, the kit can be fabricated for suitable use in various immunoassays or immunostaining methods. For example, measurement can be conducted by a method such as using enzyme-linked immunosorbent assay (ELISA), radioimmunoassay (RIA), immunoprecipitation, flow cytometry, immunohistochemical staining, fluorescence immunoassay, and enzyme-substrate coloring assay, with preference for ELISA and most preference for sandwich ELISA. With respect to the immunoassay or immunostaining assay, reference may be made to Enzyme Immunoassay, E. T. Maggio, ed., CRC Press, Boca Raton, Florida, 1980; Gaastra, W., Enzyme-linked immunosorbent assay (ELISA), in Methods in Molecular Biology, Vol. 1, Walker, J. M. ed., Humana Press, NJ, 1984; and Ed Harlow and David Lane, Using Antibodies: A Laboratory Manual, Cold Spring Harbor Laboratory Press, 1999, the disclosures of which are hereby incorporated by reference.

In addition, the kit includes tools and reagents typically used for immunological analysis in the art as well as the detection of SARS-CoV-2 virus of the present disclosure. Examples of the tools and reagents include, but are not limited to, suitable carriers, solubilizers, detergents, buffers, stabilizers, and the like. Suitable carriers include soluble carriers, for example, biologically acceptable buffers known in the art, e.g., PBS, or insoluble carriers, for example polystyrene, polyethylene, polypropylene, polyester, polyacrylonitrile, fluorine resin, crosslinked dextran, polysaccharide, polymers, such as latex containing magnetic fine particles plated with metal, paper, glass, metal, agarose and combinations thereof, but with no limitations thereto.

In a particular embodiment of the present disclosure, the kit may be a kit adapted to utilize sandwich ELISA wherein the antibody or antigen binding fragment of (i) is used as a capture antibody and the antibody or antigen binding fragment of (ii) is used as a detection antibody, or vice versa.

As used herein, the term “sandwich ELISA” refers to a technique to detect or quantitatively analyze a target by utilizing two types of antibodies binding specifically to the target. As stated in the foregoing, the present disclosure provides a composition containing a pair of antibodies or antigen binding fragments thereof targeting different respective epitopes on the RBD of SARS-CoV-2 S protein, wherein any one of the paired antibodies or antigen binding fragments serves as a capture antibody and another is used as a detection antibody, thereby forming the sandwich pattern of an antibody-antigen-antibody complex.

In the case where the present disclosure is carried out in a Sandwich ELISA mode, a particular embodiment of the present disclosure includes the steps of (i) coating a surface of a solid support with the capture antibody; (ii) reacting a capture antibody with a SARS-CoV-2 RBD antigen in a sample; (iii) reacting the antigen on the capture antibody-antigen complex of step (ii) with a detection antibody; (iv) further reacting the resulting product (capture antibody-antigen-detection antibody) of step (iii) with a signal-detecting antibody conjugated with a signal-generating label; and (v) measuring the signal generated from the label.

As used herein, the term “capture antibody” refers to an antibody that first reacts with a target substance while being immobilized onto a solid support which may be usable as a reaction vessel.

Suitable as the solid support is a hydrocarbon polymer (e.g., polystyrene and polypropylene), glass, metal, or gel, with the most preference for microtiter plates.

The term “detection antibody”, as used herein, refers to an antibody that can react with the target immobilized by the capture antibody to form the sandwich pattern of a capture antibody-target substance (antigen)-detection antibody complex. In addition, the detection antibody is an antibody that can be indirectly detected by a different labeled antibody and forms a complex in a sandwich pattern, thereby facilitating the detection of the target substance.

The detection of the complex in a sandwich form is carried out by further adding a “signal-detecting antibody” conjugated with a label generating a signal, reacting same with the detection antibody, and measuring the signal generated from the signal-detecting antibody. Therefore, the “signal-detecting antibody” refers to an antibody that can be directly detected through the label conjugated thereto. The label includes, but is not limited to, chemicals (e.g., biotin), enzymes (e.g., alkaline phosphatase), β-galactosidase, HRP (horseradish peroxidase) and cytochrome P450, radioisotopes (e.g., C14, I125, P32, and S35), fluorophores (e.g., fluorescein), luminophores, chemiluminescents, and FRET (fluorescence resonance energy transfer). With respect to various labels and labeling methods, reference may be made to Ed Harlow and David Lane, Using Antibodies: A Laboratory Manual, Cold Spring Harbor Laboratory Press, 1999.

In detail, in an embodiment of the present disclosure, the label conjugated to the signal-detecting antibody includes enzymes for catalyzing chromogenic reactions, fluorescent reactions, luminescent reactions, or infrared reactions, but is not limited thereto. For example, the label may include β-galactosidase, HRP (horseradish peroxidase), alkaline phosphatase, colloid gold, FITC (poly L-lysine fluorescein isothiocyanate), RITC (rhodamine-B-isothiocyanate), luciferase, and cytochrome P450, but is not limited thereto. A substrate for the enzyme conjugated to the signal-detecting antibody may be a chromogenic reaction substrate such as BCIP (5-bromo-4-chloro-3-indolyl-phosphate), NBT (nitro blue tetrazolium), naphthol-AS-B1-phosphate, and ECR (enhanced chemifluorescence reaction) when the enzyme is alkaline phosphatase and may include chloronaphthol, AEC (3-amino-9-ethylcarbazole), DAB (3,3'-o-diaminobenzidine), D-luciferin, lucigenin (bis-N-methylacridinium nitrate), luminol, resorufin benzyl ether, Amplex® Red (10-acetyl-3,7-dihydroxyphenoxazine; ADHP), HYP (p-phenylenediamine-HCl and pyrocatechol), TMB (3,3',5,5'-Tetramethylbenzidine), ABTS (2,2'-azino-bis(3-ethylbenzothiazoline-6-sulfonic acid)), O-phenylenediamine (OPD) and naphthol/pyronine, glucose oxidase, t-NBT (nitroblue tetrazolium), and m-PMS (phenzaine methosulfate) when the enzyme is HRP.

In an embodiment of the present disclosure, the concentration of the capture antibody and the detection antibody in the kit may be 0.1 to 15 μg/ml and, more particularly, 0.1 to 12 μg/ml, 0.1 to 10 μg/ml, 0.1 to 8 μg/ml, 0.1 to 7 μg/ml, 0.1 to 6 μg/ml, 0.1 to 5 μg/ml, 0.1 to 4 μg/ml, 0.1 to 3 μg/ml, 0.1 to 2 μg/ml, 0.1 to 1 μg/ml, 0.5 to 10 μg/ml, 0.5 to 8 μg/ml, 0.5 to 7 μg/ml, 0.5 to 6 μg/ml, 0.5 to 5 μg/ml, 0.5 to 4 μg/ml, 0.5 to 3 μg/ml, 0.5 to 2 μg/ml, 0.5 to 1 μg/ml, 0.5 μg/ml, 1 μg/ml, 2 μg/ml, 3 μg/ml, 4 μg/ml, 5 μg/ml, 6 μg/ml, 7 μg/ml, 8 μg/ml, 9 μg/ml, or 10 μg/ml, but is not limited thereto.

In another embodiment of the present disclosure, the concentration of the capture antibody in the kit may be higher than that of the detection antibody.

In an embodiment of the present disclosure, the kit may contain the capture antibody at a concentration of 5 μg/ml and the detection antibody at a concentration of 1 μg/ml.

According to another aspect thereof, the present disclosure provides a method for detecting a SARS-CoV-2 antigen from a sample, using the kit for detecting a SARS-CoV-2 antigen according to the present disclosure.

Since the method for detecting a SARS-CoV-2 antigen from a sample according to an aspect of the present disclosure includes the kit for detecting a SARS-CoV-2 antigen according to another aspect of the present disclosure described above, the common content is omitted to avoid undue complexity of the description.

The antibody of the present disclosure may be used for in vivo or in vitro imaging. According to another aspect of the present disclosure, the present disclosure provides a composition for imaging, containing a conjugate in which the antibody of the present disclosure is conjugated to a label generating a detectable signal conjugated to the antibody.

The label capable of generating a detectable signal includes T1 contrast materials (e.g., Gd chelate compounds), T2 contrast materials (e.g., superparamagnetic materials (i.e., magnetite, $Fe_3O_4$, $\gamma$-$Fe_2O_3$, manganese ferrite, cobalt ferrite, and nickel ferrite)), radioactive isotopes (e.g., $^{11}C$, $^{15}O$, $^{13}N$, $P^{32}$, $S^{35}$, $^{44}Sc$, $^{45}Ti$, $^{118}I$, $^{136}La$, $^{198}Tl$, $^{200}Tl$, $^{205}Bi$, and $^{206}Bi$), fluorescent materials (fluorescein, phycoerythrin, rhodamine, lissamine, and Cy3/Cy5), chemiluminescent materials, magnetic particles, mass labels, and dense electron particles, but are not limited thereto.

According to an aspect thereof, the present disclosure provides a bispecific antibody to SARS-CoV-2.

In an embodiment of the present disclosure, the bispecific antibody binds specifically to SARS-CoV-2 and includes:

(a) an antibody comprising a heavy chain variable region and a light chain variable region, or an antigen binding fragment, the heavy chain variable region comprising heavy chain complementarity determining region 1 (HCDR1) having the amino acid sequence of SEQ ID NO: 28, H-CDR2 having the amino acid sequence of SEQ ID NO: 29, and H-CDR3 having the amino acid sequence of SEQ ID NO: 30; and the light chain variable comprising light chain comprising complementarity determining region 1 (L-CDR1) having the amino acid sequence of SEQ ID NO: 31, L-CDR2 having the amino acid sequence of SEQ ID NO: 32, and L-CDR3 having the amino acid sequence of SEQ ID NO: 33; and (b) an antibody comprising a heavy chain variable region and a light chain variable region, or an antigen binding fragment, the heavy chain variable region comprising HCDR1 having the amino acid sequence of SEQ ID NO: 19, H-CDR2 having the amino acid sequence of SEQ ID NO: 20, and H-CDR3 having the amino acid sequence of SEQ ID NO: 21; and the light chain variable comprising light chain comprising L-CDR1 having the amino acid sequence of SEQ ID NO: 22, L-CDR2 having the amino acid sequence of SEQ ID NO: 23, and L-CDR3 having the amino acid sequence of SEQ ID NO: 24.

In an embodiment of the present disclosure, the antibodies or antigen binding fragments in (a) and (b) are derived respectively from the monoclonal antibodies RD3 (=K102.1) and RB6 (=K102.2) selected in the working examples.

The bispecific antibody according to an aspect of the present disclosure is in the form of a dimer or a multimer in which individual antibody or antigen binding fragment constituents are linked to each other. The antibody or antigen binding fragment constituents are linked to each other via a covalent bond. In an embodiment of the present disclosure, the bispecific antibody may be embodied into a fused protein or conjugate form. Hence, the antibodies or antigen binding fragments thereof may be indirectly coupled through chemical conjugation (known as an organic chemical method) or other means (e.g., expressed as a fusion protein or directly or via a linker (i.e., amino acid linker)).

In an embodiment of the present disclosure, the heavy variable region of (a) includes the amino acid sequence of SEQ ID NO: 34.

In an embodiment of the present disclosure, the light variable region of (a) includes the amino acid sequence of SEQ ID NO: 35.

In an embodiment of the present disclosure, the heavy variable region of (b) includes the amino acid sequence of SEQ ID NO: 25.

In an embodiment of the present disclosure, the light variable region of (b) includes the amino acid sequence of SEQ ID NO: 26.

In an embodiment of the present disclosure, the antibody or antigen binding fragment of (a) includes a heavy chain comprising the amino acid sequence of SEQ ID NO: 65.

In the bispecific antibody according to an embodiment of the present disclosure, the antibody or antigen binding fragment of (a) includes a light chain comprising the amino acid sequence of SEQ ID NO: 66.

In an embodiment of the present disclosure, the antibody or antigen binding fragment of (b) is an scFv comprising the amino acid sequence of SEQ ID NO: 27.

In an embodiment of the present disclosure, the antibody or antigen binding fragment of (a) is linked to the C terminus of the heavy chain in the antibody or antigen binding fragment of (b) or the antibody or antigen binding fragment of (b) is linked to the C terminus of the heavy chain in the antibody or antigen binding fragment of (a).

In an embodiment of the present disclosure, the antibody or antigen binding fragment of (b) in the bispecific antibody is linked to the C terminus of the heavy chain in the antibody or antigen binding fragment of (a), but with no limitations thereto.

In an embodiment of the present disclosure, the antibody or antigen binding fragment of (a) is linked to the N- or C-terminus of the light chain in the antibody or antigen binding fragment of (b) or the antibody or antigen binding fragment of (b) is linked to the N- or C-terminus of the light chain in the antibody or antigen binding fragment of (a).

In an embodiment of the present disclosure, the antibody or antigen binding fragment of (b) is linked to the N-terminus of the light chain in the antibody or antigen binding fragment of (a), but with no limitations thereto.

In an embodiment of the present disclosure, the antibody or antigen binding fragment of (b) is linked to the C-terminus of the light chain in the antibody or antigen binding fragment of (a).

In an embodiment of the present disclosure, the antibody or antigen binding fragment of (a) and the antibody or antigen binding fragment of (b) bind to respective different epitopes on the receptor binding domain (RBD) of SARS-CoV-2 Spike protein.

In an embodiment of the present disclosure, the bispecific antibody inhibits the binding of the RBD of SARS-CoV-2 Spike protein to angiotensin converting enzyme 2 (ACE2) in host cells.

In an embodiment of the present disclosure, the antibody or antigen binding fragment of (a) and the antibody or antigen binding fragment of (b) are each in a form of IgG1 or IgG4, but with no limitations thereto.

In an embodiment of the present disclosure, the antibody or antigen binding fragment of (a) is in a form of IgG1 or IgG4, but with no limitations thereto.

In an embodiment of the present disclosure, the antibody or antigen binding fragment of (a) and the antibody or antigen binding fragment of (b) are each in a form of IgG1 or IgG4 and the antibody or antigen binding fragment of (b) is in a form of scFv.

According to another aspect thereof, the present disclosure provides a nucleic acid molecule comprising a nucleotide sequence coding for the bispecific antibody that binds specifically to SARS-CoV-2.

According to another aspect thereof, the present disclosure provides a recombinant vector carrying the nucleic acid molecule.

According to another aspect thereof, the present disclosure provides an isolate host cell anchoring the recombinant vector therein.

According to another aspect thereof, the present disclosure provides a pharmaceutical composition containing the bispecific antibody and a pharmaceutically acceptable carrier for treatment of SARS-CoV-2 infection.

In an embodiment of the present disclosure, the SARS-CoV-2 is a variant having, on the amino acid sequence of RBD, a mutation selected from the group consisting of N354D/D364Y, V367F, W436R, R408I, G476S, V483A, V341I, F342L, A435S, and a combination thereof, but with no limitations thereto.

In an embodiment of the present disclosure, the SARS-CoV-2 is selected from the group consisting of a wild type, an alpha variant, a beta variant, a gamma variant, a delta variant, and a kappa variant, but with no limitations thereto.

Advantageous Effects of Invention

With the ability to inhibit the infection of SARS-CoV2 by binding specifically to the S protein responsible for the entry of SARS-CoV-2 into host cells, the anti-SARS-CoV-2 S protein-specific antibody or the antigen binding fragment thereof according to the present disclosure can be advantageously used as a therapeutic agent for COVID-19 and as diagnostic agent and kit for COVID-19.

BRIEF DESCRIPTION OF DRAWINGS

FIG. 32 is a table showing CV values and recovery of intra- and inter-assay for optimized sandwich ELISA.

BEST MODE FOR CARRYING OUT THE INVENTION

A better understanding of the present disclosure may be obtained through the following examples which are set forth to illustrate, but are not to be construed to limit, the present disclosure.

EXAMPLES I

Throughout the description, the term "%" used to express the concentration of a specific material, unless otherwise particularly stated, refers to (wt/wt) % for solid/solid, (wt/vol) % for solid/liquid, and (vol/vol) % for liquid/liquid.

Figure 1:
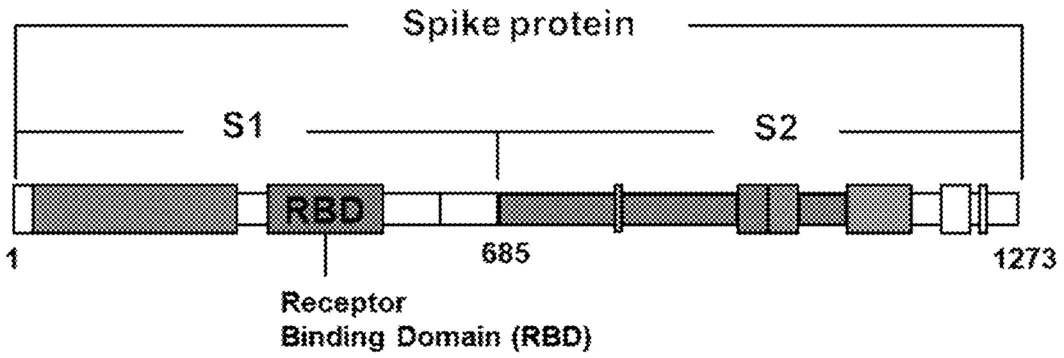
FIG. 1 is a view showing the configuration of S1, S2, and RBD proteins that are constituent proteins of spikes of SARS-CoV-2.

Example I-1. Preparation of SARS-CoV-2 Protein Antigen for Antibody Selection For use in selecting antibodies binding specifically to SARS-CoV-2, the spike full-length protein of SARS-CoV-2 and its constituent proteins S1 and RBD protein antigens were purchased from Sino Biological. The configuration of S1 and RBD proteins in the spike protein is depicted in FIG. 1. The proteins purchased were measured for purity and molecular weight by SDS-PAGE (FIG. 2).

Figure 2:
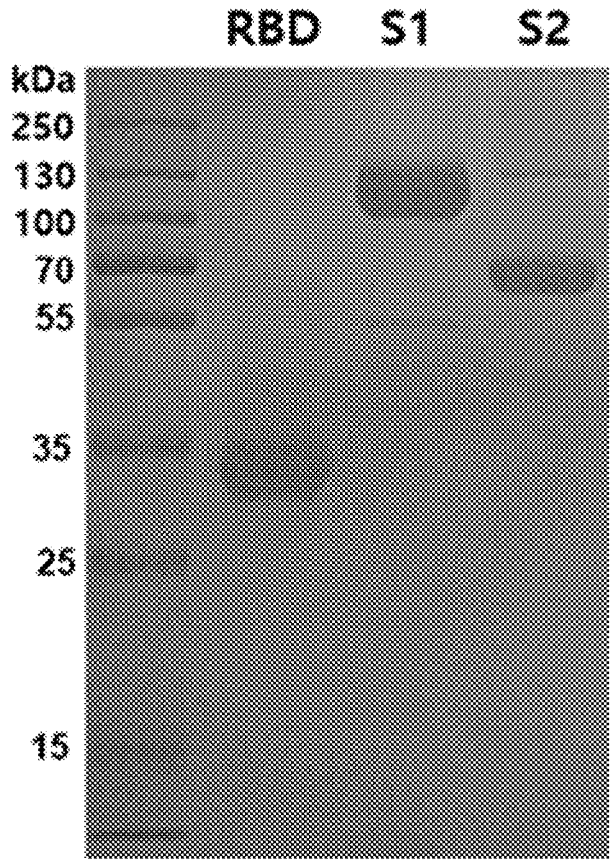
FIG. 2 depicts SDS-PAGE analysis result of purchased SARS-CoV-2 spike proteins S1, S2, and RBD protein antigens.

As shown in FIG. 2, it was observed that the purchased S1, S2, and RBD proteins of the spike protein were high in purity.

Figure 3:
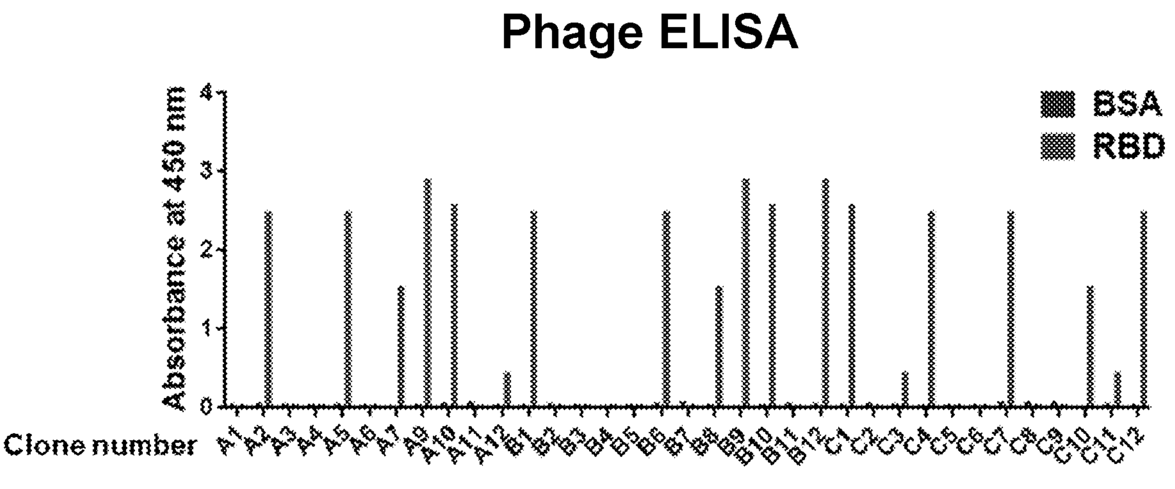
FIG. 3 is a diagram showing results of the scFv binding to RBD and phage ELISA for the selection of human antibodies specific to the RBD antigen of the SARS-CoV-2 virus.

Example I-2: Selection of Human Antibody Specific for RBD Antigen of SARS-CoV-2 Virus by Phage Display Technique A certain amount of secured SARS-CoV-2 RBD antigen was conjugated to epoxy-conjugated Dynabead (Invitrogen, USA), and human antibodies specific for RBD were selected using the phage display technique. After five rounds of bio-panning, binding antibody clones were measured for titer and degree of enrichment by round through titration. Subsequently, human antibody clones that had excellent reactivity to the RBD antigen and were specific for the antigen were selected using individual phage ELISA. The DNA was isolated through miniprep and ten types of RBD-specific human antibodies with different CDR sequences were secured after base sequencing. The results of the phage ELISA are presented in FIG. 3.

Example I-3: IgG Conversion, Production, and Purification of Selected Antibodies 3-1. Conversion of SARS-CoV-2 RBD Antigen-Specific scFv Antibody into IgG (IgG 4 Type)

For heavy and light chains of the ten kinds of RBD domain-specific scFv antibodies selected, insert DNAs were obtained. They were subcloned into bicistronic vectors for production full-IgG (IgG4 type) antibodies. For use in producing IgG antibodies in Expi293 cells, the recombinant DNA of each of the ten different scFvs was isolated in a large amount with high purity by using Maxi-prep kit. The purity of DNA was examined by NanoDrop.

3-2. Mass Production of RBD-Specific IgG (IgG4) Antibody

The 10 different IgG antibodies were transfected into 1 L or greater of Expi293 cells with the aid of the Expi293 system (Invitrogen) comprising ExpiFectamine for transient expression, followed by incubation for 7 days. In order to purify the antibodies, the cultures were centrifuged and the supernatants (media) were obtained by removing the cell pellets.

3-3. Purification and Production Assay of Antibodies

The selected antibodies were purified by affinity column chromatography using protein A sepharose beads. In addition, the RBD-specific IgG antibodies were analyzed for yield after mass production and final purification.

Figure 4:
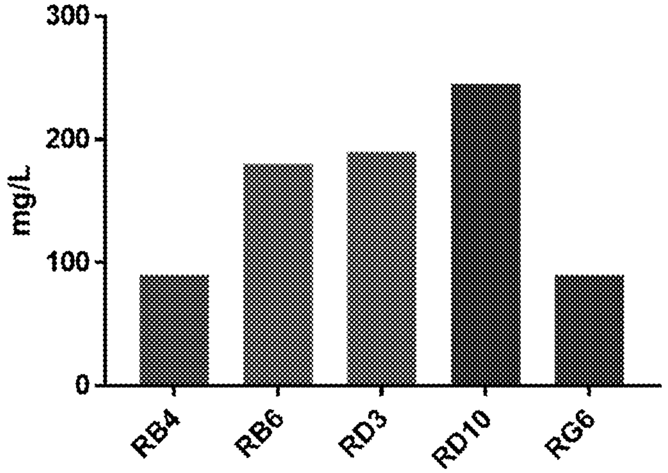
FIG. 4 illustrates the comparison of the yield after mass production and final purification of the SARS-CoV-2 RBD-specific IgG antibodies of the present disclosure.

The analysis of the 10 different RBD-specific antibodies for productivity showed that the five antibodies RB4, RB6, RD3, RD10, and RG6 were produced at high yields of 50 mg/L or higher, with the productivity of 140 mg/L or higher given for RD3, RD10, and RG6 clones (FIG. 4).

Figure 5:
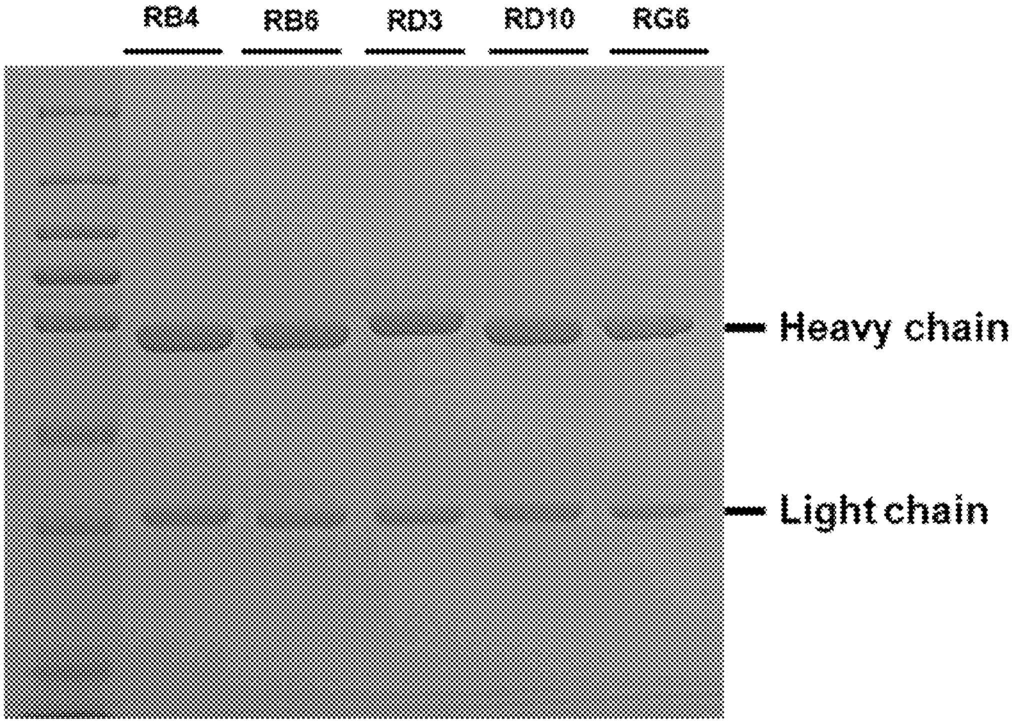
FIG. 5 is an image of the SDS-PAGE result of the five selected SARS-CoV-2 RBD-specific IgG antibodies.

Example I-4: Physical/Chemical Characterization of Selected Antibodies 4-1. Purity and Molecular Weight of Selected Antibodies The five selected SARS-CoV-2 RBD-specific antibodies were loaded at the same content to a polyacrylamide gel. After SDS-PAGE, all the five antibodies were observed to have a purity of 95% or higher and a molecular weight of 50 kDa for heavy chain and 25 kDa for light chain, as analyzed by Coomassie Brilliant Blue staining (FIG. 5).

4-2. Reactivity of Selected Antibodies to SARS-CoV-2 RBD, S1 Domain, and Full-Length Spike Antigens In order to examine the reactivity of the five selected SARS-CoV-2 RBD-specific antibodies to SARS-CoV-2 RBD, S1 domain, and full-length spike protein antigens, 0.1 μg of each antigen was coated on 96-well high binding plates (Corning, USA) and ELISA was conducted for each antibody. The results are depicted in FIG. 6.

Figure 6:
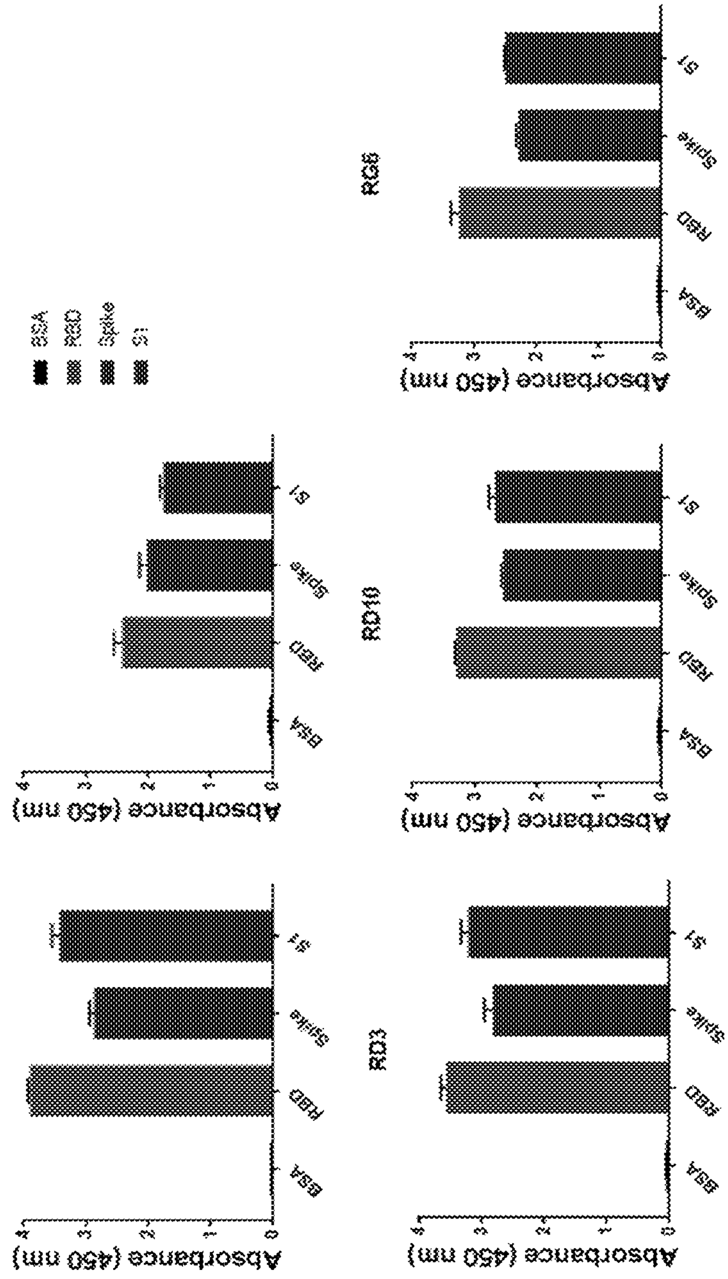
FIG. 6 shows graphs of the reactivity analysis results for the five selected SARS-CoV-2 RBD-specific IgG antibodies against three types of SARS-CoV-2 antigens (RBD, Spike, and S1) using ELISA.

As can be seen in FIG. 6, all the five selected antibodies were observed to have superb reactivity to SARS-CoV-2 Spike, S1, and RBD antigens.

4-3. Cross-Reactivity of Selected Antibodies to SARS-CoV-2 and SARS-CoV RBD Antigens In order to examine the reactivity of the five selected SARS-CoV-2-specific antibodies to SARS-CoV RBD as well as SARS-CoV-2 RBD, 0.1 μg of each of purchased SARS-CoV-2 and SARS-CoV RBD was coated on 96-well high binding plates (Corning, USA) and ELISA was conducted for each antibody. The results are depicted in FIG. 7.

Figure 7:
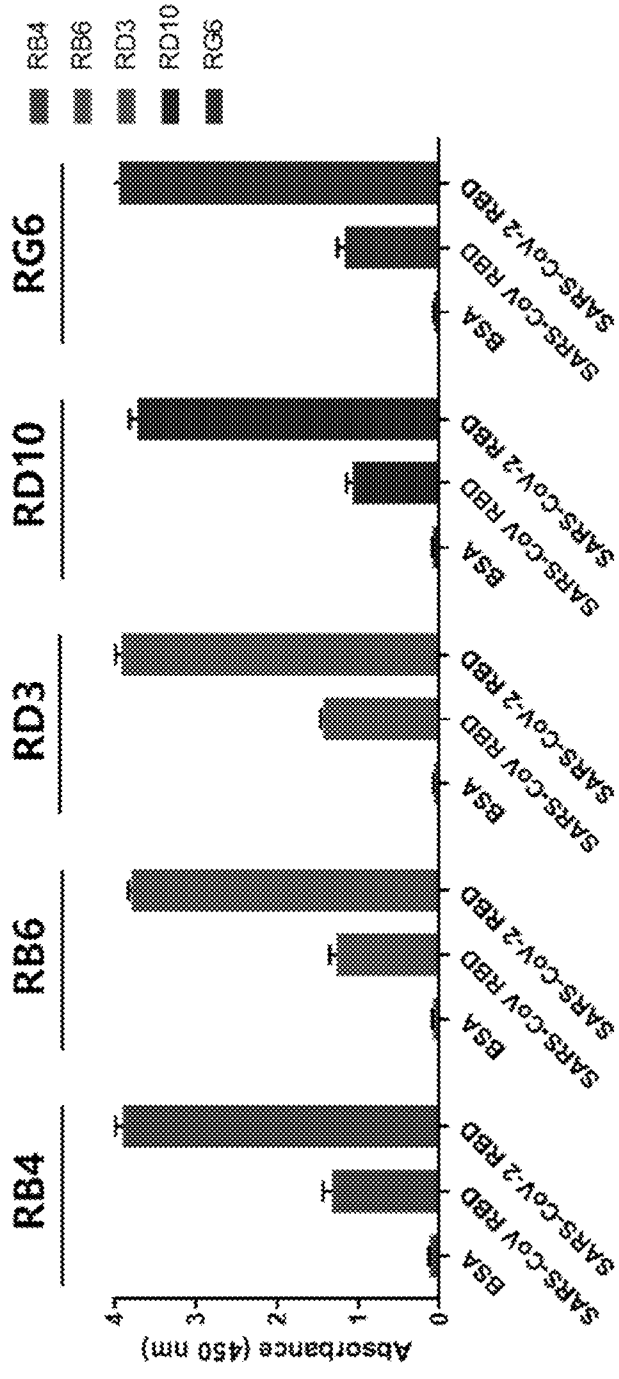
FIG. 7 is a graph of cross-reactivity analysis results of the five selected SARS-CoV-2 RBD-specific IgG antibodies against the RBD antigens of both the SARS-CoV-2 and SARS-CoV viruses, using ELISA.

As shown in FIG. 7, all the five selected antibodies were observed to have reactivity to SARS-CoV RBD antigen, too.

4-4. Affinity ($K_D$ Value) of Selected Antibodies for RBD and S1 Antigens

The five selected antibodies were measured for $K_D$ values for SARS-CoV-2 RBD and S1. In this regard, SARS-CoV-2 RBD and S1 purchased were each bound to 96-well high binding plates (Corning, USA), and absorbance (450 nm) was read while increasing the concentrations of the selected antibodies. The results are depicted in FIGS. 8 and 9.

Figure 8:
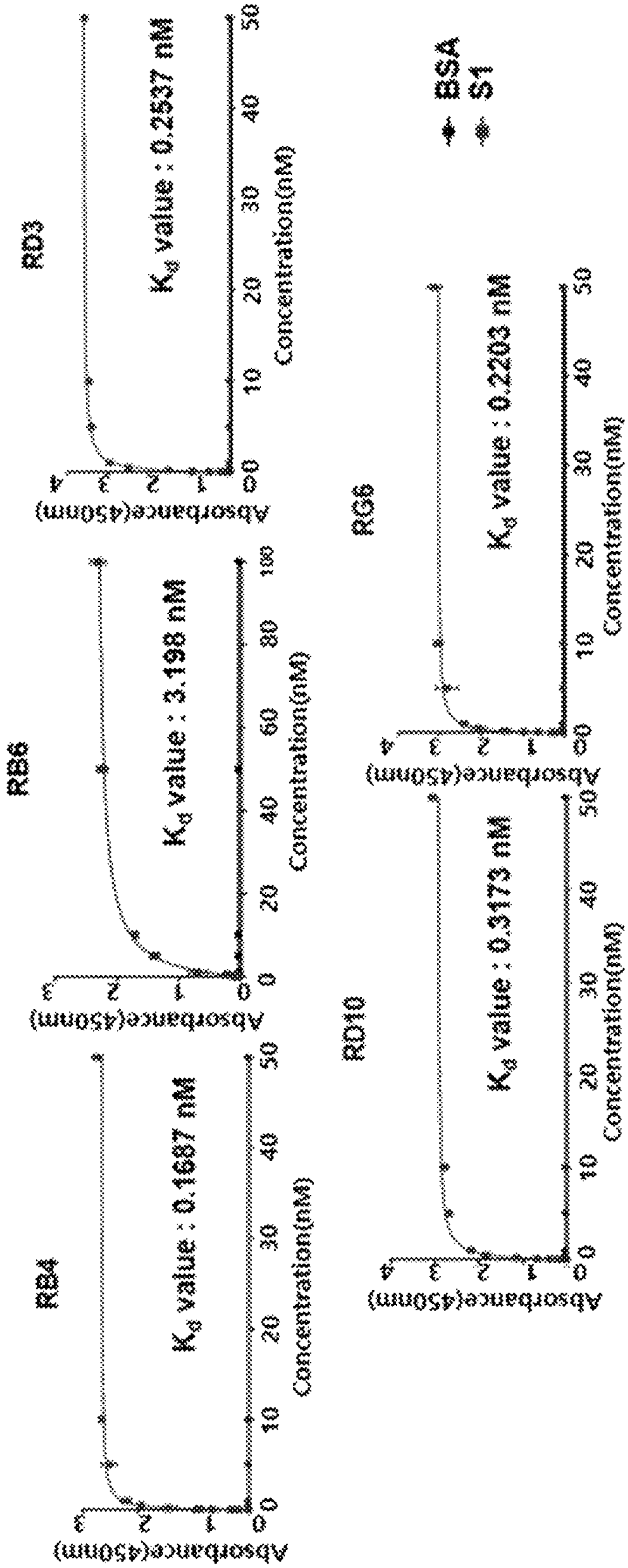
FIG. 8 shows plots of affinity analysis results of the five selected SARS-CoV-2 RBD-specific IgG selected antibodies against the SARS-CoV-2 S1 antigen.

FIG. 8 shows plots of affinity of the five selected RBD-specific antibodies for SARS-CoV-2 S1 antigen. FIG. 9 shows plots of affinity of the five selected RBD-specific antibodies for SARS-CoV-2 RBD antigen.

Figure 9:
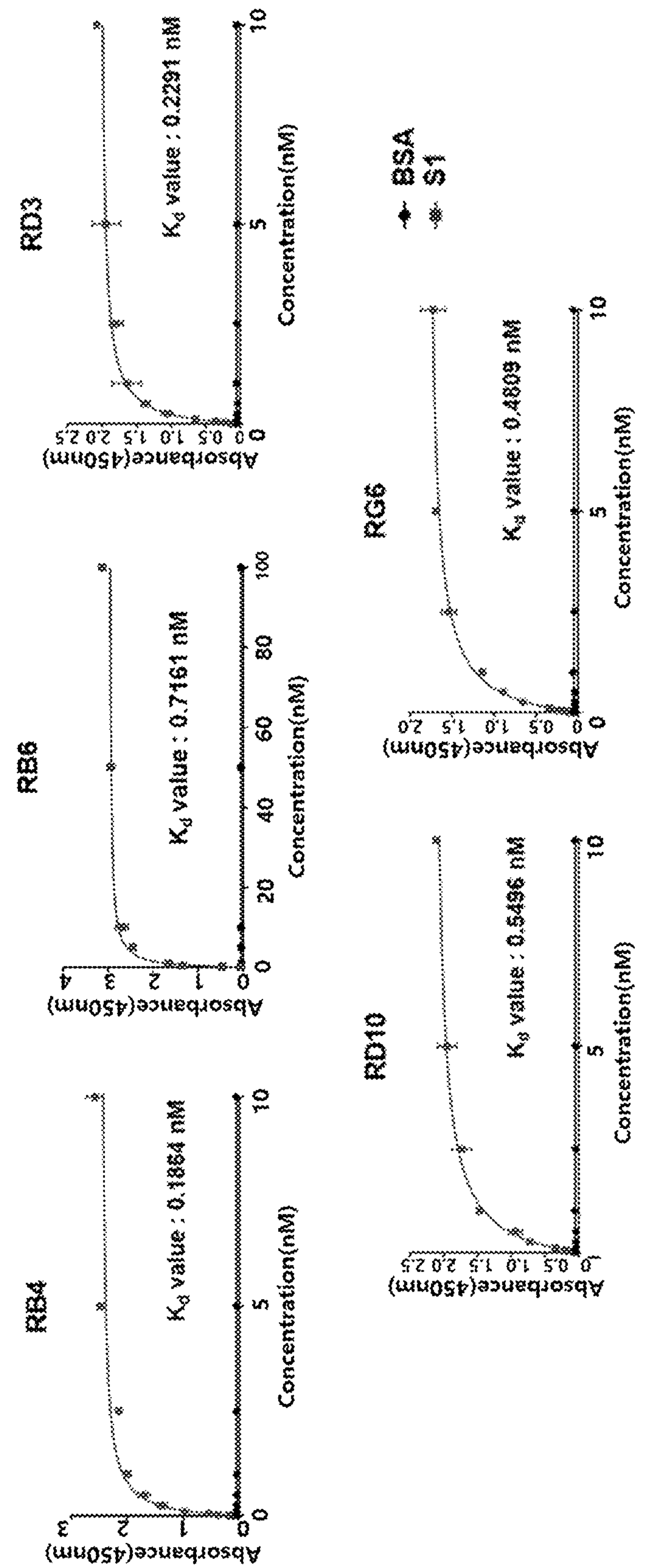
FIG. 9 shows plots of affinity analysis results of the five selected SARS-CoV-2 RBD-specific IgG antibodies against the SARS-CoV-2 RBD antigen.

As shown in FIGS. 8 and 9, $K_D$ values for S1 antigen were decreased in the order of RB4, RG6, RD3, RD10, and RB6 and $K_D$ values for RBD antigen were decreased in the order of RB4, RD3, RG6, RD10, and RB6. Of the five selected antigens, the four antigens RB4, RD3, RD10, and RG6 4 exhibited a $K_D$ value of $10^{-10}$ M for S1 antigen, and all the five antibodies exhibited a $K_D$ value of $10^{-10}$ M for RBD antigen. It was finally confirmed that the selected antibodies had high affinity for each antibody.

4-5. Reactivity of Selected Antibodies to 9 RBD Mutants

Figure 10:
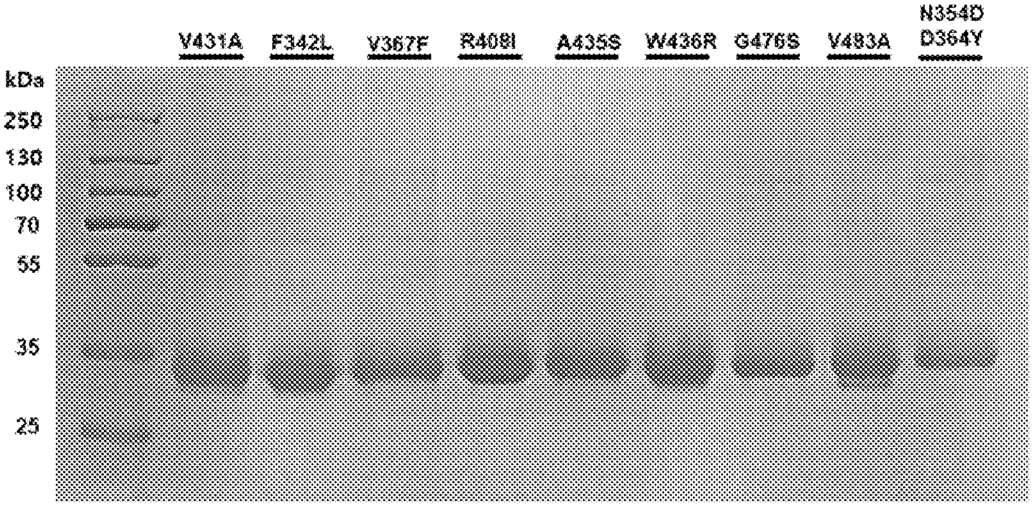
FIG. 10 is an image of the SDS-PAGE analysis results to verify the molecular weight and purity of the nine purchased RBD variant antigens of SARS-CoV-2.

In relation to SARS-CoV-2, nine typical RBD mutant antigens (V431A, F342L, V367F, R408I, A435S, W436R, G476S, V483A, and N354D/D364Y) that were classified worldwide were purchased from Sino Biological. Each of the antigens was measured for purity and molecular weight by SDS-PAGE. As a result, the RBD mutants were measured to have a size of about 30 kDa and a purity of 90% or higher (FIG. 10).

Figure 11:
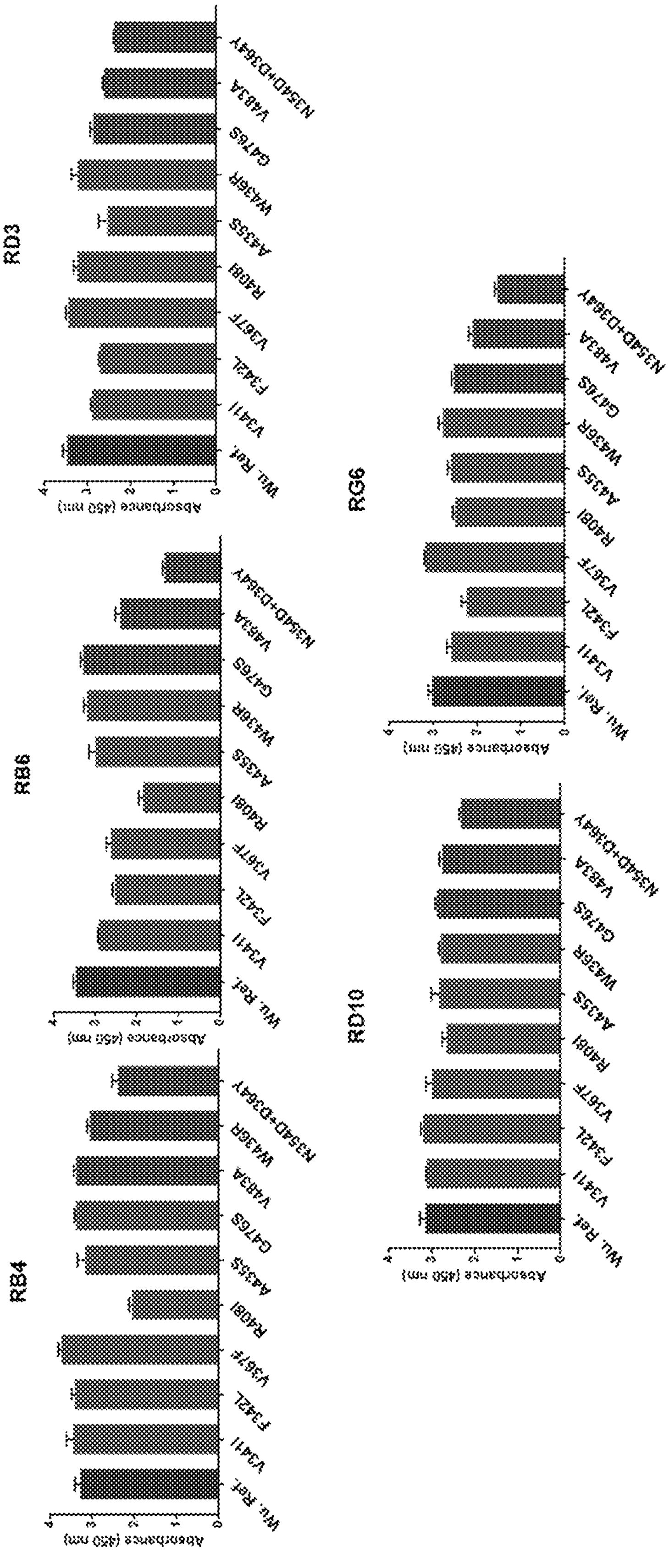
FIG. 11 shows graphs of the reactivity analysis results of the nine RBD variants of SARS-CoV-2 and the five selected SARS-CoV-2 RBD-specific antibodies.

In addition, in order to examine the reactivity of the five selected antibodies to the nine SARS-CoV-2 RBD mutant antigens, ELISA was performed. As a result, all the five selected RBD-specific antibodies were found to bind to the nine RBD mutant protein antigens, too (FIG. 11).

Example I-5: Inhibitory Activity Against Direction Interaction Between hACE2 and SARS-CoV-2 RBD Protein (Functional Analysis for Deriving Leading Substance)

5-1. Establishment of Basic Technology for Direct Interaction Assay

The neutralization ability of antibody to inhibit protein-protein interaction between hACE2 receptor and SARS-CoV-2 spike protein was investigated by ELISA using purified proteins. To this end, neutralization ability was analyzed using the Spike RBD (SARS-CoV-2): ACE2 inhibitor screening assay kit (BPS Bioscience, Cat. No. 79931).

Figure 12:
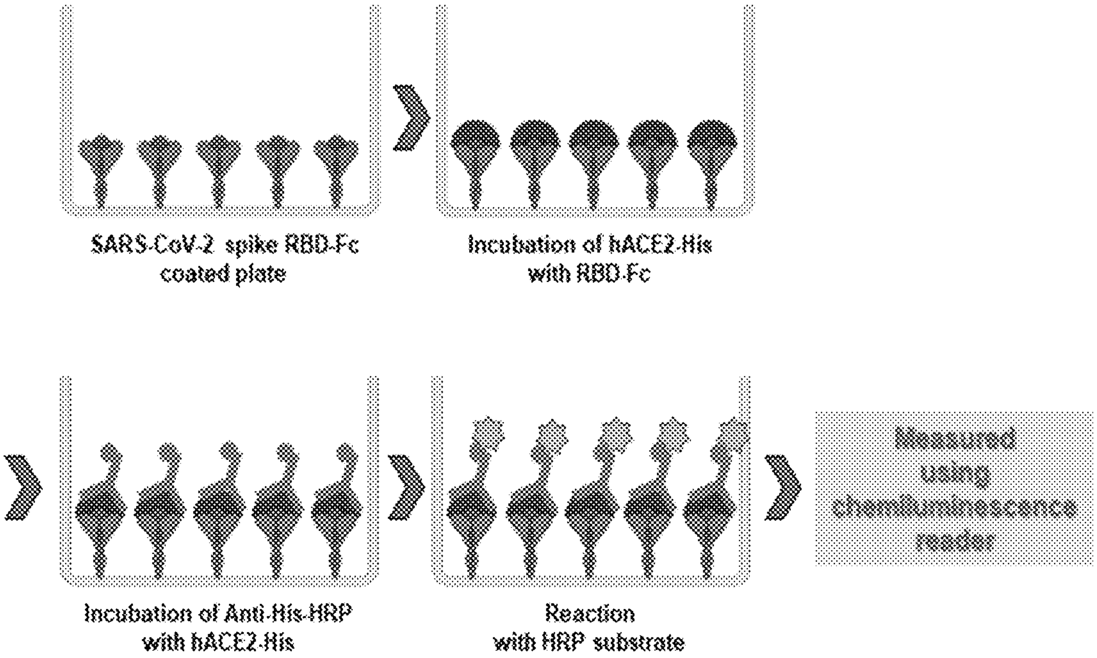
FIG. 12 is a schematic view illustrating the direct interaction assay between hACE2 and SARS-CoV-2 RBD protein.

In brief, SARS-CoV-2 RBD protein (Fc-tagged) was coated on 96-well plates included within the assay kit and incubated with the ligand human ACE2 (His-tagged; hACE2-His). Then, anti-His-HRP and HRP substrate were added before measuring chemiluminescence on ELISA reader to analyze binding affinity between RBD domain-ACE2. A schematic diagram for assaying direct interaction between hACE2-His and SARS-CoV-2 RBD is given in FIG. 12. The assay results are depicted in FIG. 13.

Figure 13:
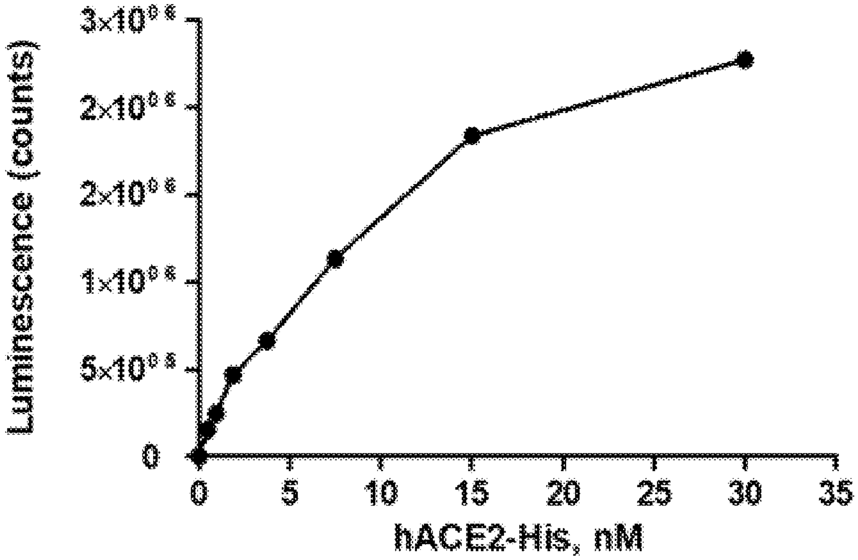
FIG. 13 is a plot of the changes in direct interaction values between the SARS-CoV-2 RBD protein and hACE2, depending on the concentration of hACE2.
Figure 14:
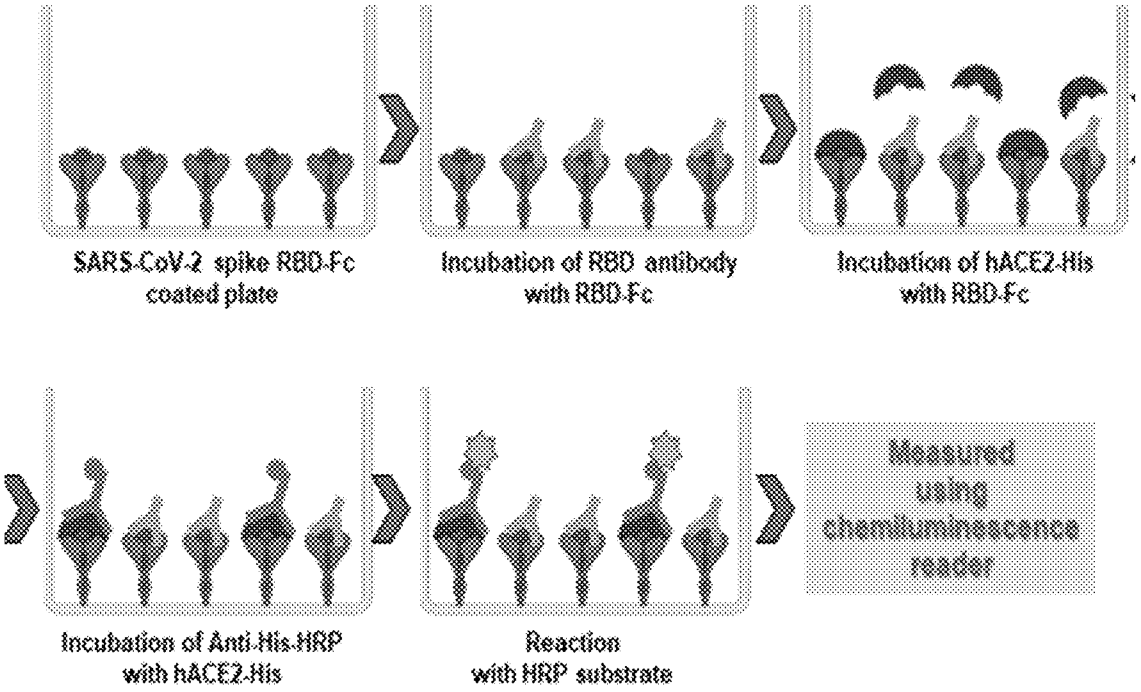
FIG. 14 is a schematic view illustrating an assay of the antibodies for inhibitory activity against direct interaction between hACE2 and SARS-CoV-2 RBD protein.

As shown in FIG. 13, chemiluminescence values increased with increasing of hACE2-His levels, indicating that interaction between hACE2 and SARS-CoV-2 RBD increases with increasing of hACE2 concentration. The median value 10 nM on the standard curve was determined as the concentration of hACE2-His to be used for inhibition assay.

5-2. Assay of RBD Neutralizing Antibody for Inhibiting ACE2-Spike RBD Interaction Using the established direct interaction assay, the selected antibodies were measured for ability to inhibit interaction between SARS-CoV-2 RBD and hACE2.

In brief, SARS-CoV-2 RBD protein (Fc-tagged) was coated on 96-well plates included within the assay kit and incubated with the ligand human ACE2-His alone and in combination with the selected antibodies (0.016, 0.08, 0.4, 2, 10, and 50 nM). Then, anti-His-HRP and HRP substrate were added before measuring chemiluminescence on ELISA reader to analyze the ability of the antibodies to inhibit interaction between SARS-CoV-2 RBD and hACE2. A schematic diagram for assaying direct interaction is given in FIG. 12. The assay results are depicted in FIG. 13.

Figure 15:
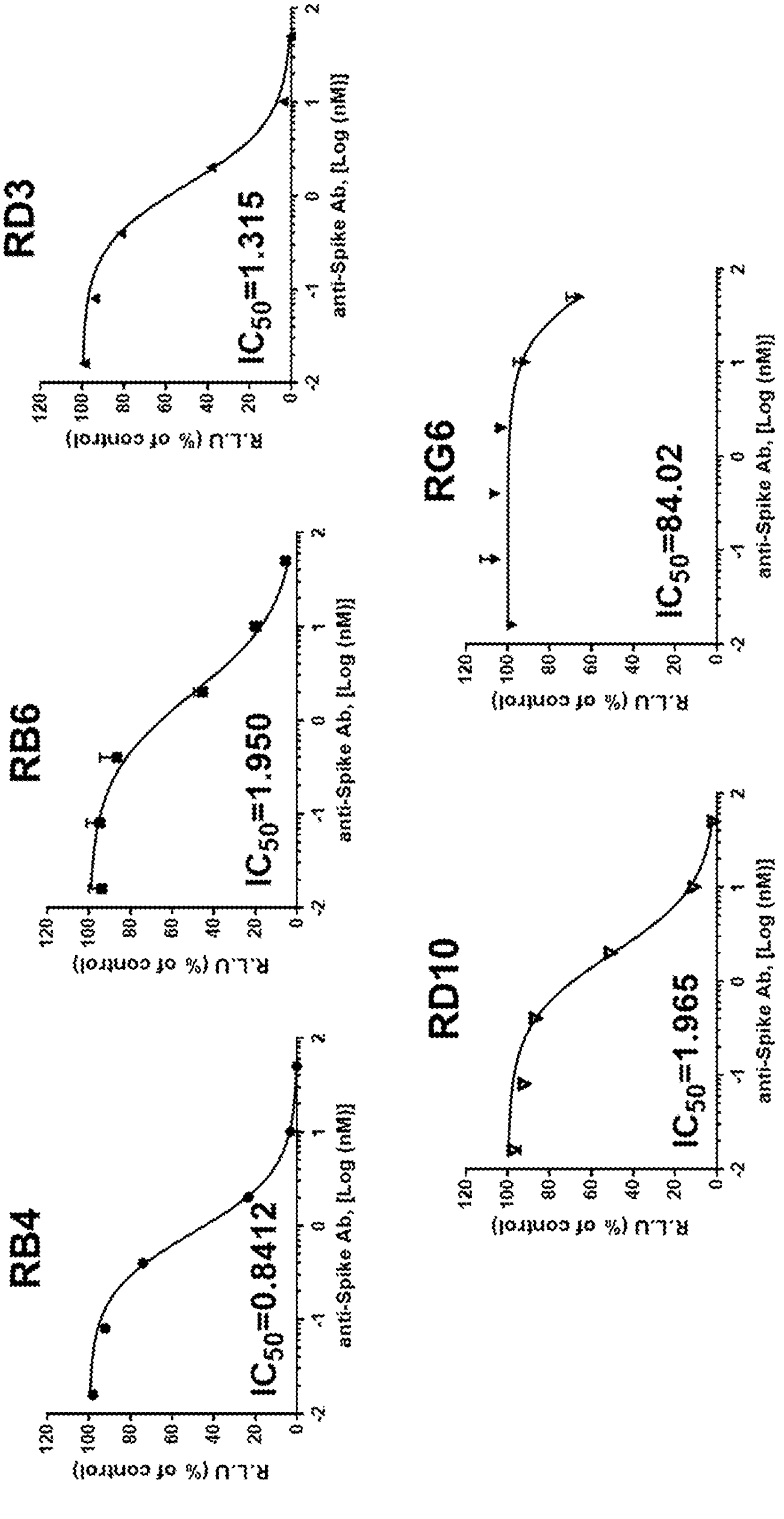
FIG. 15 shows plots of the inhibition activity of the five selected IgG antibodies against direct interaction between hACE2 and SARS-CoV-2 RBD protein, with IC50 measurements given therein.

As shown in FIG. 15, the addition of RB4, RB6, RD3, RD10, and RG6 by concentration effectively inhibited interaction between spike RBD region-hACE2.

In FIG. 15, the IC50 value was measured to be 0.8412 nM for RB4, 1.950 nM for RB6, 1.315 nM for RD3, 1.965 nM for RD10, and 84.02 nM RG6. Among them, the four antibodies RB4, RB6, RD3, and RD10 were observed to effectively inhibit interaction between SARS-CoV-2 RBD and hACE2 even when used at very low concentrations.

Figure 16:
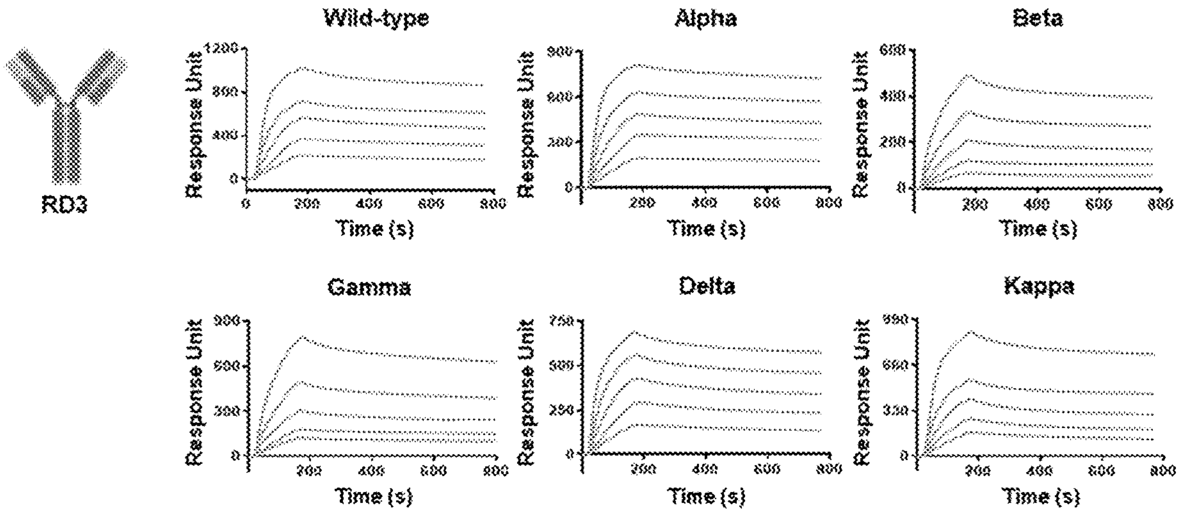
FIG. 16 shows views illustrating that the monoclonal antibody RD3 of the present disclosure has binding affinity for various recombinant SARS-CoV-2 RBDs (wild type, Alpha, Beta, Gamma, Delta, or Kappa) as analyzed by Surface Plasmon Resonance (SPR).
Figure 17:
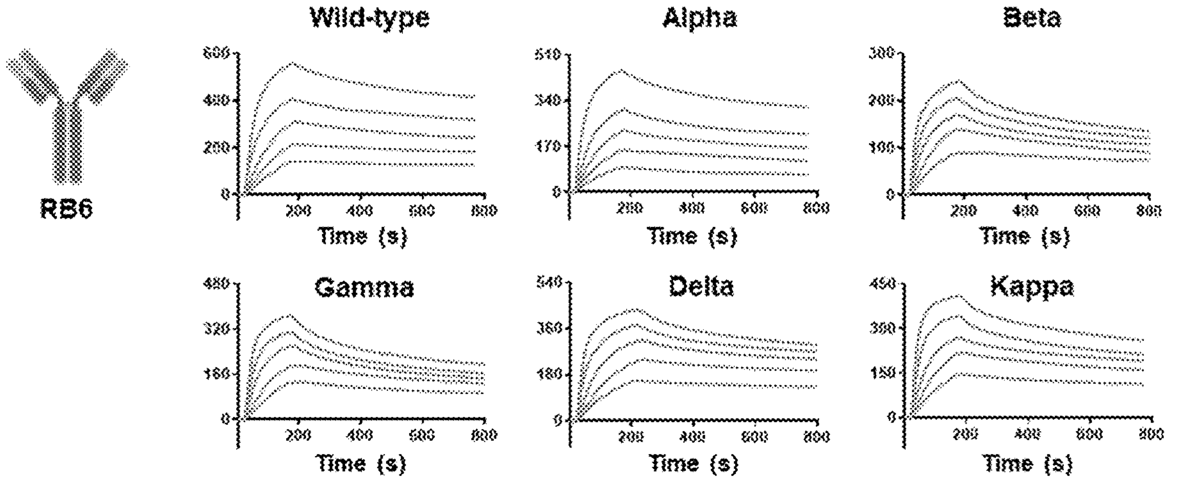
FIG. 17 shows views illustrating that the monoclonal antibody RB6 of the present disclosure has binding affinity for various recombinant SARS-CoV-2 RBDs (wild type, Alpha, Beta, Gamma, Delta, or Kappa) as analyzed by Surface Plasmon Resonance (SPR).

Example I-6: Surface Plasmon Resonance (SPR) Assay of Neutralizing Antibodies The binding kinetics of antibodies (RD3 and RB6) to SARS-CoV-2 RBD were analyzed at 25° C. on an iMSPR-mini instrument (iCLUEBIO, Seongnam, Republic of Korea) using 10 mM HEPES pH 7.4, 700 mM NaCl, 2 mM $CaCl_2$), 1 mM $MnCl_2$, and 0.005% (v/v) Tween-20 as a running buffer. The recombinant SARS-CoV-2 RBD (wild-type, Alpha, Beta, Gamma, Delta, or Kappa) was covalently immobilized on the surface of a COOH—Au chip (iCLUEBIO) up to 500 response units through standard amine coupling. The monoclonal antibodies (8, 16, 32, 64, and 128 nM) were injected onto the surface of a sensor chip at a flow rate of 50 μL/min. Curve fitting and data analysis were performed using the iMSPR analysis software (Tracedrawer; iCLUEBIO). The results are summarized in Tables 1 and 2 and depicted in FIGS. 16 and 17.

TABLE 1

| | RD3 | | |
|---|---|---|---|
| RBD types | $K_a$ ($10^5$ $M^{-1}$) | $K_d$ ($10^{-4}$ $M^{-1}S^{-1}$) | $K_D$ (nM) |
| Wild-type | 1.61 | 2.76 | 1.72 |
| Alpha (B.1.1.7) | 2.06 | 1.93 | 0.94 |
| Beta (B.1.351) | 0.93 | 2.95 | 3.18 |
| Gamma (P.1) | 0.70 | 3.15 | 4.51 |
| Delta (B.1.617.2) | 2.11 | 2.98 | 1.41 |
| Kappa (B.1.617.1) | 0.95 | 3.17 | 3.34 |

TABLE 2

| | RB6 | | |
|---|---|---|---|
| RBD types | $K_a$ ($10^5$ $M^{-1}$) | $K_d$ ($10^{-4}$ $M^{-1}S^{-1}$) | $K_D$ (nM) |
| Wild-type | 1.97 | 4.34 | 2.20 |
| Alpha (B.1.1.7) | 1.54 | 5.57 | 3.62 |
| Beta (B.1.351) | 4.92 | 7.88 | 1.6 |
| Gamma (P.1) | 4.54 | 9.39 | 2.07 |
| Delta (B.1.617.2) | 3.33 | 5.11 | 1.53 |
| Kappa (B.1.617.1) | 4.07 | 6.83 | 1.68 |

As understood from the data of Tables 1 and 2, the antibodies RD3 and RB6 of the present disclosure had high binding affinity for various types of SARS-CoV-2 RBD.

Example I-7: SARS-CoV-2 Pseudovirus Neutralization Assay

Pseudotyped replication-deficient lentiviral particles carrying the SARS-CoV-2 S protein of the wild-type or B.1 (D614G) variant, and a firefly luciferase reporter gene were prepared using Lenti-X™ SARS-CoV-2 packaging mix (Takara Bio, Kusatsu, Japan). Briefly, the packaging mix was transiently transfected into Expi293™ cells with Expi-Fectamine™ 293 reagent. After culturing for 72 hours, the supernatants containing the pseudotyped viruses were collected and centrifuged briefly (500×g for 10 min) to remove cellular debris. Virus titration was measured using Lenti-X GoStix™ Plus (Takara Bio) according to the manufacturer's instructions.

The pseudotyped replication-deficient Moloney murine leukemia virus (MLV) particles carrying the SARS-CoV-2 S protein of B.1.1.7 (alpha), B.1.617.2 (delta) or B.1.617 (kappa) variant, and a firefly luciferase reporter gene were obtained from eEnzyme (Gaithersburg, MD, USA).

To determine the neutralization activity of monoclonal antibodies on pseudotyped virus infection, $1\times10^4$ 293T/hACE2 cells in 50 μL culture medium were seeded in 96-well tissue culture plates overnight. Serial dilutions of the antibodies were pre-incubated at room temperature for 10 minutes with 50 μL of pseudotyped virus [$1\times10^7$ PFU/mL], and the mixture was subsequently incubated with the cells for 24 hours.

The firefly luciferase reporter gene expression (indicative of viral presence) was measured using ONE-Glo™ luciferase substrate (Promega, Madison, WI, USA). In brief, the culture medium was removed and incubated with 100 μl of ONE-Glo™ substrate. After 5 minutes, 70 μl supernatant was transferred to white flat-bottom 96-well assay plates (Corning; Lowell, MA, USA) and the luminescence signal was measured using the Synergy H1 microplate reader. The recorded relative luminescence units were normalized to those derived from cells infected with each SARS-CoV-2 pseudotyped virus in the absence of antibodies. Dose-response curves for IC50 values were determined using 4-parameter non-linear regression analysis (GraphPad Prism 8.0).

Figure 18:
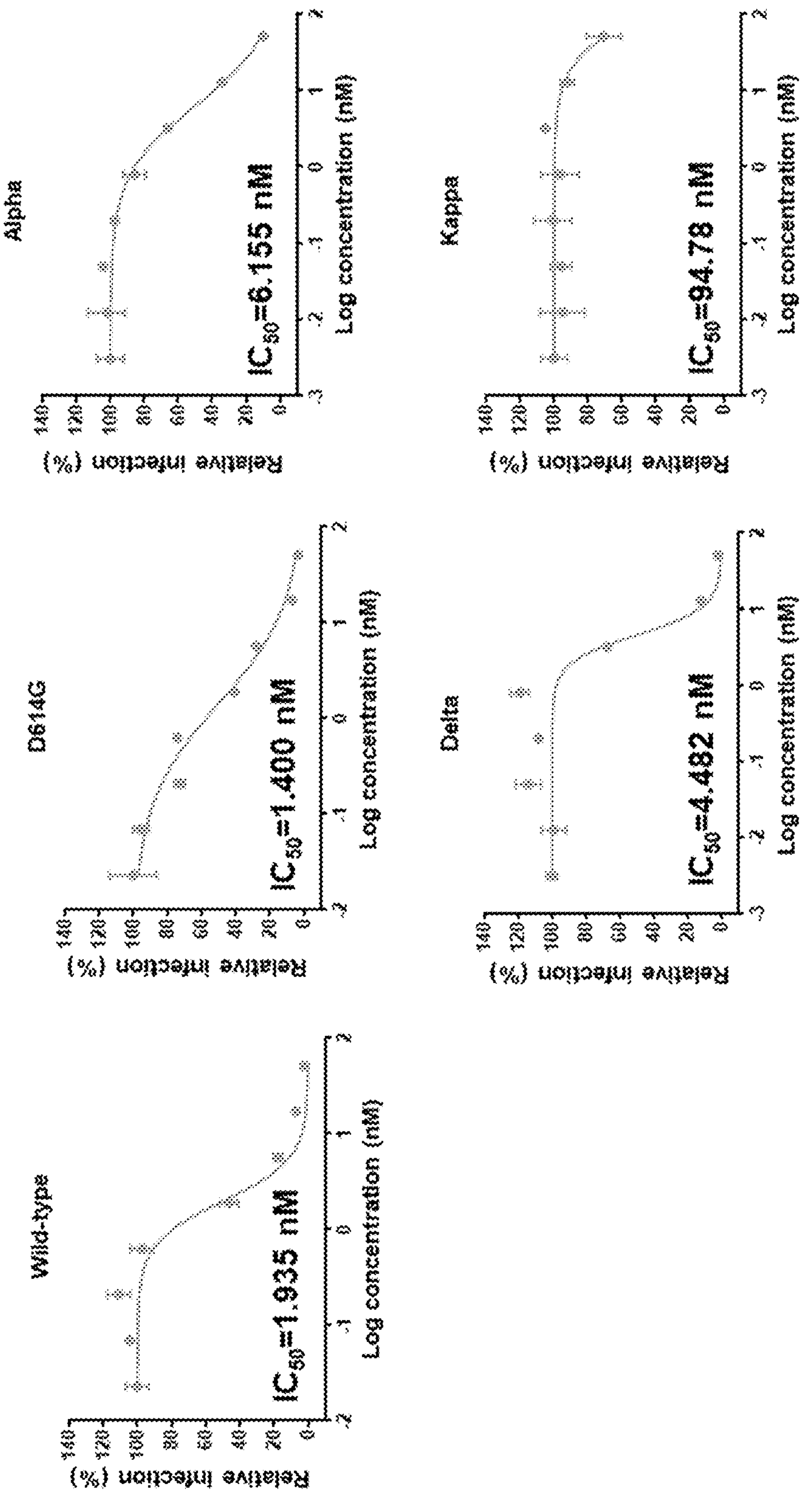
FIG. 18 shows plots of the neutralizing activity of the monoclonal antibody RD3 of the present disclosure against SARS-CoV-2 pseudovirus infection, with IC50 values given therein.

Results are summarized in Table 3 and depicted in FIG. 18.

TABLE 3

| Pseudovirus types | $IC_{50}$ (nM) RD3 |
|---|---|
| Wild-type | 1.94 ± 0.07 |
| D614G (B.1) | 1.40 ± 0.01 |

TABLE 3-continued

| Pseudovirus types | $IC_{50}$ (nM) RD3 |
|---|---|
| Alpha | 6.16 ± 0.08 |
| Delta | 4.48 ± 0.10 |
| Kappa | 94.78 ± 0.34 |

Example I-8: Preparation of True SARS-CoV-2 Virus

All experiments for true wild-type SARS-CoV-2 viruses were performed in a Biosafety Level 3 laboratory facility. A dilution of 40 μl of the patient sample in medium was inoculated into 150,000 VERO E6 cells in a 6-well plate. After 72 hours of infection, the supernatant was collected, centrifuged, and stored at −80° C. After two consecutive passages, RNA samples were prepared from the supernatant, and NGS confirmed that the clinical isolate was wild-type.

Example I-9: In Vivo Infection and Clinical Monitoring

All procedures for in vivo efficacy studies of monoclonal antibodies were approved by the Institutional Animal Care and Use Committee (IACUC) at KNOTUS (KNOTUS IACUC, Protocol Number: 22-KE-0076) and performed in a biosafety cabinet at the Biosafety Level 3 facilities. Female K18-hACE2 c57BL/6J mice 8-10 weeks old were obtained from the Jackson Laboratory (Bar Harbor, ME, USA) and housed in a specific pathogen-free condition and allowed to freely access foods and water. They were randomly assigned into experimental groups.

Figure 19:
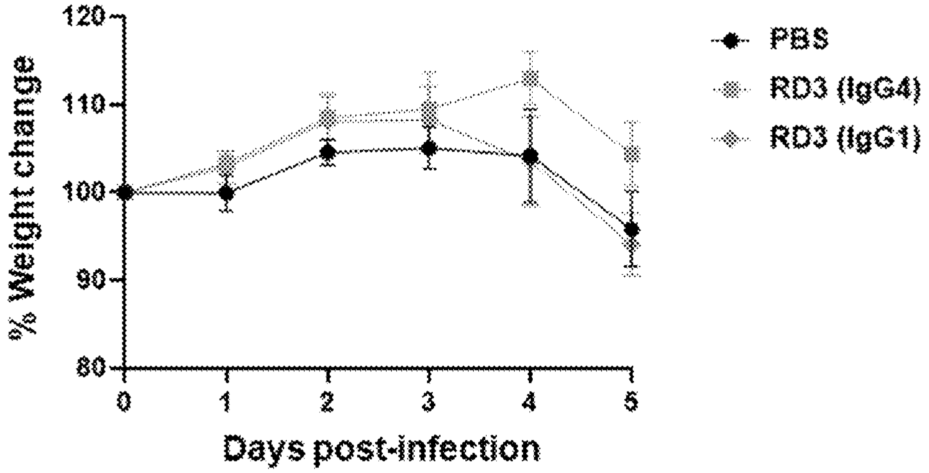
FIGS. 19 and 20 are plots of the weight change (FIG. 19) and clinical severity (FIG. 20) when the monoclonal antibody RD3 of the present disclosure was administered to mice infected with the wild-type SARS-CoV-2 virus.

The mice (n=7/group) were anesthetized by isoflurane inhalation and intranasally inoculated with $10^4$ PFU wild-type SARS-CoV-2 in 30 μL of PBS. After viral infection, the monoclonal antibody IgG1 or IgG4 was intravenously injected once (+3h) at a dose of 30 mg/kg. After infection, the mice were monitored for weight change and the results are depicted in FIG. 19.

Figure 20:
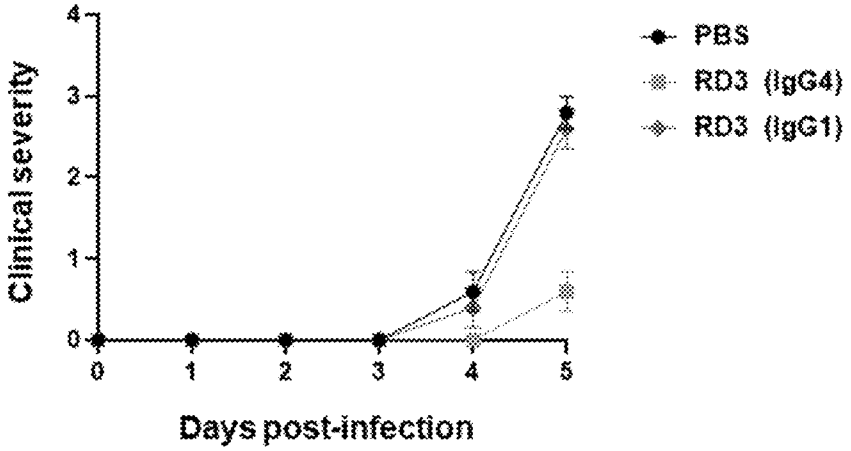

In addition, clinical severity was scored according to the criteria of Table 4, below, and the results are depicted in FIG. 20.

TABLE 4

| Score | Description | Appearance & Mobility |
|---|---|---|
| 0 | Healthy | No observable sign of disease |
| 1 | Slightly ruffled | Slightly ruffled coat |
| 2 | Ruffled | Ruffled coat throughout the body and a wet appearance |
| 3 | Sick | Very ruffled coat and slightly closed, inset eyes |
| 4 | Very sick | Very ruffled coat; closed, inset eyes; and moribund state |

As shown in FIG. 19, the IgG4-typee RD3 monoclonal antibody-administered group experienced less weight loss compared to the PBS-administered group, confirming its effect in alleviating clinical severity. Also, as illustrated in FIG. 20, the clinical severity appeared relatively lower in the RD3 (IgG4)-administered group compared to the PBS- or RD3 (IgG1)-administered groups. From these results, it was evident that the RD3 monoclonal antibody of the present disclosure is more efficacious in its IgG4 form.

EXAMPLE II

Figure 21:
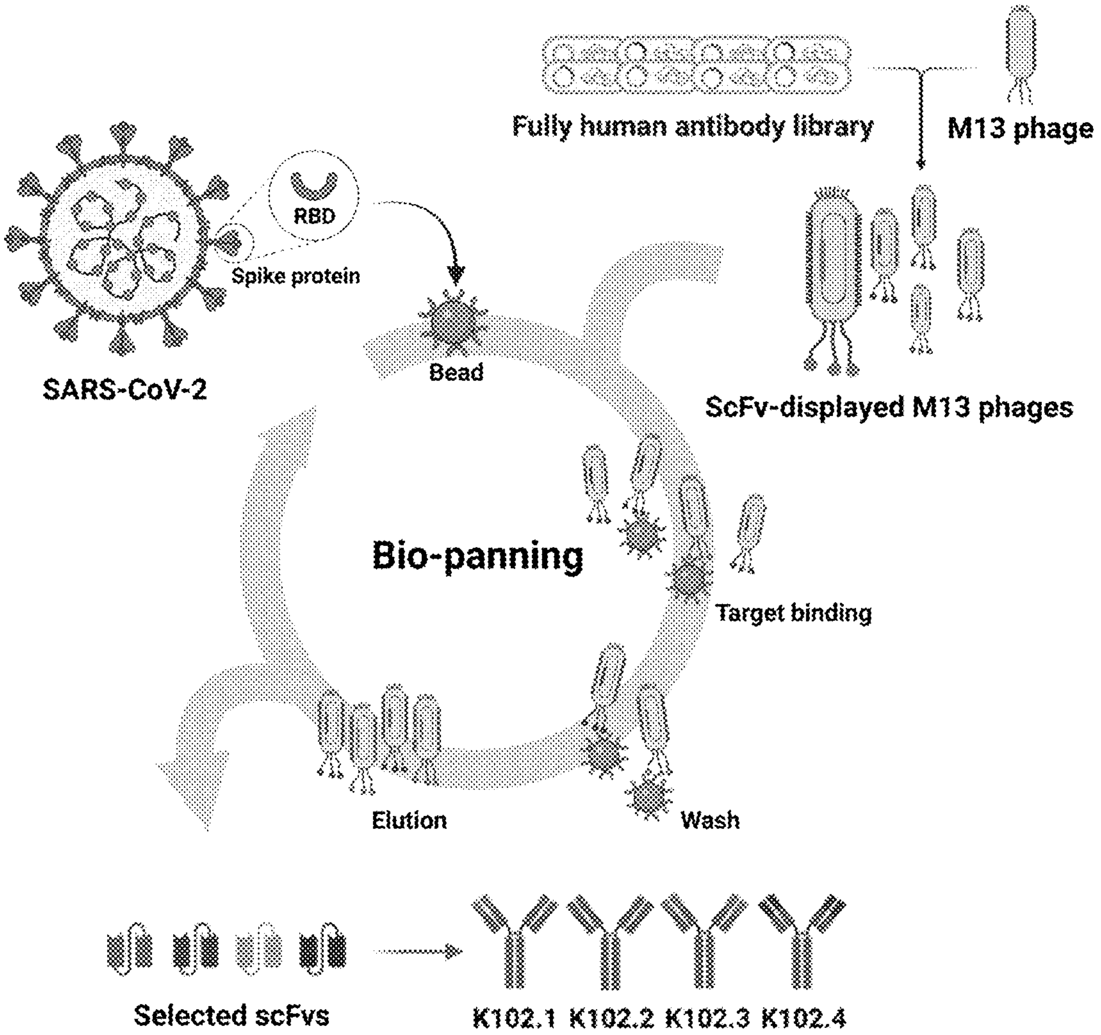
FIG. 21 is a schematic view illustrating a process of selecting SARS-CoV-2 virus RBD-specific human antibody from an scFv library through a phage display technology.

Example II-1. Isolation of Human Antibody Specific for RBD Antigen of SARS-CoV-2 Virus by Using Phage Display Technology Selection was made of SARS-CoV-2 RBD antigen-specific human antibodies from the human synthetic single-chain variable fragment (scFv) antibody library. As illustrated in FIG. 21, a selection process using phage display technology was carried out.

First, SARS-CoV-2 RBD antigen-specific scFv clones were selected through five rounds of bio-panning using magnetic beads Dynabeads M-270 epoxy, Invitrogen) coated with 4 μg of the recombinant SARS-CoV-2 RBD antigen.

Figure 22:
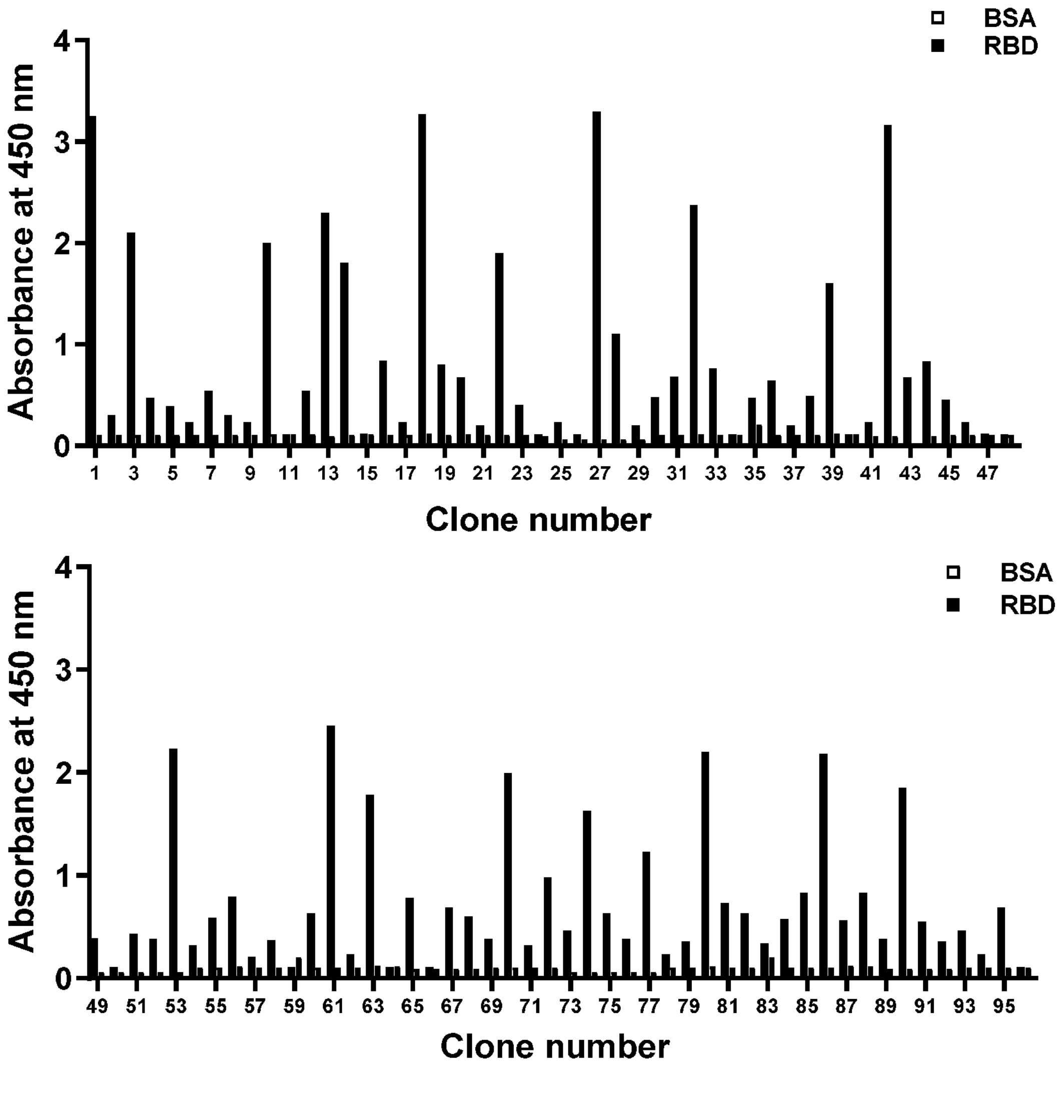
FIG. 22 shows results of phage ELISA for scFv binding to RBD to select human antibodies specific for the RBD antigen of SARS-CoV-2 virus.

Then, 96 clones were randomly selected from output colonies formed on plates and tested for their reactivity to the SARS-CoV-2 RBD antigen by phase ELISA to pick out human antibody clones that are highly reactive to and specific for the corresponding antigen. Results of the phase ELISA are depicted in FIG. 22.

Example II-2. IgG Conversion, Production, and Purification of Selected Antibodies 2.1. SARS-CoV-2 RBD Antigen-Specific scFv Antibody Conversion to IgG Heavy and light chains of four types of the selected RBD-specific scFv antibodies were amplified by PCR to obtain respective insert DNAs which were then cloned into mammalian expression vector pcDNA3.1 for production of IgG antibodies. Each recombinant DNA of the four types of scFvs was overproduced with high purity in Expi293 cell using a Maxi-prep kit. The purity of DNA was measured using nanodrop 2000 spectrophotometer (Thermo Fisher Scientific).

2.2. Mass Production and Purification of RBD-Specific IgG Antibodies

Transient expression was performed using the Expi293 system (Invitrogen). In this regard, the four types of IgG antibodies were transfected into Expi293 cells with the ExpiFectamine 293 transfection kit (Gibco) and then incubated for five days. Following centrifugation of the cell culture, the cell pellet was removed. The antibodies were purified from the supernatant (medium).

The purification of the selected antibodies was conducted by affinity chromatography using protein A sepharose bead (Repligen, Waltha, MA, USA).

Example II-3. Physicochemical Characterization of Selected Antibodies

:Assay of Selected Antibody for Purity and Molecular Weight

Figure 23:
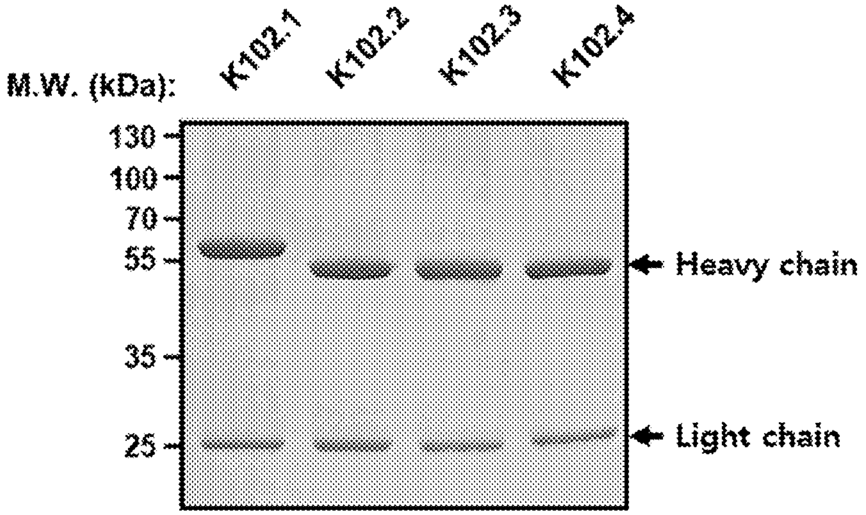
FIG. 23 is an image of SDS-PAGE for four selected IgG antibodies specific for SARS-CoV-2 RBD.

The four SARS-CoV-2 RBD-specific antibodies (K102.1, K102.2, K102.3, and K102.4) were loaded in the same amount onto a polyacrylamide gel and resolved by SDS-PAGE. From Coomassie Brilliant Blue staining, it was observed that each of the four antibodies had a final purity of 90% or higher and molecular weights of approximately 50 kDa for the heavy chain and 25 kDa for the light chain (FIG. 23).

Figure 24:
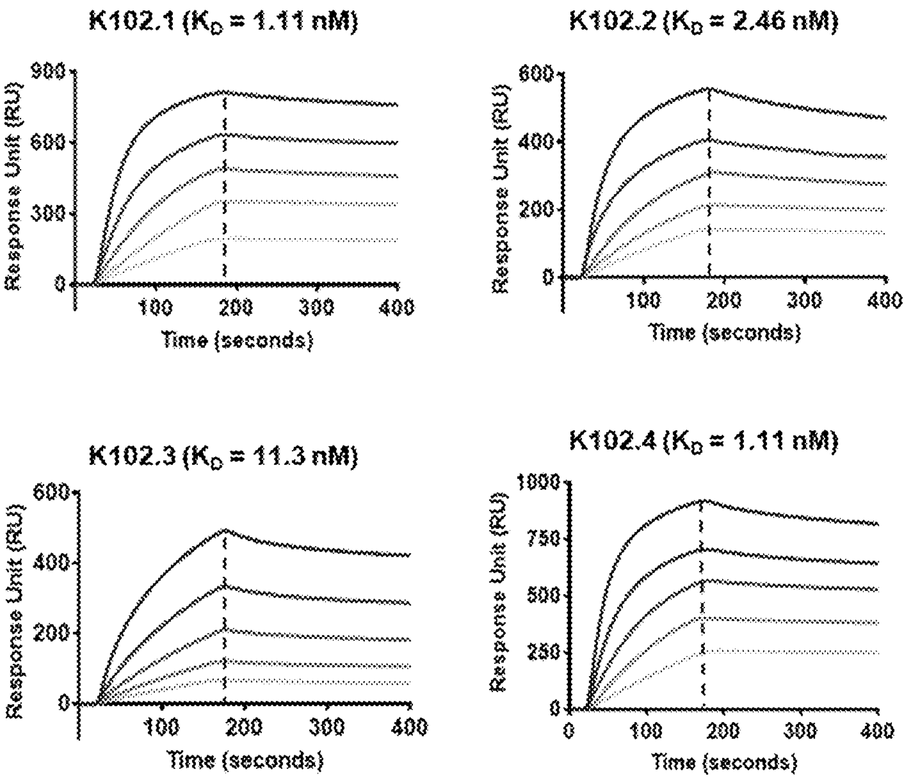
FIG. 24 shows KD values of four selected SARS-CoV-2 RBD-specific IgG antibodies to SARS-CoV-2 RBD antigens as measured by Surface Plasmon Resonance (SPR).

In addition, the binding affinity ($K_D$) of the selected antibodies was observed to be $1.643\times10^{-9}$ M for K102.1 and $2.465\times10^{-9}$ M for K102.2 (FIG. 24).

Example II-4. Selection of Monoclonal Antibody Pair Binding to Different Epitopes of SARS-CoV-2 RBD 4.1. Conjugation of Marker to Selected Antibody (K102.1)

For use as a detection antibody in sandwich ELISA, the antibody K102.1 produced in Example 2 was conjugated with the marker HRP (horseradish peroxidase), using EZ-Link™ Plus Activated Peroxidase Kit (Thermo Fisher Scientific) according to the manufacturer's instructions.

4.2. Selection of Antibody Pair Recognizing Different Epitopes of SARS-CoV-2 RBD To select an antibody pair recognizing different epitopes of SARS-CoV-2 RBD from the selected SARS-CoV-2 RBD-specific antibody group, the four selected antibodies were subjected to competition ELISA with the HRP-conjugated antibody (K102.1-HRP).

Figure 25:
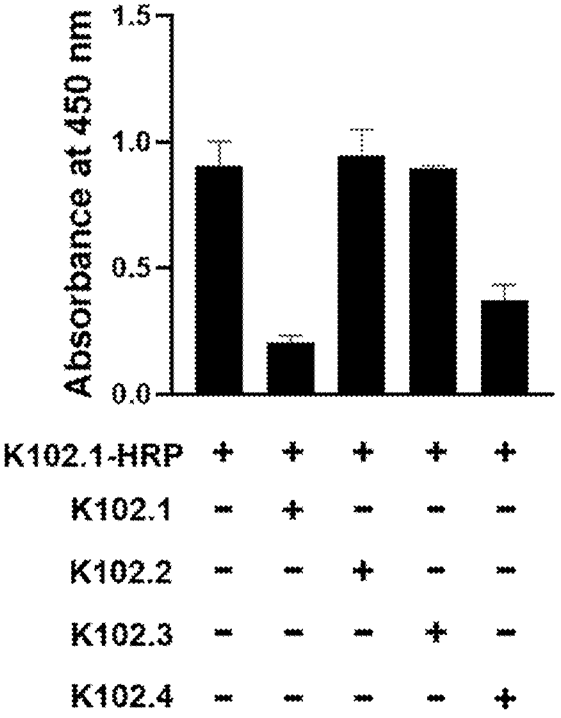
FIG. 25 shows competition ELISA results between K102.1-HRP and four selected SARS-CoV-2 RBD-specific IgG antibodies to select pairs of antibodies for sandwich ELISA.

The results are depicted in FIG. 25. As shown, K102.1 was observed to have a distinct binding site to the SARS-CoV-2 RBD compared to K102.2 and K102.3. Also, based on the SPR analysis, as shown in FIG. 24, K102.2 exhibited about 5 times higher affinity for the SARS-CoV-2 RBD than K102.3.

Therefore, K102.1 and K102.2 were selected as a pair of antibodies that can be utilized for the development of Sandwich ELISA.

Example II-5. Analysis of Selected Pair for Sandwich ELISA 5.1. Assay for Suitability of Selected Antibody Pair The selected antibody pair (K102.1 and K102.2) determined in Example 4 was evaluated for suitability for use in the sandwich ELISA of the present disclosure by verifying pairing therebetween. The sandwich ELISA was performed using K102.1 or K102.2 as the capture antibody and K102.1-HA or K102.2-HA as the detection antibody.

Figure 26:
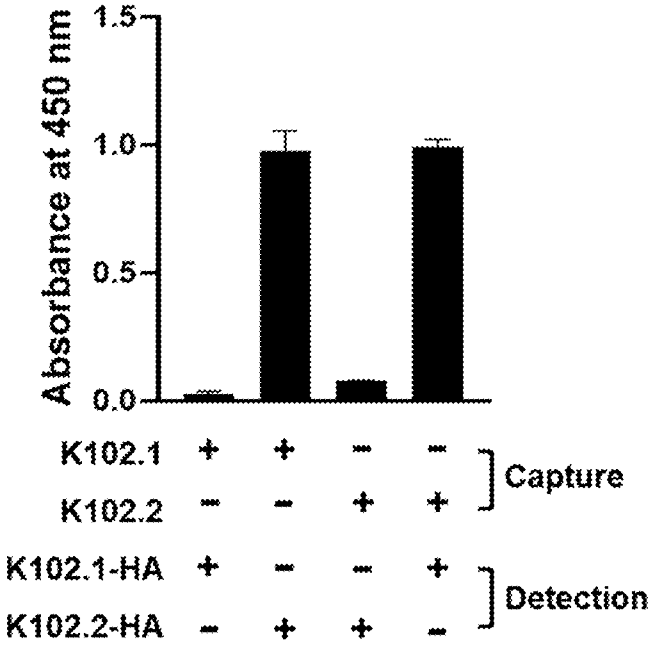
FIG. 26 shows sandwich ELISA results to identify the pairing in the selected antibodies of the present disclosure.

As shown in FIG. 26, it was confirmed that K102.1 and K102.2 can be paired as either the capture antibody or the detection antibody for the Sandwich ELISA.

5.2. Verification of Distinct Epitopes of SARS-CoV-2 RBD for Selected Antibody Pair Furthermore, SPR (Surface Plasmon Resonance)-based competition binding assay was performed to determine whether the selected antibody pair bind to distinct epitopes on the SARS-CoV-2 RBD. By measuring real-time binding of the selected antibodies to the SARS-CoV-2 RBD an iMSPR mini-instrument (icluebio, South Korea), the competition binding assay was used to evaluate whether K102.1 or K102.2-HA possess unique or overlapping binding sites.

In brief, 128 nM K102.1 in a HEPES buffered Steinberg's solution containing 0.005% (v/v) Tween-20. was injected onto the SARS-CoV-2 RBD surface (ca. 1,000 RU) at a flow rate of 50 μl/min for 240 seconds. Subsequently, 128 nM K102.2-HA was introduced under the same conditions onto the surface where K102.1 and SARS-CoV-2 RBD were bound. The resulting curves were obtained as sensorgrams using the iMSPR analysis software.

Figure 27:
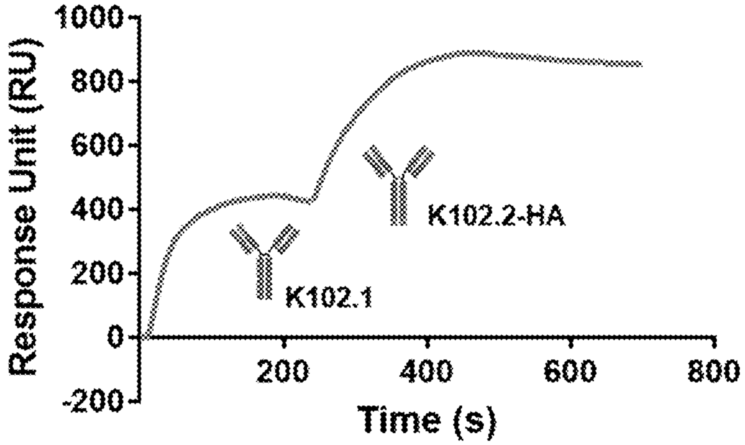
FIG. 27 shows SPR-based competition binding assay results to determine the presence or absence of different epitopes for the selected antibody pair of the present disclosure.

As shown in FIG. 27, it was confirmed that K102.1 has a distinct epitope from K102.2 for the SARS-CoV-2 RBD.

Example II-6. Development of Sandwich ELISA Method Using Selected Antibody Pair

Figure 28:
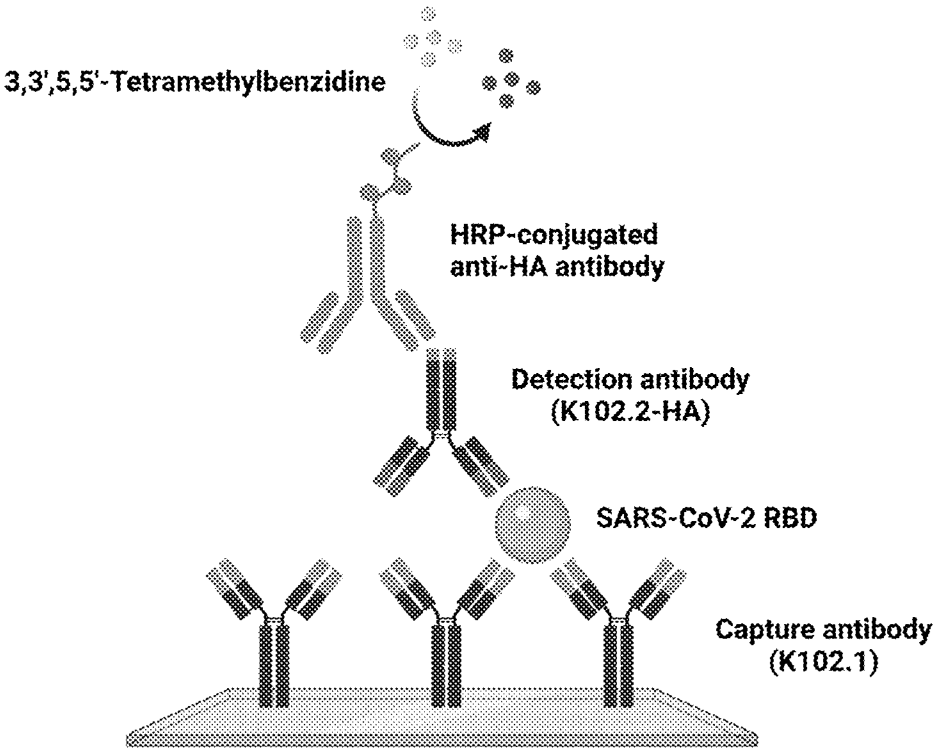
FIG. 28 is a schematic representation of sandwich ELISA using a selected antibody pair specific for SARS-CoV-2 RBD antigen.

A Sandwich ELISA method for detecting SARS-CoV-2 was developed using the SARS-CoV-2 specific monoclonal antibodies K102.1 (capture antibody) and K102.2 (detection antibody). The sandwich ELISA method of the present disclosure is schematically illustrated in FIG. 28.

6.1. Optimization of Conditions for Sandwich ELISA 6.1.1. Optimal Concentration of Selected Antibody Pair To determine the optimal conditions therefor, sandwich ELISA was carried out with increasing concentrations of either the capture antibody or the detection antibody.

Figure 29:
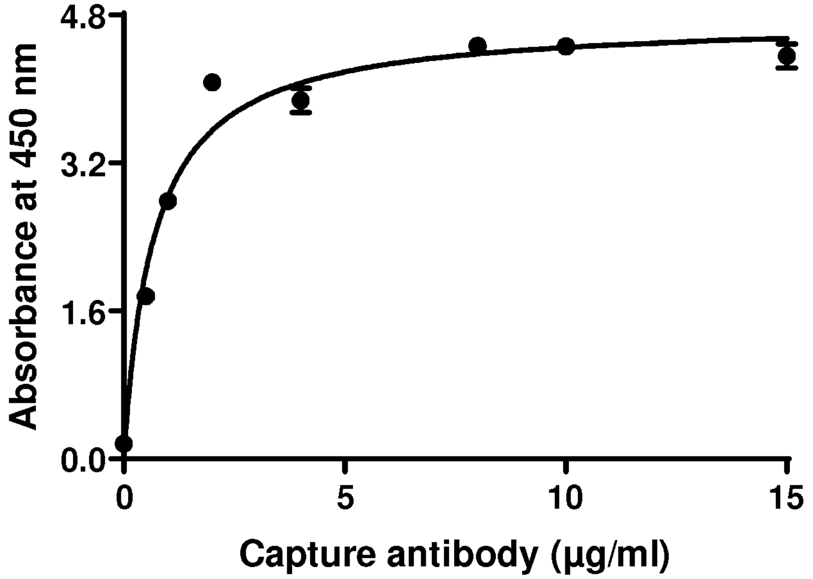
FIG. 29 is a plot showing the optimization of concentration for the capture antibody of the selected antibody pair for sandwich ELISA.
Figure 30:
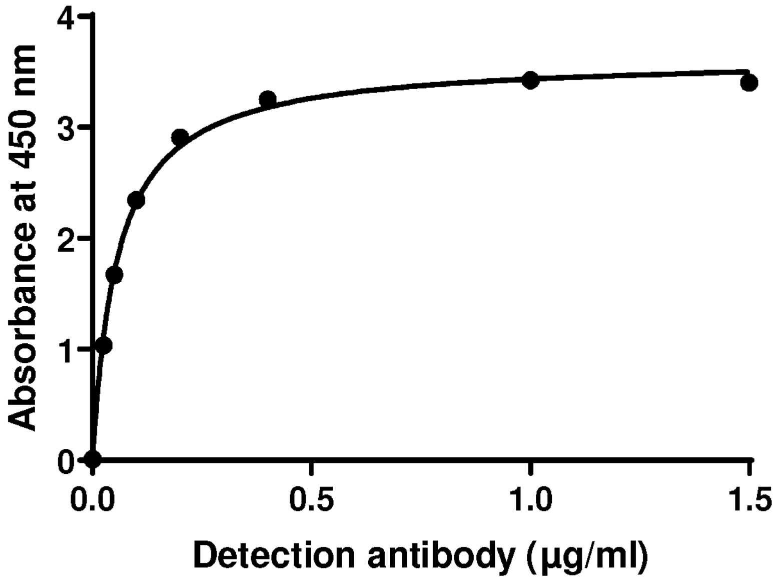
FIG. 30 is a plot showing the optimization of concentration for the detection antibody of the selected antibody pair for sandwich ELISA.

As a result, it was confirmed that 5 μg/ml of the capture antibody (K102.1) and 1 μg/ml of the detection antibody (K102.2-HA) are optimal concentrations for sandwich ELISA method (FIGS. 29 and 30).

6.1.2. Calibration Curve for Limit of Detection (LOD)

Figure 31:
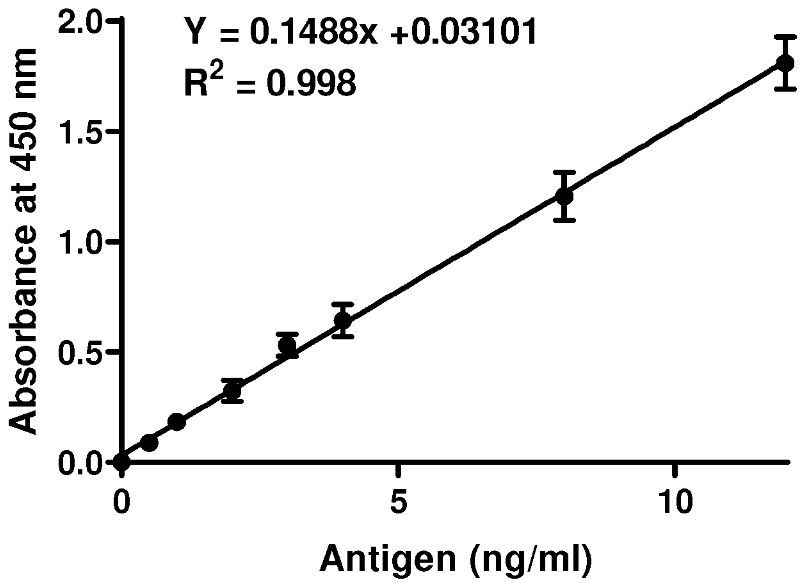
FIG. 31 is a calibration curve for determining the limit of detection (LOD) of SARS-CoV-2 RBD.

A calibration curve was derived to determine the limit of detection of SARS-CoV-2 RBD in the sandwich ELISA of the present disclosure. The reproducibility of the calibration curve was validated through six independent analyses, and the linear dynamic range of the derived calibration curve was determined to be between 0 ng/ml and 12 ng/ml (equivalent to 0 pM to 480 pM) for the SARS-CoV-2 RBD (FIG. 31).

The limit of detection (LOD) for the sandwich ELISA of the present disclosure was derived by calculating the standard deviation (SD) and slope(S) of the calibration curve according to Equation 1. The determined LOD was found to be 0.55 ng/ml (equivalent to 22 pM).

Limit of Detection (LOD)=3×(standard deviation (SD)/slope(S) of calibration curve) [Equation 1]

In addition, the sensitivity was derived by calculating standard deviation (SD) and mean of the blank according to the following Equation 2. The sensitivity was determined to be 0.48 ng/ml (19.2 pM).

Sensitivity)=3×standard deviation (SD)+mean of blank [Equation 2]

Table 5 shows a comparison of the performance of the Sandwich ELISA of the present disclosure with two types of Sandwich ELISA kits previously developed and sold on the market.

TABLE 5

| Company | Trade Name | Cat. No. | Sensitivity | Source |
|---|---|---|---|---|
| Eaglebio | GENLISATM SARS-CoV-2 (2019-nCoV) Spike RBD Antigen Quantitative ELISA | KBVH015-12 | 12 ng/ml | https://eaglebio.com/wp-content/uploads/2021/06/KBVH015-12-SARS-CoV-2-Spike-RBD-Antigen-Quantitative-ELISA-Package-Insert.pdf |

TABLE 5-continued

| Company | Trade Name | Cat. No. | Sensitivity | Source |
|---|---|---|---|---|
| Biozol | SARS-CoV-2 Spike S1 Protein ELISA Kit | ACM-55030 | 0.58 ng/ml | https://www.biozol.de/en/product/acm-55030 |

From the data of Table 5, it is understood that the kit of the present disclosure with a sensitivity of 48 ng/ml (19.2 pM) is superior in terms of sensitivity to the previously approved and commercially available kits with respective sensitivities of 12 ng/ml (Eaglebio) and 0.58 ng/ml (Biozol).

6.2. Validation of Sandwich ELISA:

Measurement of Coefficient of Variation (CV) and Recovery

To validate the Sandwich ELISA method developed using the selected antibody pair of the present disclosure, the coefficient of variation (CV) and recovery were measured by performing both intra- and inter-assays. Intra-assay precision was determined by measuring samples six times in triplicate within the same assay run. Inter-assay precision was determined by measuring a sample in triplicate in six separate assay runs.

The mean and standard deviation (SD) was calculated. The coefficient of variation (CV) was calculated according to the following equation 3:

$$CV\ (\%)=(SD/mean)\times 100. \quad \text{[Equation 3]}$$

Recovery was calculated according to the following equation 4:

$$Recovery\ (\%)=\text{Average measured concentration/expected concentration]}\times 100 \quad \text{[Equation 4]}$$

As shown in FIG. 32, the intra- and inter-assay CVs for 5 ng/ml SARS-CoV-2 RBD were 8.46% and 9.52%, respectively. The intra- and inter-assay recoveries for 5 ng/ml SARS-CoV-2 RBD were 105.57% and 98.56%, respectively.

Therefore, it was confirmed that the sandwich ELISA method of the present disclosure is a sensitive, accurate, and reliable technique for detecting SARS-CoV-2 RBD.

Example II-7. Analysis for Performance of Sandwich ELISA

:Ability of Sandwich ELISA to Detect Eight RBD Mutants

The optimized sandwich ELISA method of the present disclosure was evaluated for ability to detect SARS-CoV-2 RBD mutants.

Regarding SARS-CoV-2, representative RBD mutants categorized by countries worldwide were secured, comprising eight types: A435S (Finland), N354D (China), G476S and V483A (USA), F342L, V341I, and N501Y (UK), and L452R/T478K (India). The Sandwich ELISA was performed in the presence of increasing concentrations of these antigens to 32 pM, 96 pM, and 200 pM.

Briefly, 96-well high-binding microplates (Corning) were coated with the capture antibody K102.1 and then blocked using 3% (w/v) bovine serum albumin (BSA) in PBS for 2 hours at 37° C. Next, 100 μL of increasing concentrations of the RBDs of wild-type SARS-CoV-2 mutants (A435S, N354D, G476S, V483A, F342L, V341I, N501Y, and L452R/T478K) were added to each well, and the microplates were incubated for 3 hours at 37° C. The plates were washed thrice with 0.05% (v/v) PBST and incubated with the detection antibody HA-tagged K102.2 (K102.2-HA). Subsequently, the plates were washed thrice with 0.05% (v/v) PBST and incubated with HRP-conjugated anti-HA antibody to detect K102.2-HA. To this end, the plates were washed thrice and a TMB substrate solution (Thermo Fisher Scientific) was added to each well, followed by reaction with HRP for 15 minutes. The reaction was terminated by adding 1 M $H_2SO_4$. (100 100 μL/well). The absorbance of each sample was read at 450 nm on a microplate reader.

Figure 33:
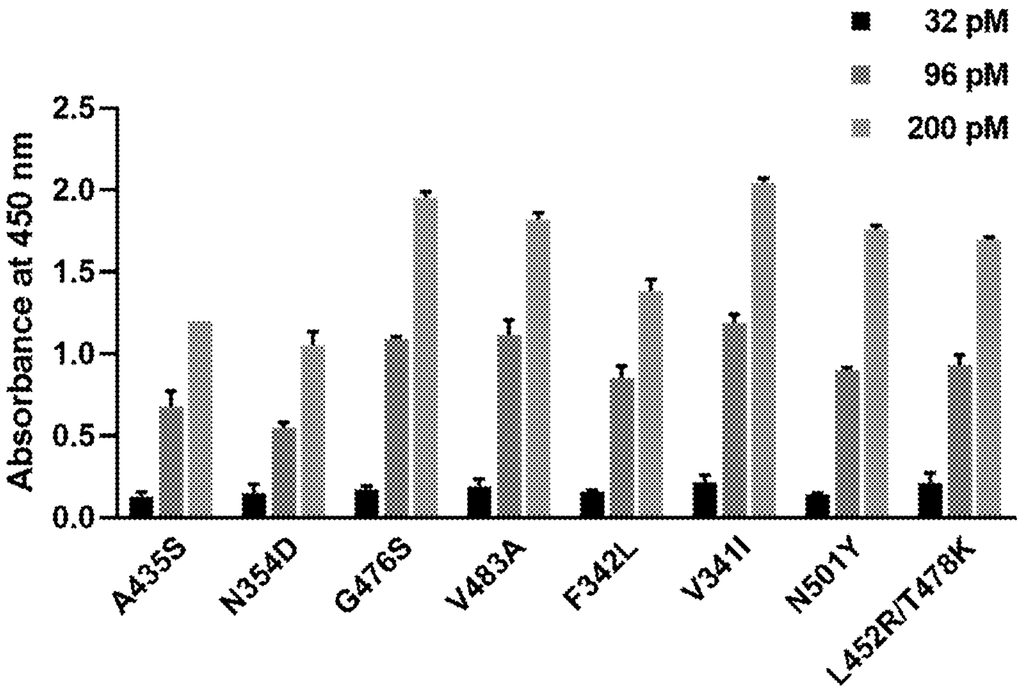
FIG. 33 is a graph showing the ability of optimized sandwich ELISA to detect eight types of SARS-CoV-2 RBD variants according to concentration.

Consequently, as shown in FIG. 33, the optimized sandwich ELISA method of the present disclosure can detect all the eight RBD mutant protein antigens in the picomolar range.

EXAMPLE III

Example III-1: Design, Generation, and Characterization of bsAbs

Figure 34:
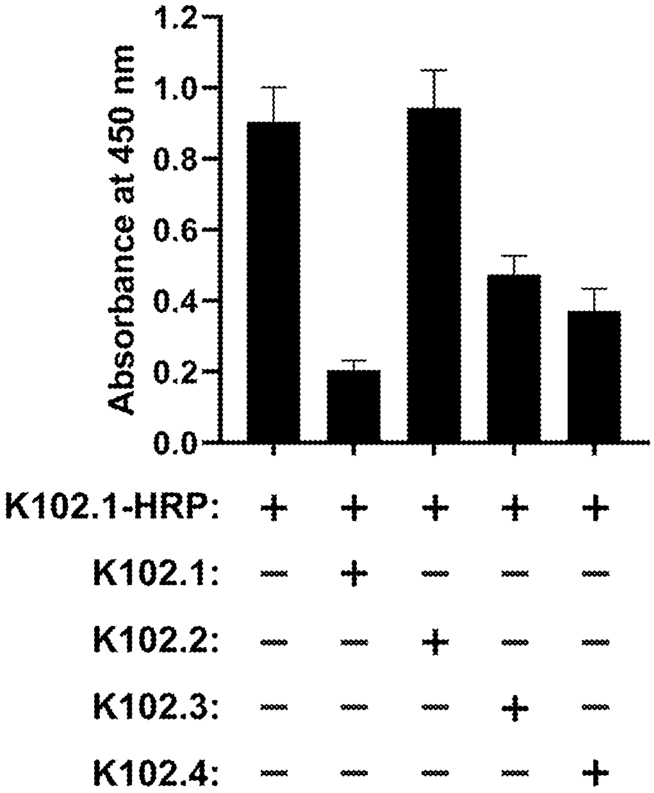
FIG. 34 is a graph showing results of competition ELISA conducted to identify the recognition of respective independent SARS-CoV-2 RBD epitopes by the separate antibodies.

Four SARS-CoV-2 RBD-specific human scFvs with a complementarity determining region (CDR) sequence were isolated using phage-display technology from the human synthetic scFv library. To prevent Fab arm exchange that results in an unwanted heterogeneous mixture of antibodies by half molecule exchanged with endogenous IgG4, IgG4-based mAbs with S228P mutations [IgG4 (S228P)] were constructed. Among the antibodies, a noncompeting pair of mAbs, K102.1 and K102.2, which recognize independent epitopes of the SARS-CoV-2 RBD, was identified using a competition ELISA (FIG. 34).

Figure 35:
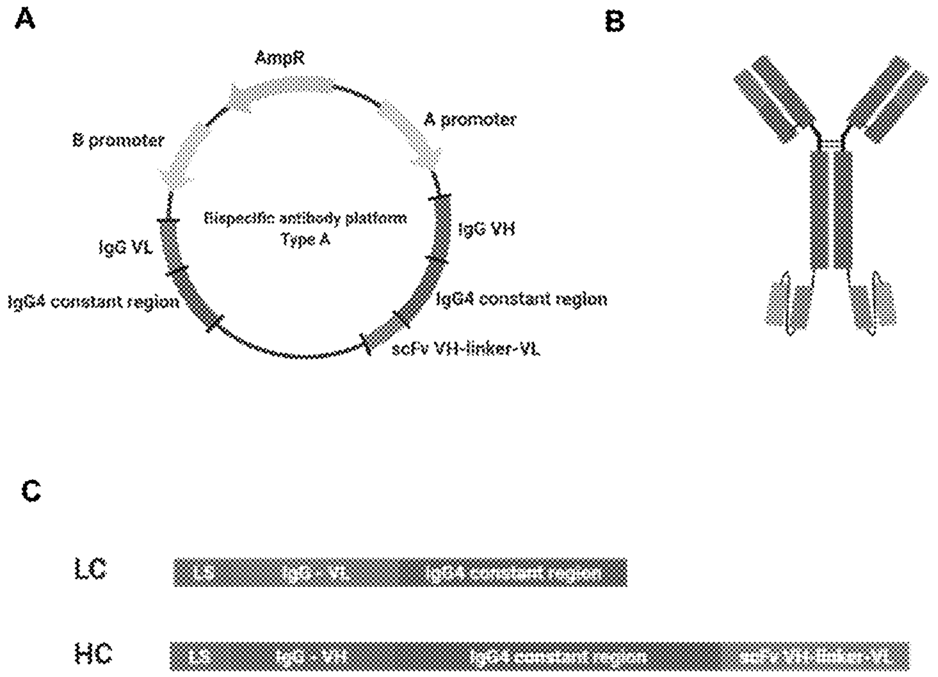
FIGS. 35, 36 and 37 are schematic views showing structures of the three types of bispecific antibodies capable of being fabricated with the antibodies K102.1 and K102.2 of the present disclosure and vector structures adapting for expressing same.
Figure 36:
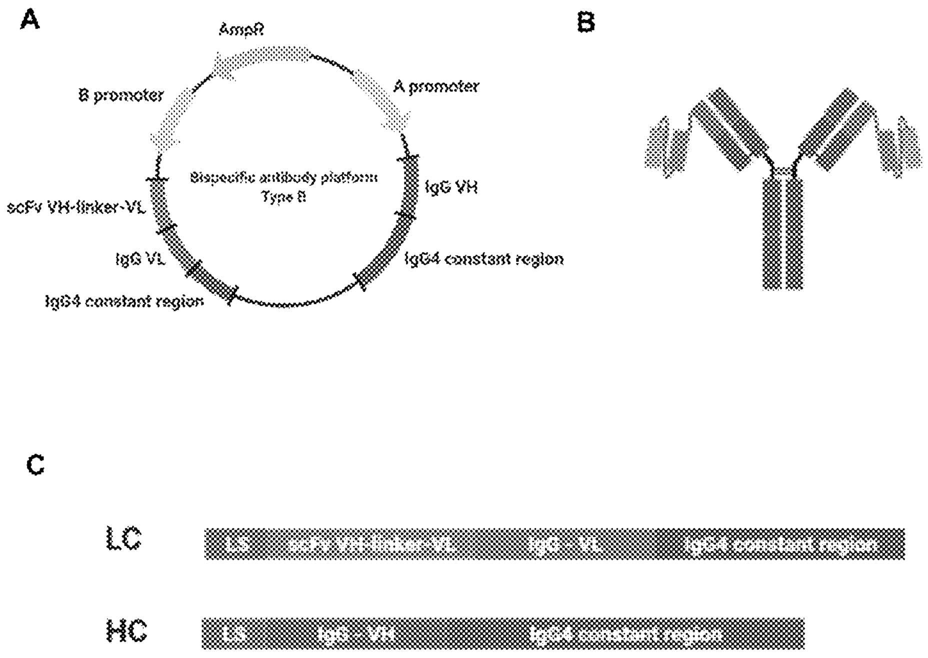
Figure 37:
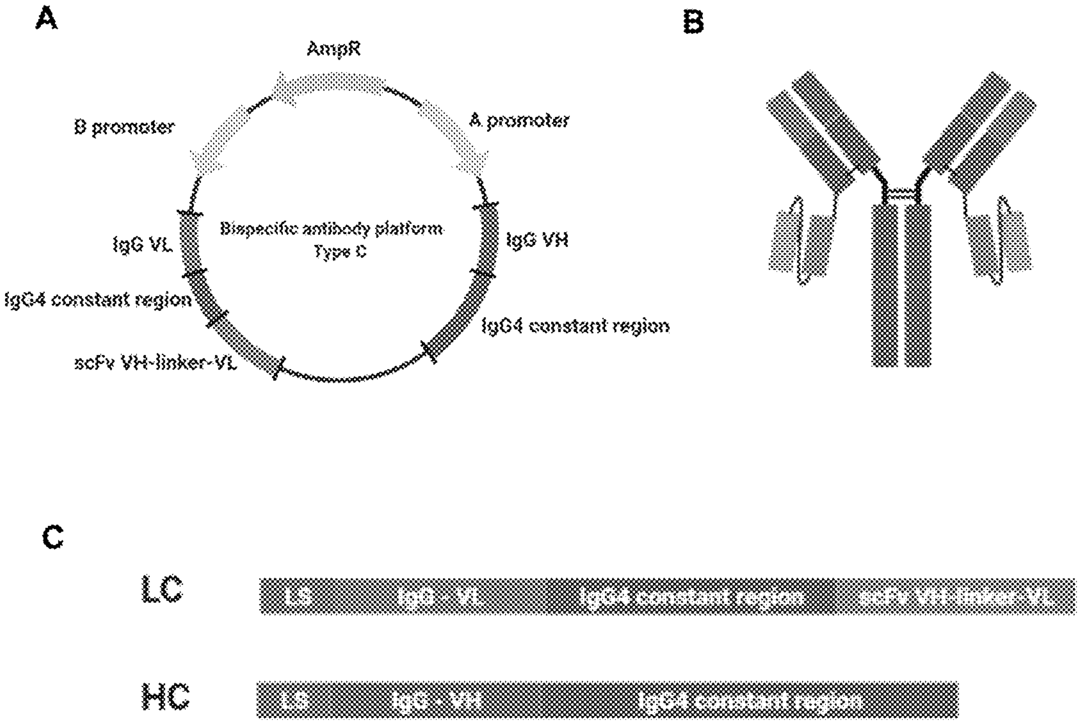
Figure 38:
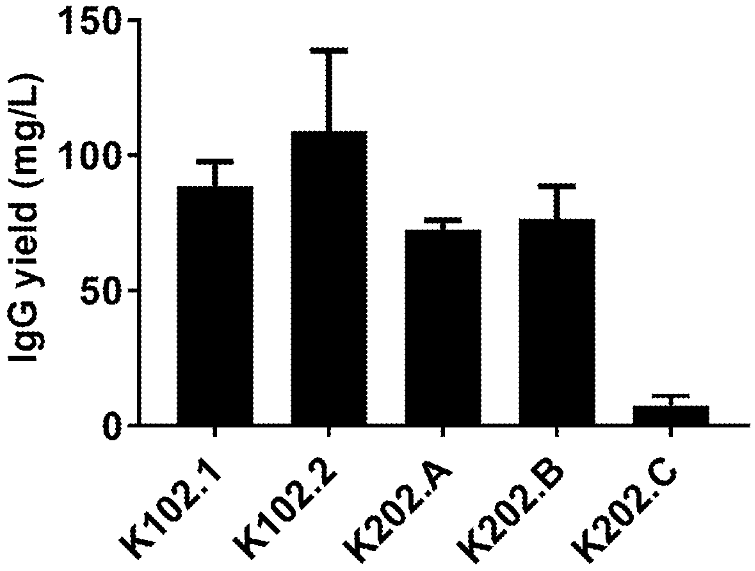
FIG. 38 is a graph showing expression levels of the antibodies (K102.1 and K102.2) and bispecific antibodies (K202.A, K202.B, and K202.C) of the present disclosure.

Based on these parental mAbs, three forms of IgG4 (S228P)-(scFv) 2 bispecific antibody (bsAb), such as structures of K202.A (FIG. 35), K202.B (FIG. 36), and K202.C (FIG. 37), were designed. As a result of expressing the three forms of the bispecific antibodies, the K202.C bispecific antibody was expressed at a significantly poor rate (FIG. 38).

Figure 39:
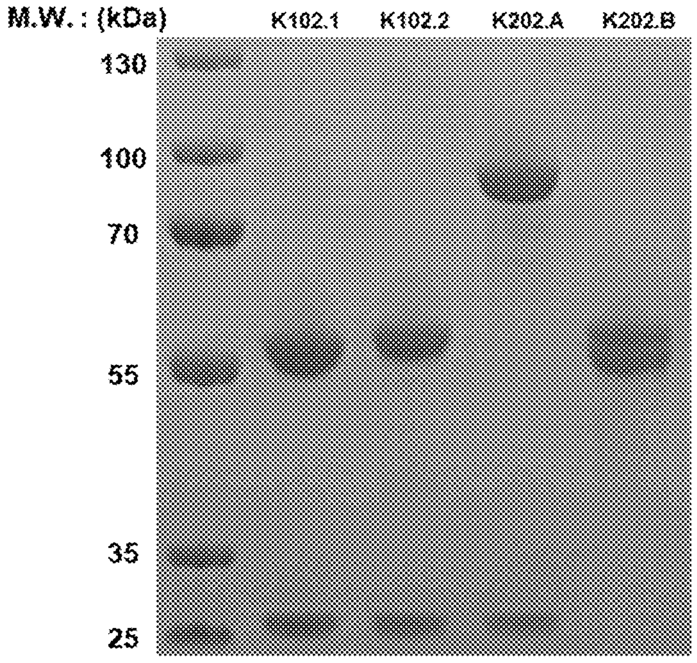
FIG. 39 is an image of western blots showing expression of the antibodies (K102.1 and K102.2) and bispecific antibodies (K202.A, K202.B, and K202.C) of the present disclosure with high purity.
Figure 40A:
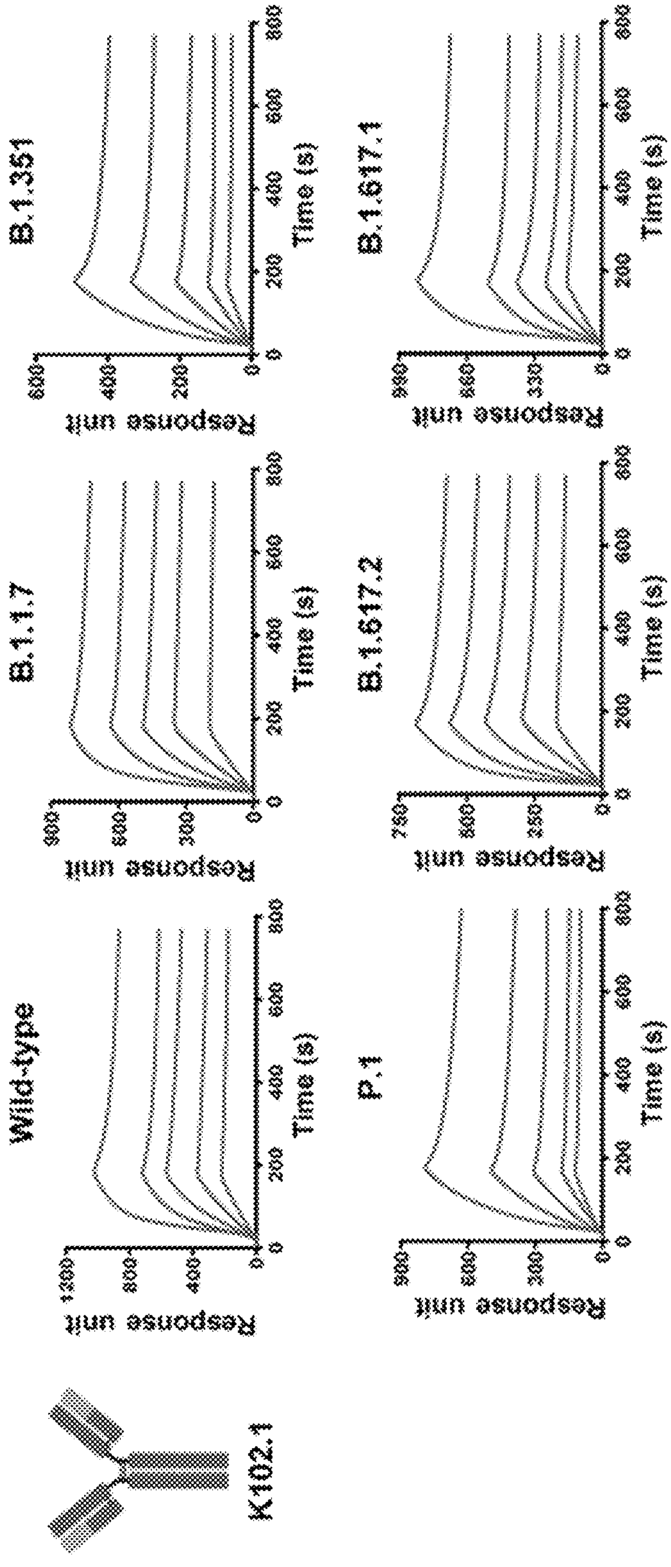
FIGS. 40*a*, 40*b*, 40*c* and 40*d* show the binding affinity of the antibodies and bispecific antibodies of the present disclosure for wild-type SARS-CoV-2 and alpha, beta, gamma, delta, and kappa variants thereof as measured by SPR analysis.
Figure 40B:
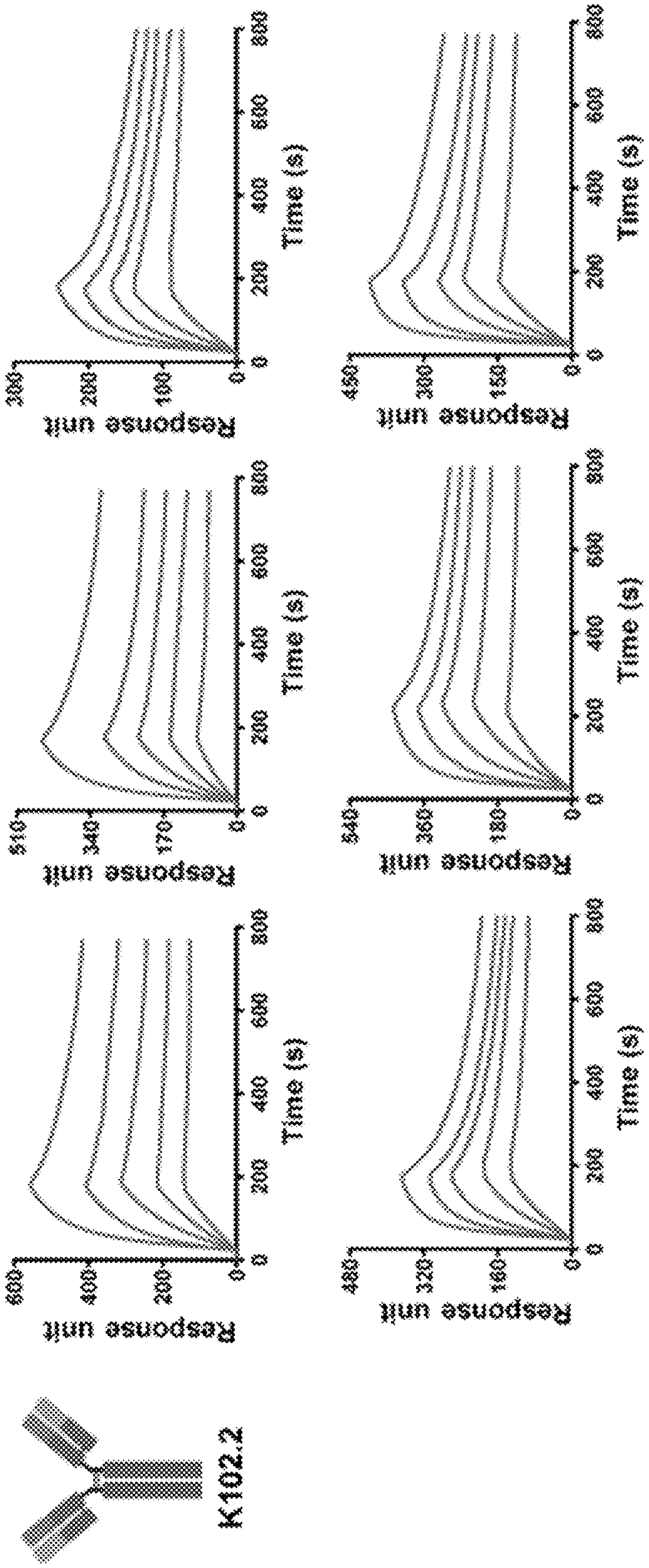
Figure 40C:
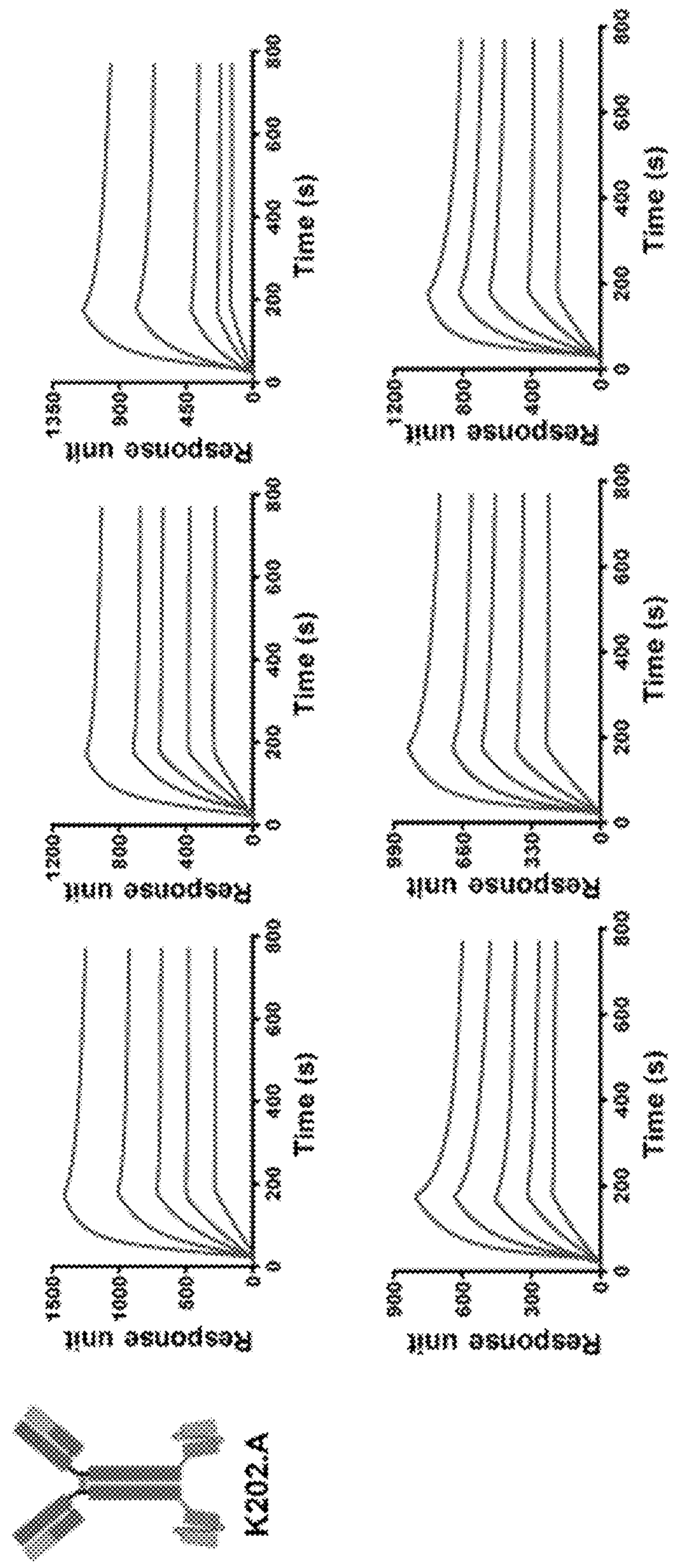
Figure 40D:
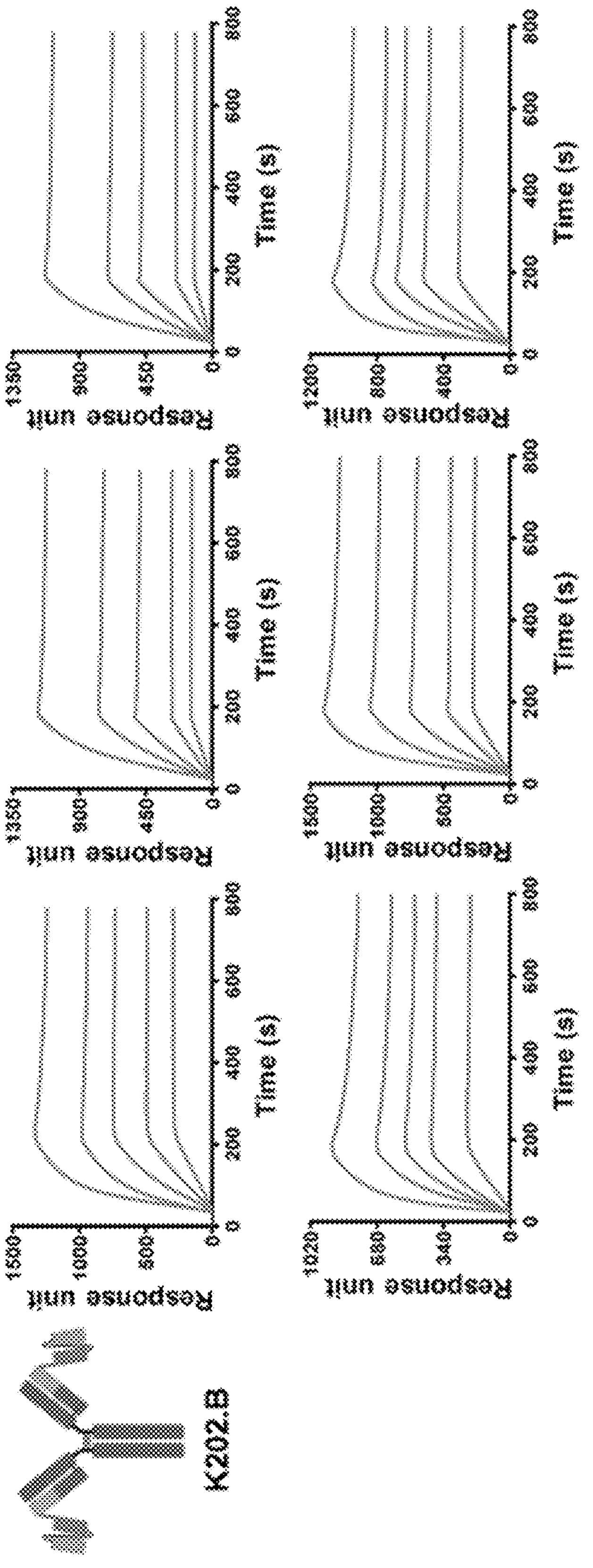

Of the designed bispecific antibody forms, the two IgG4 (S228P)-(scFv) 2 bsAb forms K202.A and K202.B were produced with a purity of 90% or higher (FIG. 39). Then, surface plasmon resonance (SPR) analysis was conducted to compare binding affinity for purified RBDs of wild-type SARS-CoV-2 and SARS-CoV-2 variants comprising alpha, beta, gamma, delta, and kappa between the bsAbs and mAb. The results are depicted in FIG. 40*a-d.*

As can be seen in FIG. 40*a-d* and Table 6, K202.B exhibited as strong binding affinity for RBDs of all the SARS-CoV-2 variants tested in the subnanomolar concentration range as comparable with that of the parental mAb for wild-type SARS-CoV-2.

To further confirm whether K202.B could recognize two independent epitopes of SARS-CoV-2 RBD, competition assays were performed using SPR. The results are depicted in FIG. 41.

Figure 41:
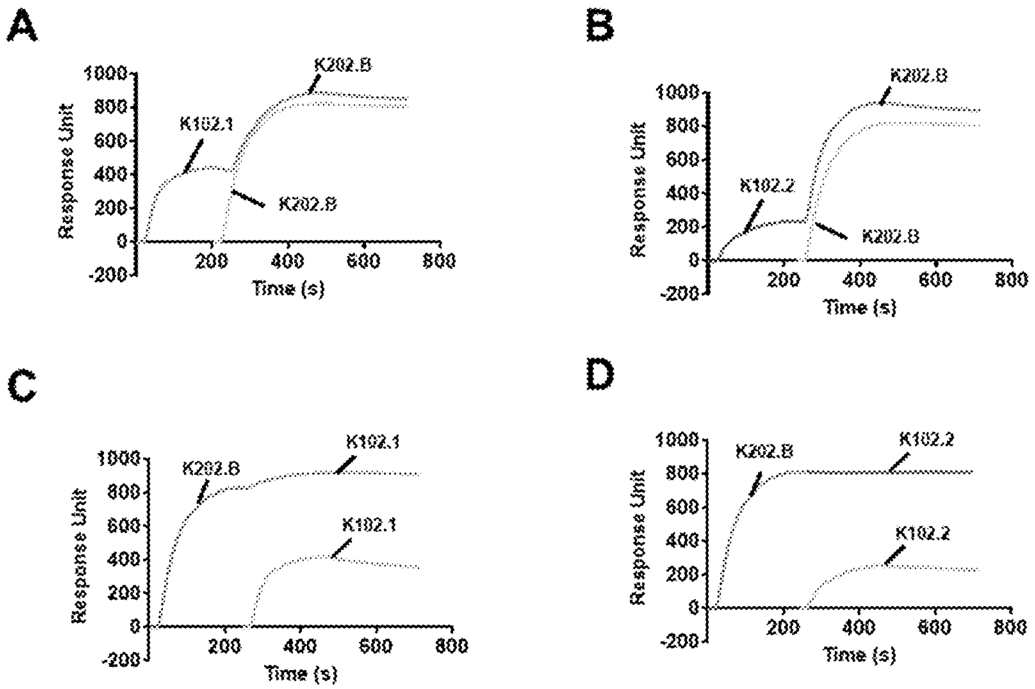
FIG. 41 shows results of competition assays conducted to identify the recognition of two different independent epitopes by the bispecific antibody of the present disclosure as measured by SPR.

As shown in FIG. 41, K202.B could bind to the RBD even after saturation with K102.1 or K102.2 (FIGS. 41A and 41B). In contrast, neither K102.1 nor K102.2 bound to the RBD after saturation with K202.B (FIGS. 41C and 41D), suggesting that the bsAb K202.B specifically recognized two independent binding sites.

TABLE 6

Equilibrium dissociation constant of parental mAbs and bsAbs to RBDs of SARS-CoV-2 wild-type and variants

| RBD type | $K_a$ ($M^{-1}$) | $K_d$ ($M^{-1}S^{-1}$) | $K_D$ (nM) | $K_a$ ($M^{-1}$) | $K_d$ ($M^{-1}S^{-1}$) | $K_D$ (nM) |
|---|---|---|---|---|---|---|
| | K102.1 | | | K102.2 | | |
| Wild-type | 1.61 × $10^5$ | 2.76 × $10^{-4}$ | 1.72 | 1.97 × $10^5$ | 4.34 × $10^{-4}$ | 2.20 |
| B.1.1.7 | 2.06 × $10^5$ | 1.93 × $10^{-4}$ | 0.94 | 1.54 × $10^5$ | 5.57 × $10^{-4}$ | 3.62 |
| B.1.351 | 0.93 × $10^5$ | 2.95 × $10^{-4}$ | 3.18 | 4.92 × $10^5$ | 7.88 × $10^{-4}$ | 1.60 |
| P.1 | 0.70 × $10^5$ | 3.15 × $10^{-4}$ | 4.51 | 4.54 × $10^5$ | 9.39 × $10^{-4}$ | 2.07 |
| B.1.617.2 | 2.11 × $10^5$ | 2.98 × $10^{-4}$ | 1.41 | 3.33 × $10^5$ | 5.11 × $10^{-4}$ | 1.53 |
| B.1.617.1 | 0.95 × $10^5$ | 3.17 × $10^{-4}$ | 3.34 | 4.07 × $10^5$ | 6.83 × $10^{-4}$ | 1.68 |
| | K202.A | | | K202.B | | |
| Wild-type | 1.65 × $10^5$ | 1.29 × $10^{-4}$ | 0.78 | 1.47 × $10^5$ | 9.98 × $10^{-5}$ | 0.68 |
| B.1.1.7 | 1.89 × $10^5$ | 1.08 × $10^{-4}$ | 0.57 | 8.31 × $10^5$ | 7.93 × $10^{-4}$ | 0.95 |
| B.1.351 | 0.78 × $10^5$ | 2.49 × $10^{-4}$ | 3.17 | 2.22 × $10^5$ | 2.00 × $10^{-4}$ | 0.90 |
| P.1 | 2.03 × $10^5$ | 3.81 × $10^{-4}$ | 1.88 | 0.87 × $10^5$ | 1.86 × $10^{-4}$ | 2.14 |
| B.1.617.2 | 2.47 × $10^5$ | 2.26 × $10^{-4}$ | 0.92 | 1.50 × $10^5$ | 1.17 × $10^{-4}$ | 0.78 |
| B.1.617.1 | 2.48 × $10^5$ | 2.82 × $10^{-4}$ | 1.14 | 2.78 × $10^5$ | 1.60 × $10^{-4}$ | 0.58 |

$K_a$, Association constant
$K_d$, Dissociation constant
$K_D$, Equilibrium dissociation constant

Figure 42:
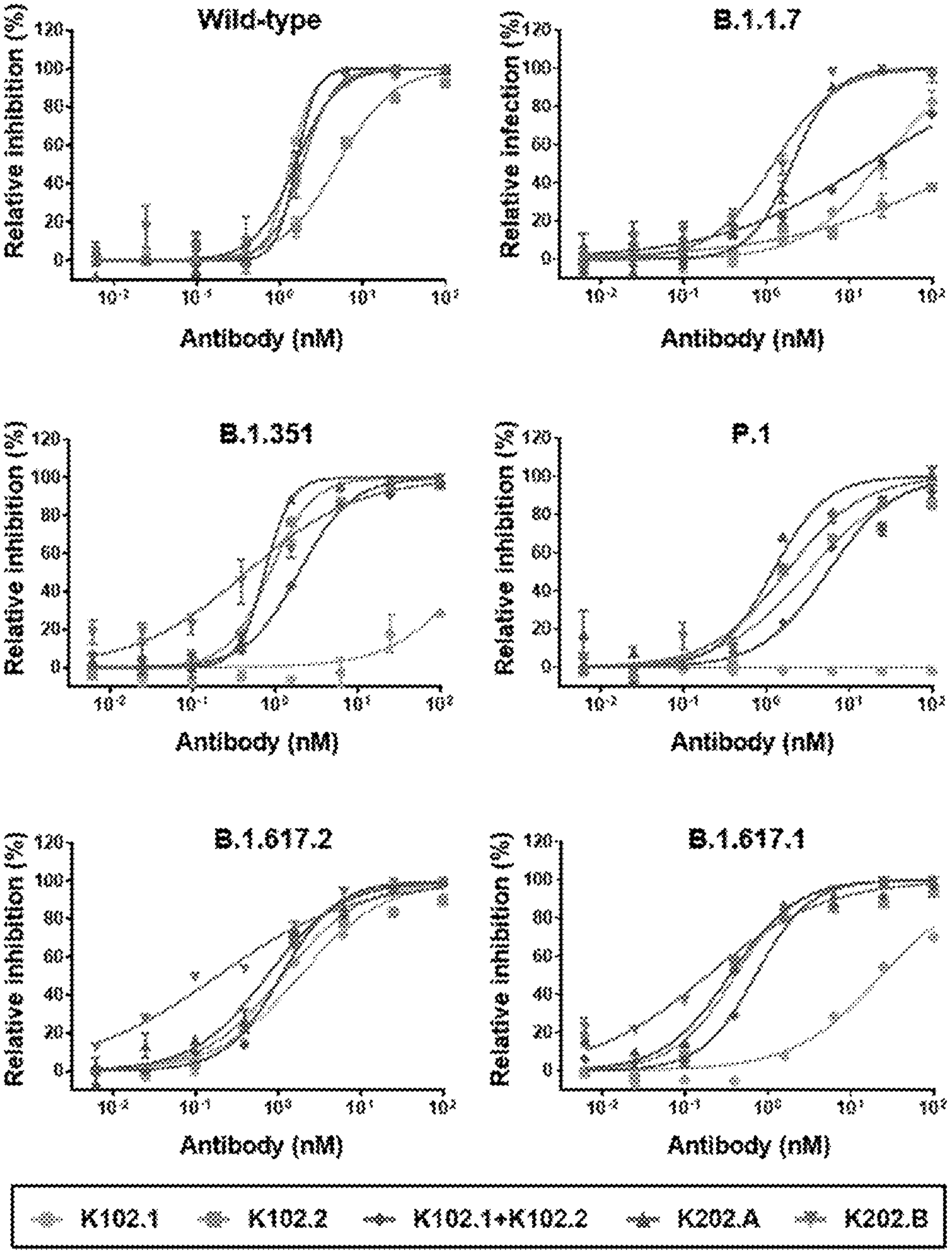
FIG. 42 shows binding inhibition efficacy of the bispecific antibody at various antibody concentrations to confirm the neutralizing activity of the bispecific antibody against interaction between hACE2 and SARS-CoV-2 wild-type and variants.

Example III-2: Neutralizing Activity of bsAb in hACE2-RBD Interaction and SARS-CoV- 2 Pseudotyped and Live Virus Infection In Vitro 2-1. Neutralizing Activity of bsAbs in hACE2-RBD Interaction To assess the neutralizing activity of the bsAbs in hACE2-RBD interactions, ELISA-based neutralization assays were performed with microtiter plates to which the recombinant RBD proteins of wild-type SARS-CoV-2 and SARS-CoV-2 variants comprising alpha, beta, gamma, delta, and kappa variants. The microtiter plates were incubated with recombinant hACE2 in the presence or absence of parental mAb, an mAb cocktail containing parental mAb, or bsAbs. The results are depicted in FIG. 42 and summarized in FIG. 7.

TABLE 7

$IC_{50}$ values of inventive antibodies in direct interaction between hACE2 and RBDs of the wild-type and variant SARS-CoV-2

| RBD type | K102.1 | K102.2 | K102.1 + K102.2 | K202.A | K202.B |
|---|---|---|---|---|---|
| | $IC_{50}$ (nM) | | | | |
| Wild-type | 1.33 ± 0.04 | 4.94 ± 0.06 | 1.55 ± 0.07 | 1.57 ± 0.20 | 1.85 ± 0.09 |
| B.1.1.7 | 23.10 ± 0.06 | ND | 16.79 ± 0.16 | 2.04 ± 0.07 | 1.21 ± 0.10 |
| B.1.351 | ND | 0.86 ± 0.06 | 1.94 ± 0.06 | 0.75 ± 0.03 | 0.45 ± 0.15 |
| P.1 | ND | 3.23 ± 0.16 | 5.52 ± 0.13 | 1.19 ± 0.12 | 1.73 ± 0.10 |
| B.1.617.2 | 1.83 ± 0.09 | 1.14 ± 0.11 | 1.08 ± 0.08 | 0.73 ± 0.09 | 0.18 ± 0.12 |
| B.1.617.1 | 24.32 ± 0.09 | 0.40 ± 0.10 | 0.71 ± 0.06 | 0.34 ± 0.08 | 0.19 ± 0.11 |

ND, Not determined

As is understood from data of FIG. 42 and Table 7, in the case of hACE2 binding to the wild-type RBD, all the antibodies exhibited similar inhibitory effects, but K202.B bispecific antibody more potently inhibits the hACE2 binding than the mAb or mAb cocktail. In addition, as demonstrated in the subnanomolar range of IC50 values, K202.B was observed to have a little advantageous inhibitory effect on hACE2 binding to the RBDs of the beta, delta, and kappa variants, compared to K202.A.

Figure 43A:
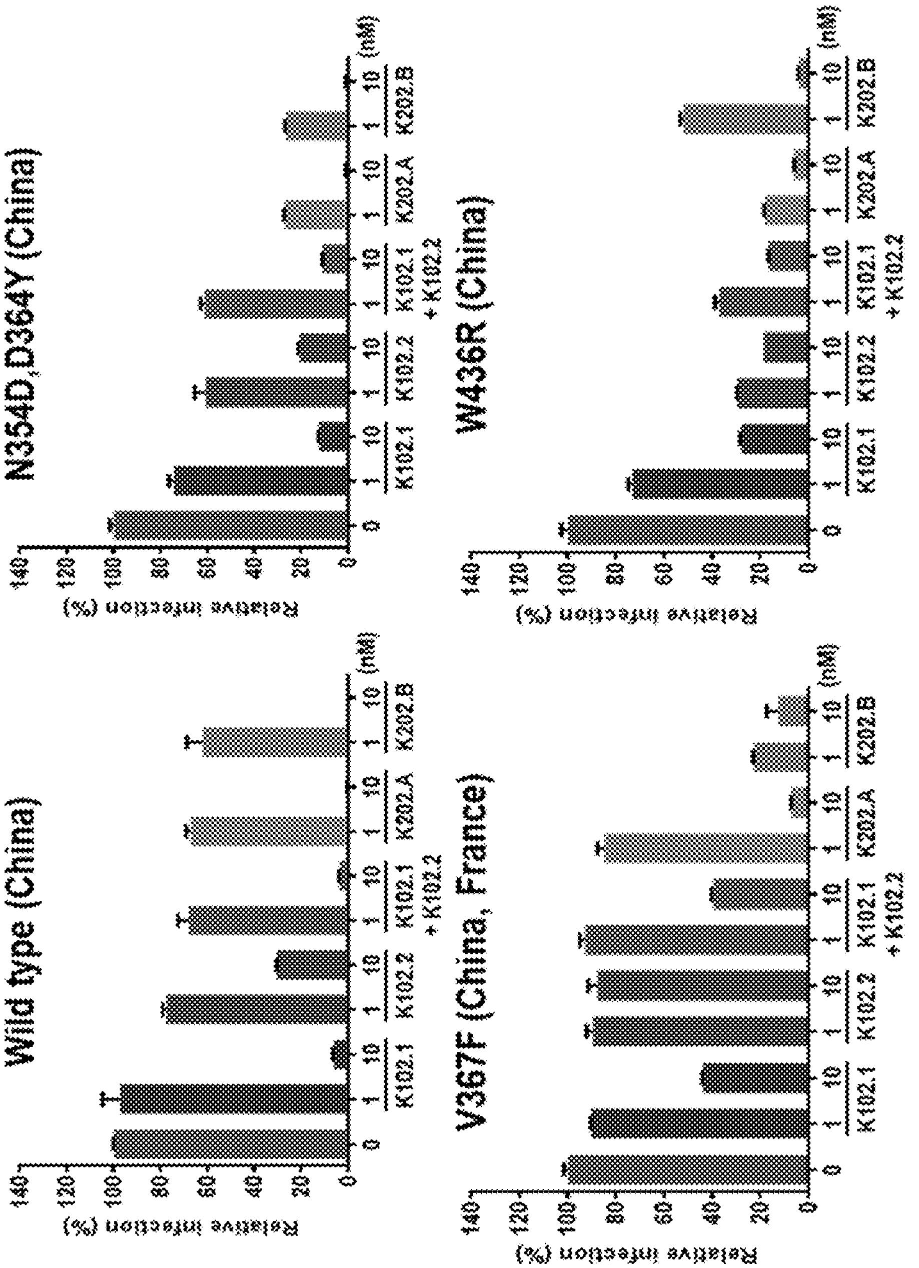
FIGS. 43*a* and 43*b* show binding inhibition efficacy of the bispecific antibody of the present disclosure at various antibody concentrations to confirm the neutralizing activity of the bispecific antibody against interaction between hACE2 and RBD with the mutation N354D/D364Y, V367F, W436R, R408I, G476S, V483A, V341I, F342L, or A435S.
Figure 43B:
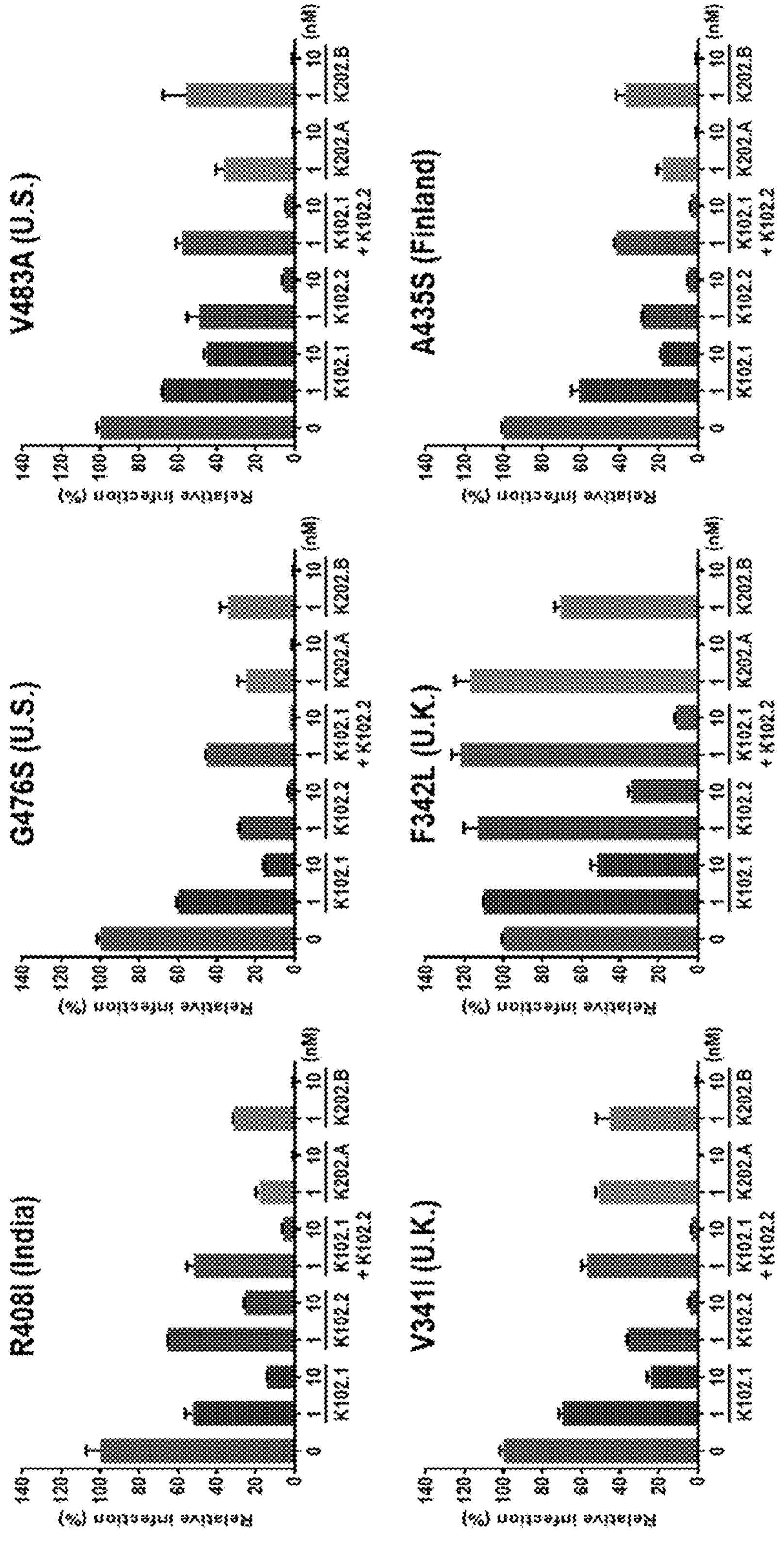

Furthermore, K202.B also exhibited a strong inhibitory effect on hACE2 binding to RBDs with N354D/D364Y, V367F, W436R, R408I, G476S, V483A, V341I, F342L, or A435S mutations (FIG. 43*a, b*).

Figure 44:
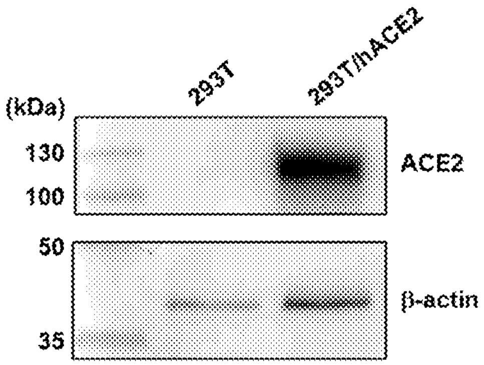
FIG. 44 shows the establishment of hACE2-overexpresisng 293T stable cell lines (293T/hACE2 cells).
Figure 44:
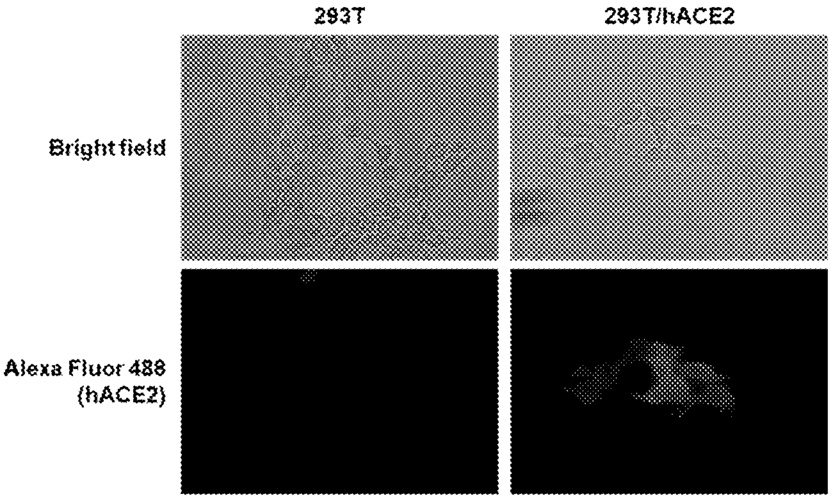

2-2. Neutralizing Activity of bsAbs Against SARS-CoV-2 Pseudotyped Virus Infection To assess the neutralizing ability of the bsAbs of the present disclosure against SARS-CoV-2 pseudotyped virus infection, SARS-CoV-2 pseudotyped virus neutralization assays were conducted using hACE2-overexpressing 293T stable cell line (293T/hACE2 cells) (FIG. 44) in the presence or absence of parental mAbs, mAb cocktail, and bsAbs.

Figure 45:
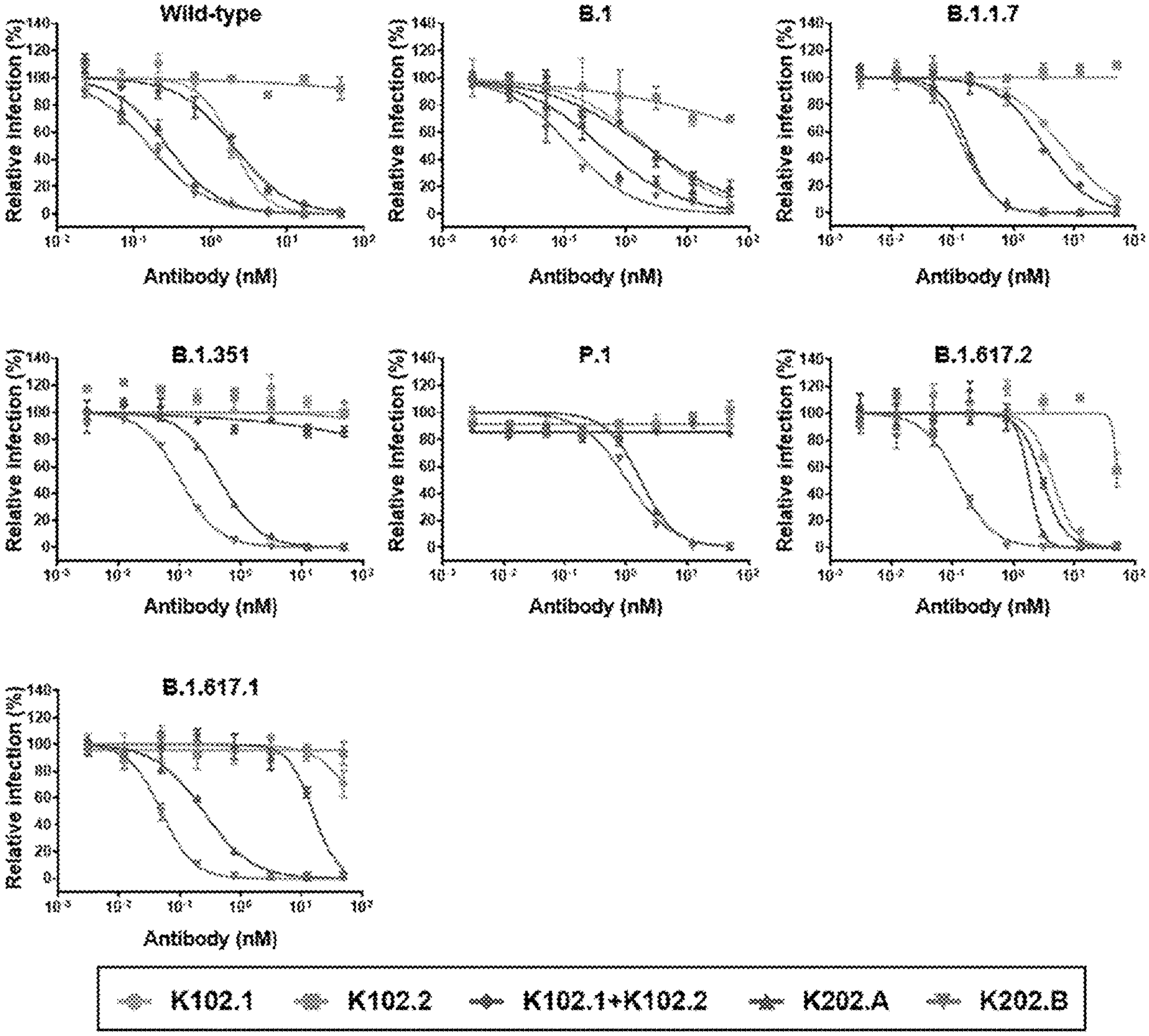
FIG. 45 shows neutralizing activity of the antibodies against the pseudotyped virus infection of SARS-CoV-2 wild-type and variants.
Figure 46A:
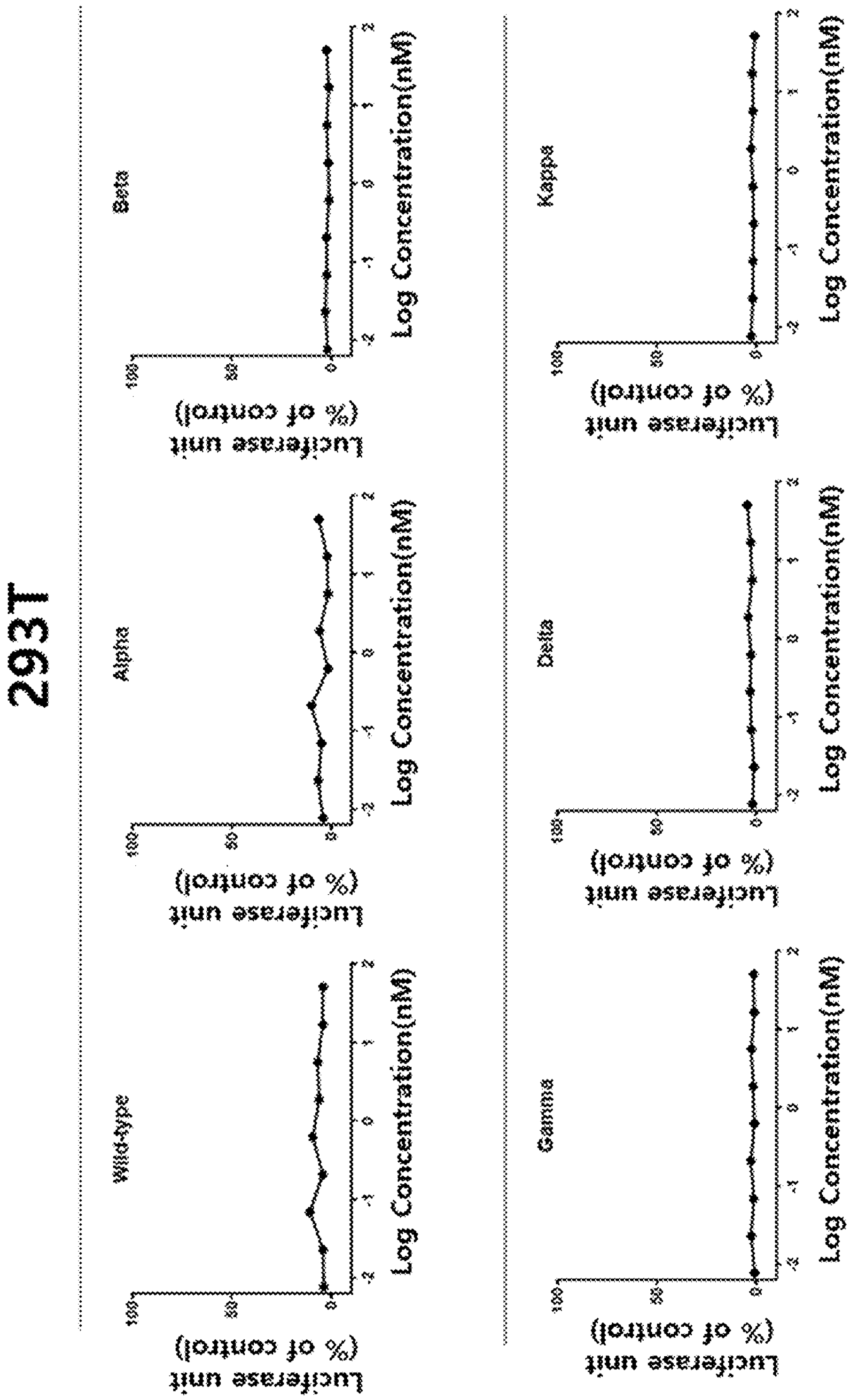
FIGS. 46*a*, 46*b*, 46*c* and 46*d* shows changes in pseudotyped virus infection of various SARS-CoV-2 wild-type and variants in the presence or absence of the bispecific antibody K202.B of the present disclosure.
Figure 46B:
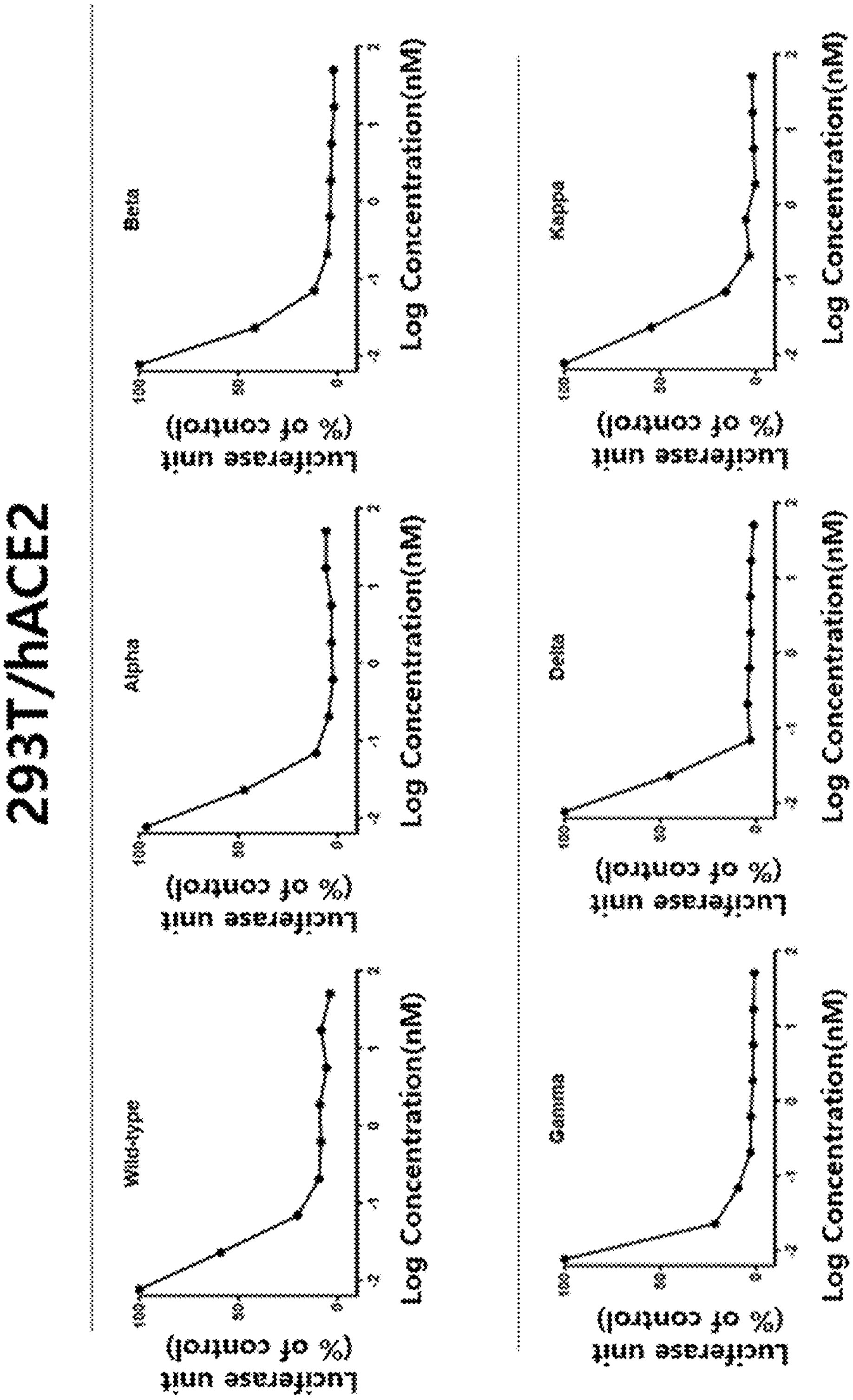
Figure 46C:
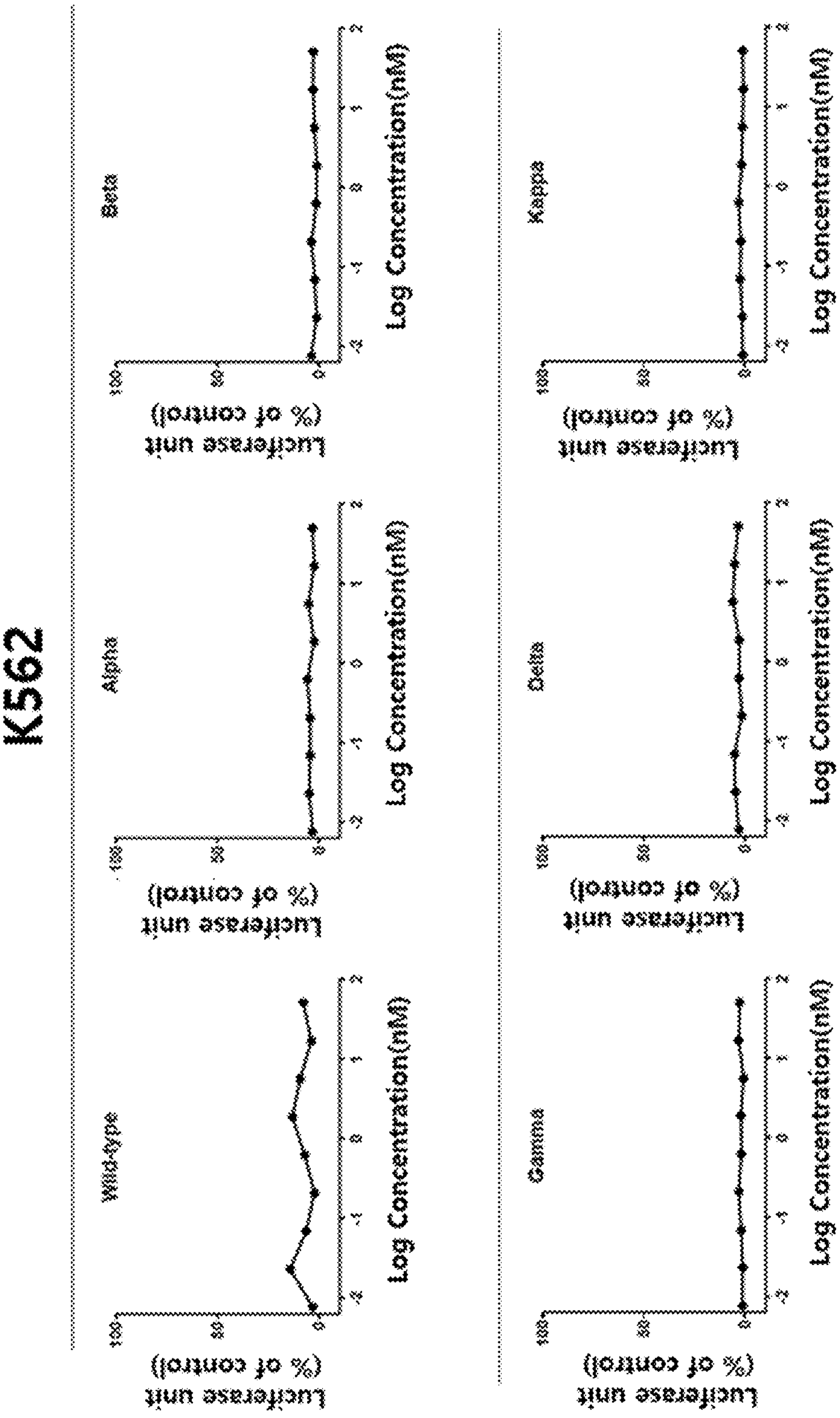
Figure 46D:
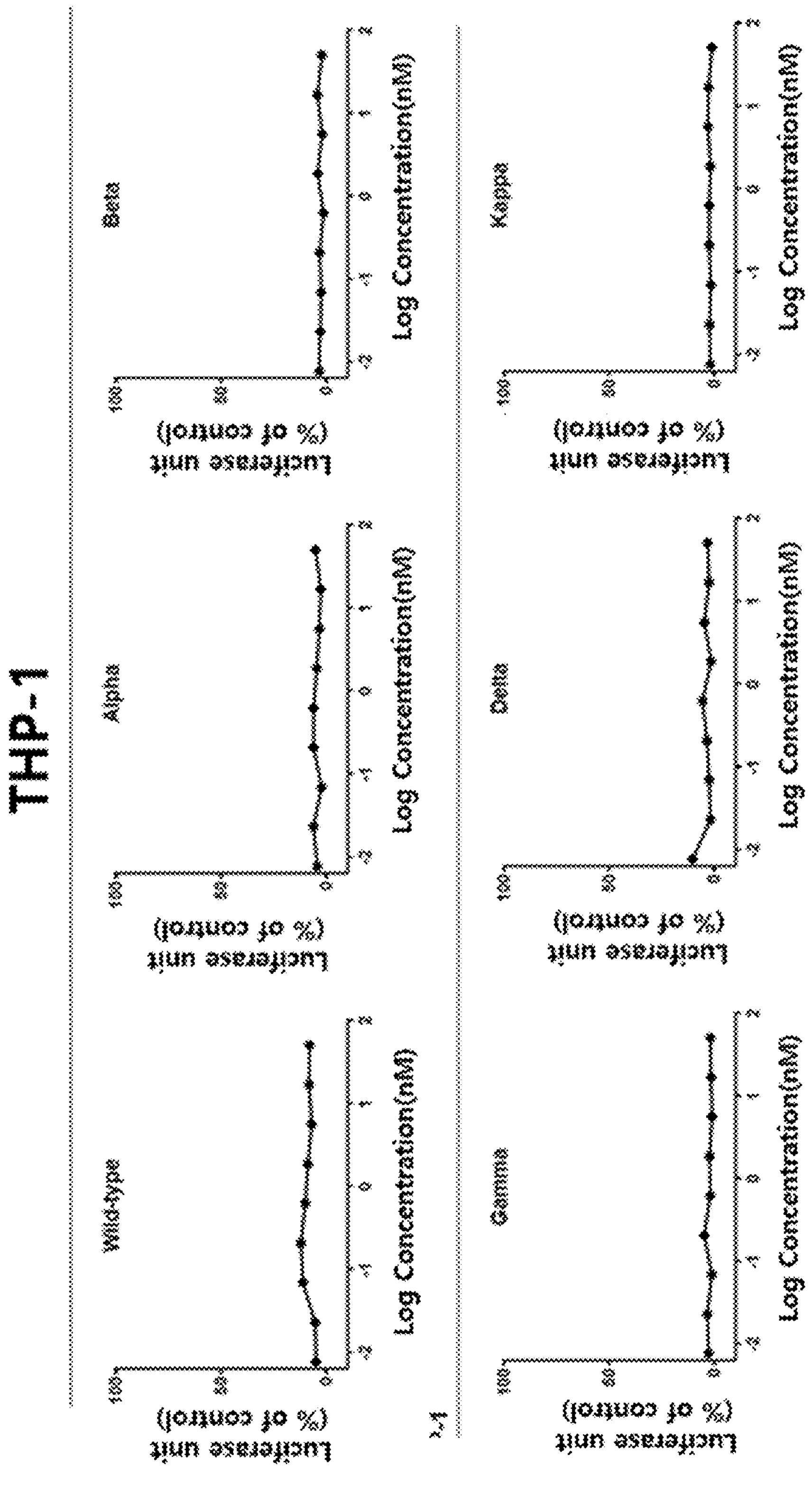

The results are depicted in FIG. 45 and summarized in Table 8.

TABLE 8

$IC_{50}$ values of antibodies against pseudotyped virus infection of SARS-CoV-2 wild-type and variants.

| Pseudo-virus type | K102.1 | K102.2 | K102.1 + K102.2 | K202.A | K202.B |
|---|---|---|---|---|---|
| | $IC_{50}$ (nM) | | | | |
| Wild-type | 1.94 ± 0.07 | ND | 1.96 ± 0.08 | 0.27 ± 0.07 | 0.16 ± 0.04 |
| B.1 | 2.22 ± 0.09 | ND | 2.05 ± 0.14 | 0.39 ± 0.14 | 0.12 ± 0.11 |
| B.1.1.7 | 6.16 ± 0.08 | ND | 3.12 ± 0.07 | 0.18 ± 0.03 | 0.15 ± 0.03 |
| B.1.351 | ND | ND | ND | 0.46 ± 0.04 | 0.10 ± 0.04 |
| P.1 | ND | ND | ND | 1.74 ± 0.10 | 1.04 ± 0.09 |
| B.1.617.2 | 4.48 ± 0.10 | ND | 3.04 ± 0.08 | 1.83 ± 0.13 | 0.13 ± 0.09 |
| B.1.617.1 | ND | ND | 15.63 ± 0.08 | 0.24 ± 0.04 | 0.05 ± 0.04 |

ND, Not determined

As shown in FIG. 45, it was observed that the parental antibody K102.1 of the present disclosure significantly inhibited the pseudotyped virus infection of wild-type, B.1 (D614G), alpha, and delta variants in the nanomolar range, but did not inhibit the infection of the other variants. On the other hand, K102.2 had no effects on any of the tested pseudoviruses.

In contrast, K202.B exhibited stronger inhibitory effects on the infection of almost all the tested pseudotyped viruses than parental mAbs or the mAb cocktail with the IC50 values of mostly subnanomolar or nanomolar concentrations. The inhibitory effect of the bispecific antibody K202.A was similar to or slightly lower than that of the bispecific antibody K202.B (FIG. 45 and Table 8).

2-3. Neutralizing Activity of bsAbs in Live Virus Infection

Next, the effect of the bispecific antibody K202.B of the present disclosure on the antibody-dependent enhancement (ADE) was evaluated using permissive cells (293T/hACE2 cells) and Fc gamma receptor-bearing cells (293T, K562, and THP-1 cells). Changes in the pseudotyped virus infection rate of various SARS-CoV-2 wild-type and variants were monitored in the presence of K202.B. The results are depicted in FIG. 46*a-d.*

As can be seen in FIG. 46*a-d*, no significant changes were observed in any pseudotyped virus infection in the presence of K202.B, indicating that the bispecific antibody K202.B of the present disclosure may not induce ADE in vivo.

Example III-3: Assay for In Vivo Efficacy and Toxicity of Bispecific Antibody K202.B in Wild-Type SARS-CoV-2-Infected Animal Models 3-1. In Vivo Seropharmacokinetic Assay To investigate the pharmacokinetics of the bispecific antibody K202.B, K202.B was intravenously injected at a dose of 5 mg/kg into ICR mice from which blood was then sampled at various times. Serum levels of K202.B were measured by ELISA. The results are depicted in FIG. 47.

Figure 47:
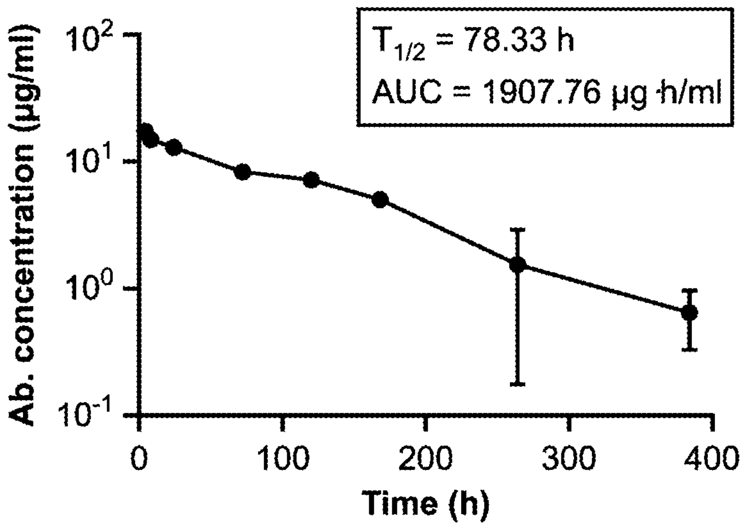
FIG. 47 is a plot showing pharmacokinetic properties of the bispecific antibody K202.B of the present disclosure.

As shown in FIG. 47, it was found that K202.B exhibited an in vivo half-life of approximately 78 hours in mice.

3-2. In Vivo Efficacy Assay

Next, an analysis was made of in vivo efficacy of the bispecific antibody K202.B on wild-type SARS-CoV-2.

Figure 48:
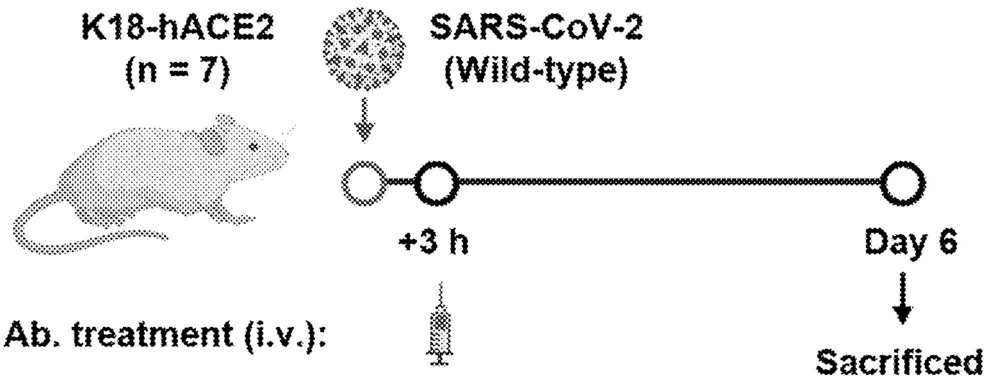
FIG. 48 is a schematic view illustrating an experiment for analyzing in vivo efficacy of the bispecific antibody K202.B of the present disclosure in wild-type SARS-CoV-2.

Briefly, wild-type SARS-CoV-2 viruses were intranasally administered to the K18-hACE2 transgenic (TG) mice. After 3 hours, the mice were intravenously injected with two doses (5 and 30 mg/kg) of K202.B, or a single dose (30 mg/kg) of K102.1. At 6 days post-infection, the mice were sacrificed and analyzed as illustrated in FIG. 48. The results are depicted in FIGS. 49 and 50.

Figure 49:
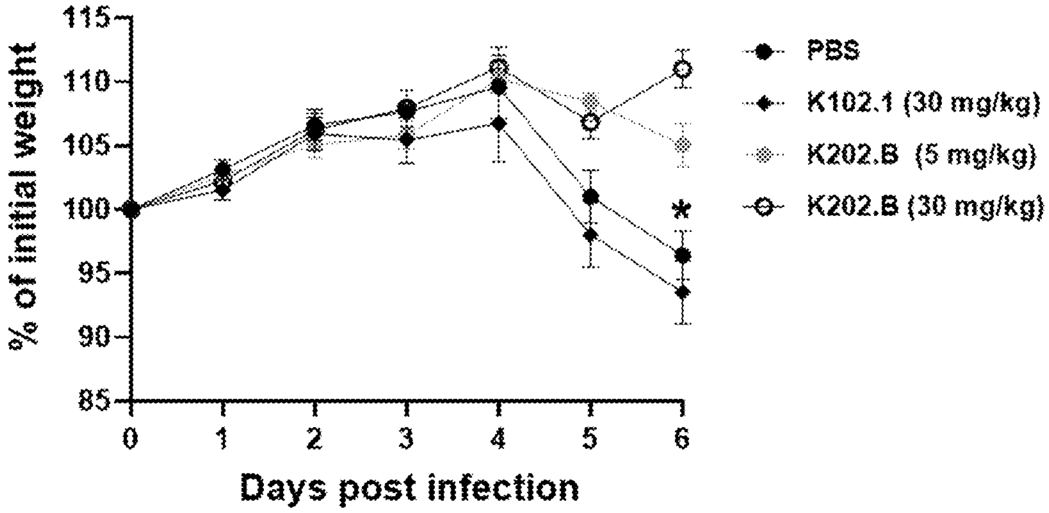
FIGS. 49, 50, 51, 52 and 53 show in vivo efficacy of the bispecific antibody K202.B of the present disclosure in response to treatment with SARS-CoV-2 wild-type virus and antibody in terms of daily body weight change (FIG. 49), clinical score (FIG. 50), expression level of viral gene (FIGS. 51 and 52), and pathological examination of lung (FIG. 53).

As shown in FIG. 49, no significant body weight losses were detected in the wild-type SARS-CoV-2-infected mice injected with the bispecific antibody K202.B over the observation period of time while the mice treated with PBS and K102.1 underwent notable weight loss at 6 days post-injection (dpi).

Figure 50:
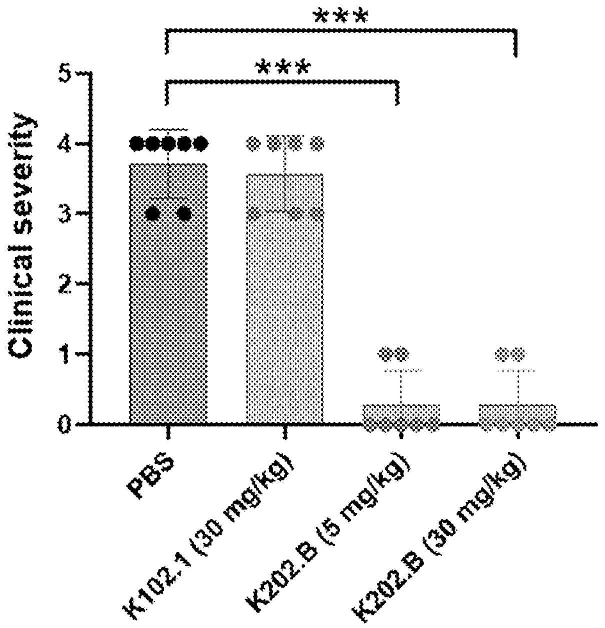

In addition, as shown in FIG. 50, each K202.B-treated group exhibited a clinical severity score of 1 or less (mostly score 0), whereas PBS- or K102.1-treated groups displayed scores greater than 3, characterized by a very ruffled coat, slightly closed eyes, and/or a moribund state.

In addition, lung samples from all mice sacrificed at 6 dpi were subjected to RT-qPCR to determine the relative expression of viral E and RNA-dependent RNA polymerase (RdRp) genes. The results are depicted in FIGS. 51 and 52.

Figure 51:
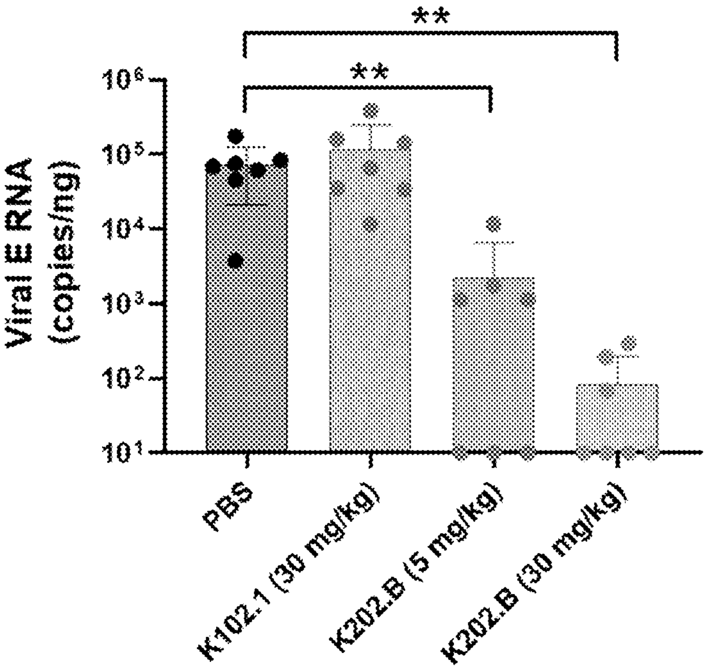
Figure 52:
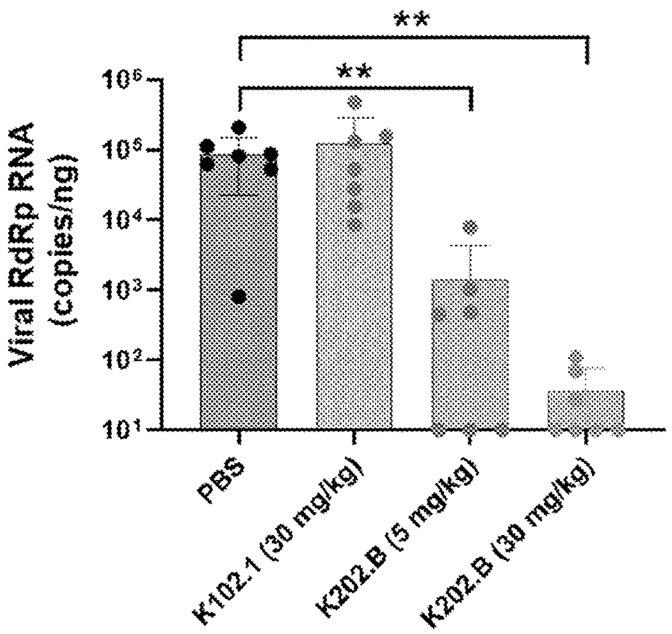

As shown in FIGS. 51 and 52, the expression of both viral genes was significantly reduced in a dose-dependent manner in each bispecific antibody K202.B-treated group when compared with that in the PBS-treated group. However, the K102.1-treated group underwent only a slight reduction.

Figure 53:
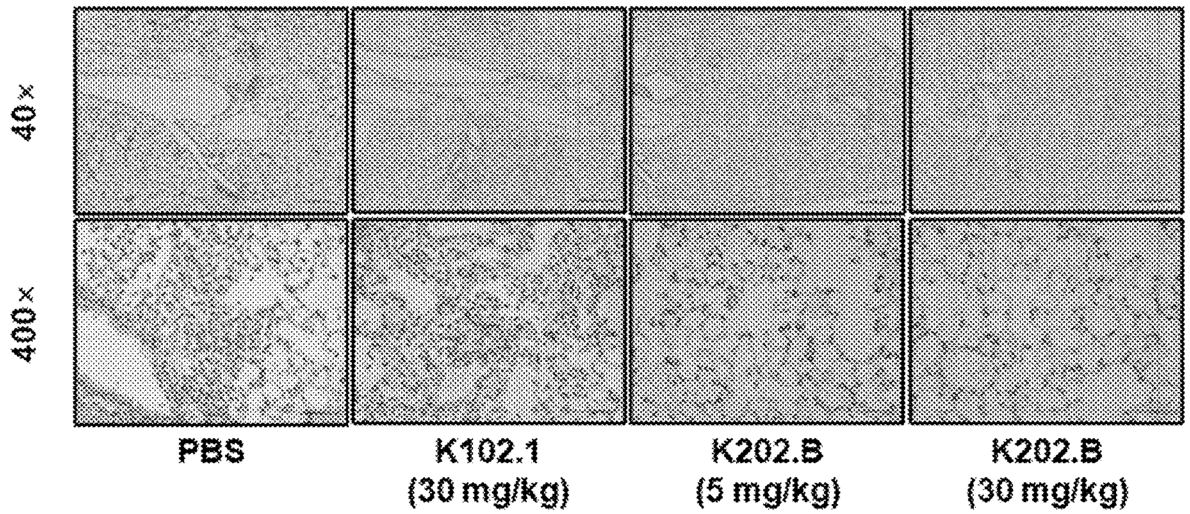

Furthermore, histopathological examination made of lungs from the infected mice at $6^{th}$ dpi and the results are depicted in FIG. 53 and summarized in Table 9.

TABLE 9

Pathological score analyses of lungs from the wild-type SARS-CoV-2-infected mice

| Pathological score | Number of specimen (n = 7) | | | |
|---|---|---|---|---|
| | PBS | K102.1 (30 mg/kg) | K202.B (5 mg/kg) | K202.B (30 mg/kg) |
| 0 | 0 | 0 | 2 (28.57%) | 3 (42.86%) |
| 0.5 | 0 | 0 | 0 | 0 |
| 1 | 2 (28.57%) | 3 (42.86%) | 1 (14.29%) | 4 (57.14%) |
| 1.5 | 3 (42.86%) | 4 (57.14%) | 0 | 0 |
| 2 | 2 (28.57%) | 0 | 4 (57.14%) | 0 |
| Mean* | 1.43 | 1.07 | 1.29 | 0.57 |

*Mean = (pathological score × numbers of specimen)/total numbers of specimen
Pathological score = (0, 0%; 1, ≤10%; 2, 10%-50%; 3, ≥50%; +0.5, pulmonary edema or alveolar hemorrhage)

As can be seen in Table 9, PBS- and K102.1-treated mice scored 1 or more due to significant pulmonary lesions. In contrast, a high proportion of the K202.B-treated group showed a score of 0 at both 5 and 30 mg/kg doses.

As shown in FIG. 53, further histopathological analyses revealed normal features in the K202.B-treated lungs, whereas PBS- and K102.1-treated mice exhibited severe pulmonary edema or alveolar hemorrhage.

3-3. In Vitro Cytotoxicity Assay

To assay in vitro cytotoxicity of the bispecific antibody of the present disclosure, endothelial cells were measured for cell viability after treatment with 20 μg/ml K202.B or 36 μg/ml 5-fluorouracil. The results are given in FIG. 54.

Figure 54:
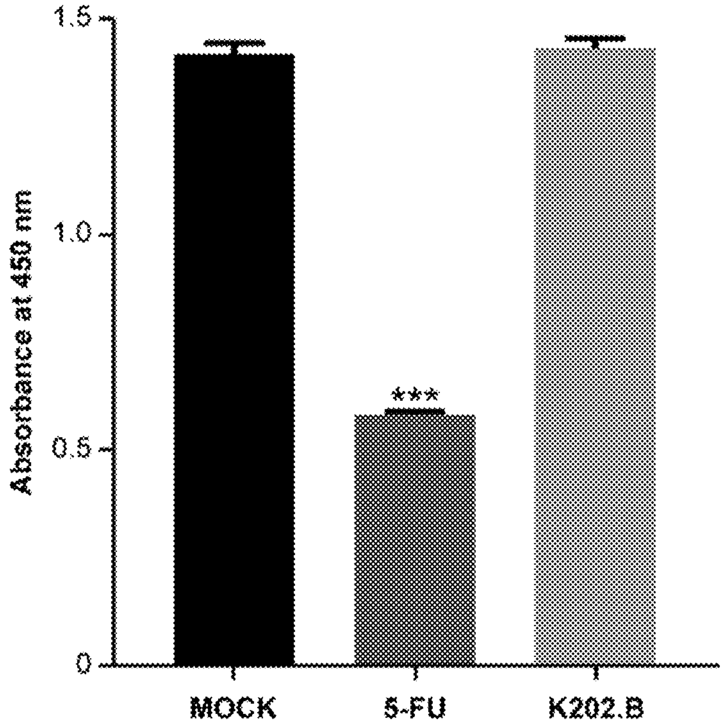
FIGS. 54 and 55 show in vitro toxicity of the bispecific antibody K202.B of the present disclosure in terms of cell viability (FIG. 54) and expression levels of cell adhesion molecules (FIG. 55).

As shown in FIG. 54, there was no significant effect of K202.B on endothelial cell viability in the K202.B-treated group compared with the control group, suggesting no severe endothelial toxicity.

Moreover, to confirm the effect of the bispecific antibody on endothelial activation, the cells were treated with inflammatory cytokine (hTNF-α) or bispecific antibody K202.B and measured for expression levels of cell adhesion molecules (ICAM-1 and VCAM-1). The results are depicted in FIG. 55.

Figure 55:
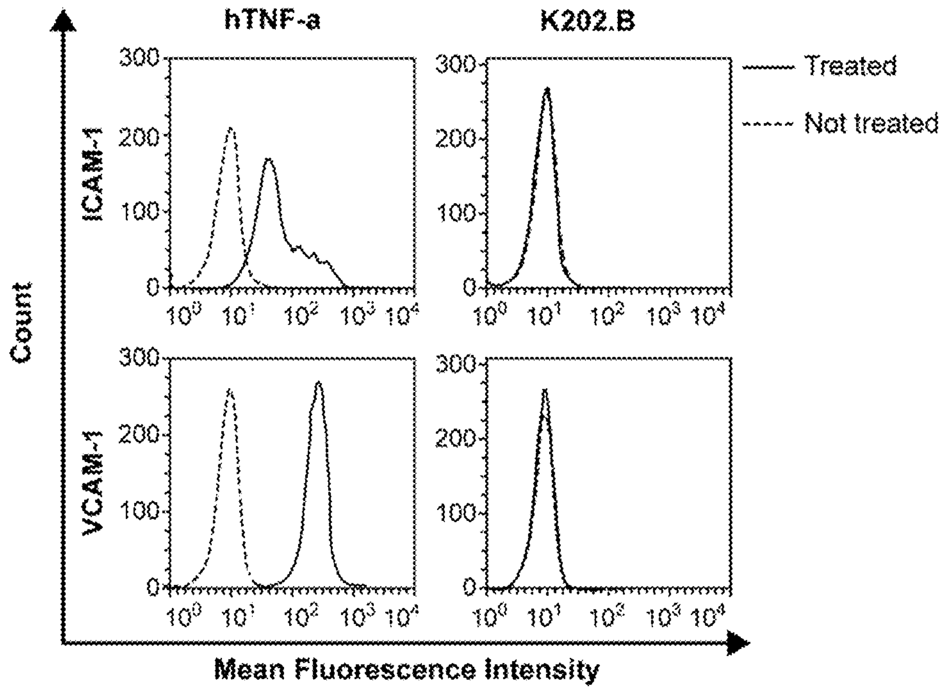

As shown in FIG. 55, the expression of cell adhesion molecules (ICAM-1 and VCAM-1) was activated in the hTNF-α-treated group whereas the cell group treated with the bispecific antibody K202.B of the present disclosure remained unchanged in the expression of cell adhesion molecules (ICAM-1 and VCAM-1), indicating that the bispecific antibody K202.B of the present disclosure has no effect on endothelial activation and thus does not cause endothelial toxicity.

3-4. In Vivo Cytotoxicity Assay

To evaluate in vivo cytotoxicity of the bispecific antibody K202.B, K202.B was intravenously injected to mice and hepatic and renal toxicity were assayed using the sera.

Figure 56:
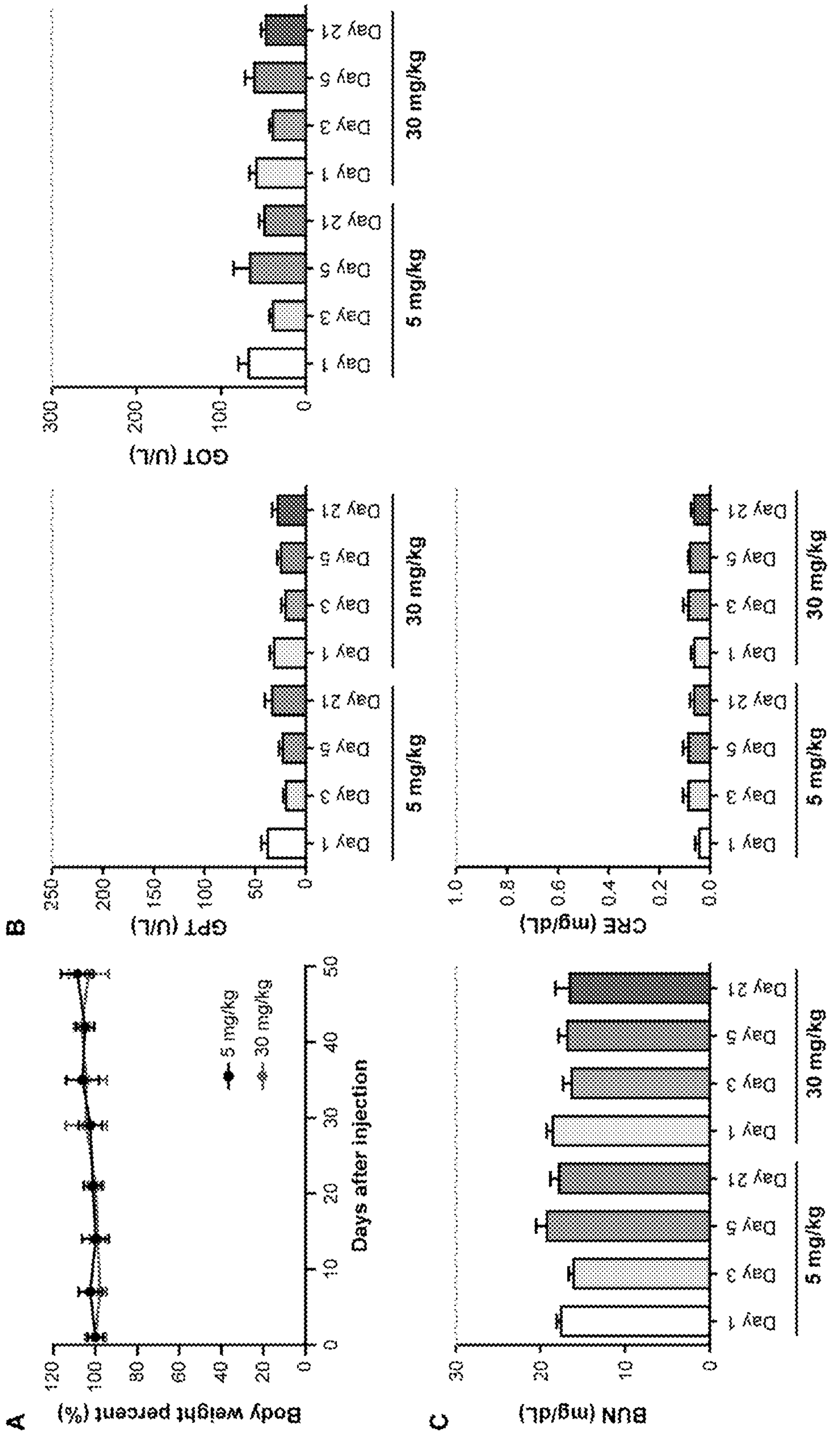
FIG. 56 shows biochemical examination results of in vivo toxicity responsible for hepatic and renal toxicity with sera from mice to which K202.B has been administered.

The results are depicted in FIG. 56.

As shown in FIG. 56, no changes were observed in either body weight or biochemical indices indicative of hepatic and renal toxicity, implying that the bispecific antibody K202.B of the present disclosure does not provoke in vivo toxicity.

Figure 57:
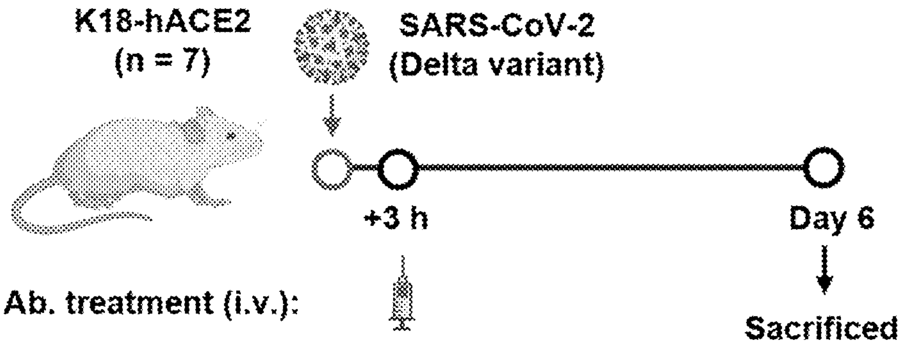
FIG. 57 is a schematic view illustrating an experiment for analyzing in vivo efficacy of the bispecific antibody K202.B of the present disclosure in SARS-CoV-2 delta variant.

Example III-4: In Vivo Assay for Efficacy and Toxicity of Bispecific Antibody K202.B in SARS-CoV-2 Delta Variant-Infected Animal Models 4-1. In Vivo Efficacy Assay In vivo efficacy of bispecific K202.B against SARS-CoV-2 delta variant was analyzed. To evaluate the in vivo efficacy of K202.B against SARS-CoV-2 delta variant, K18-hACE2 TG mice was intranasally challenged with SARS-CoV-2 delta virus. After 3 hours, the mice received intravenous injections of a dose of 5 or 30 mg/kg of K202.B (FIG. 57).

Figure 58:
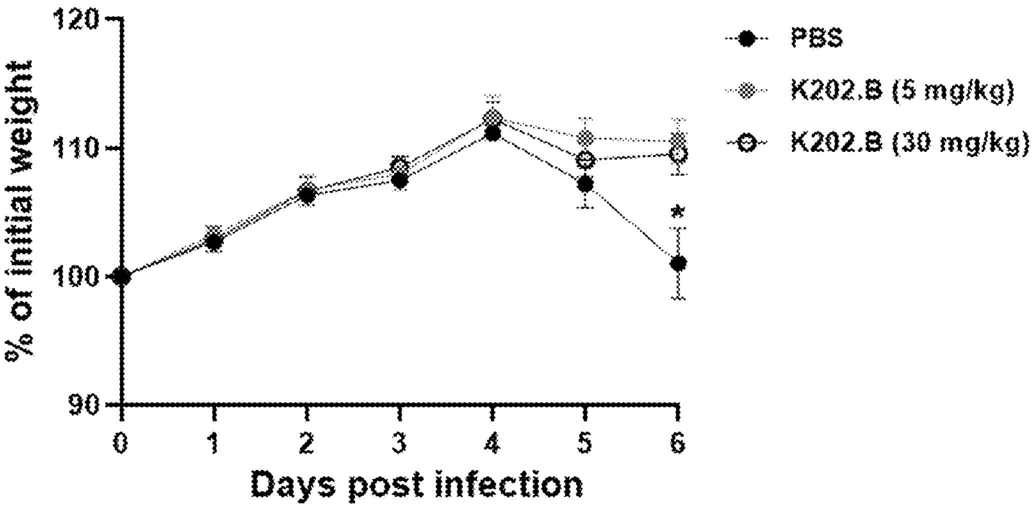
FIGS. 58, 59, 60, 61 and 62 show in vivo efficacy of the bispecific antibody K202.B of the present disclosure in response to treatment with SARS-CoV-2 delta variant virus and antibody in terms of daily body weight change (FIG. 58), clinical score (FIG. 59), expression level of viral gene (FIGS. 60 and 61), and pathological examination of lung (FIG. 62).

As shown in FIG. 58, the PBS-treated group decreased in body weight at $6^{th}$ dpi with statistical significance whereas no drastic weight loss was observed in the bispecific antibody K202.B-treated group.

Figure 59:
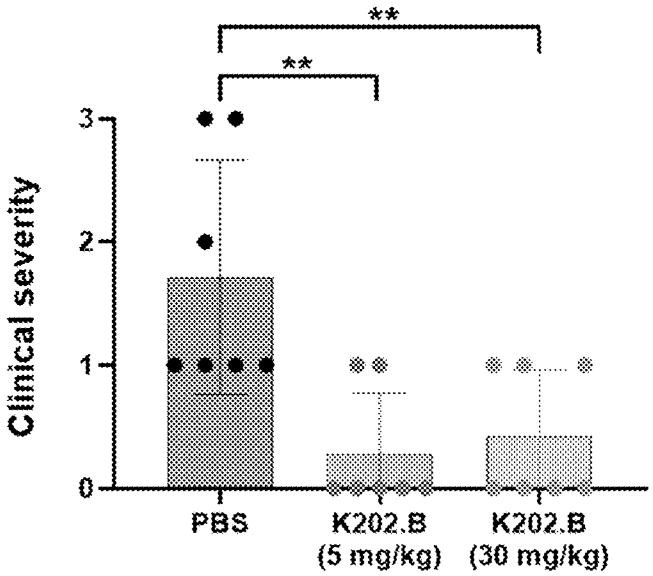

In addition, as shown in FIG. 59, the bispecific antibody K202.B-treated group exhibited a clinical severity score of 1 or less (mostly score 0).

Figure 60:
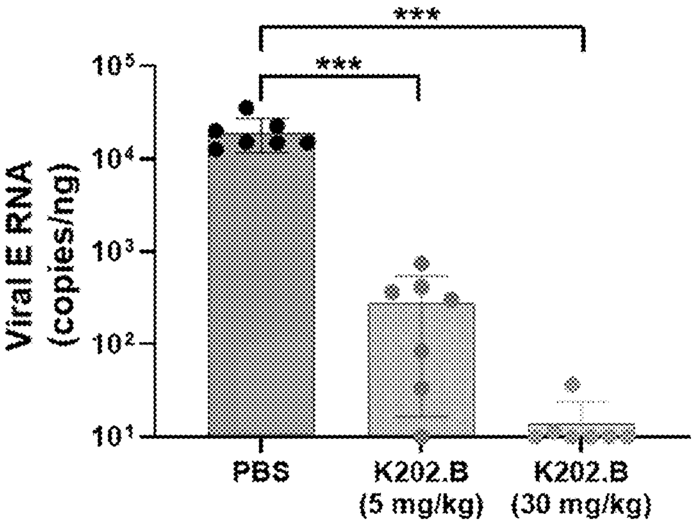
Figure 61:
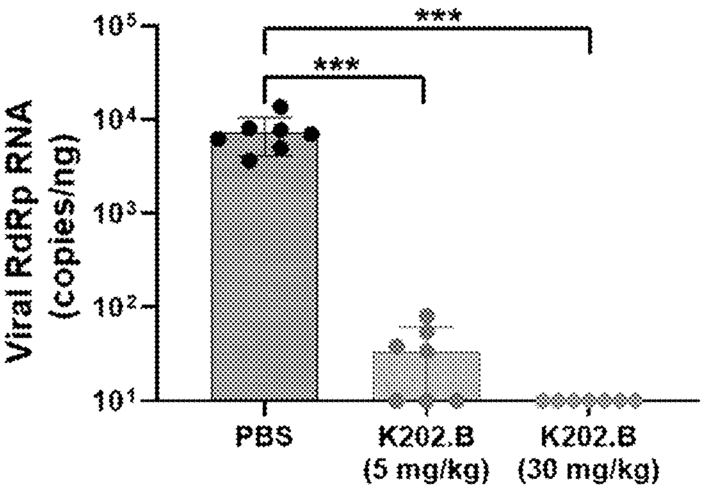

Lung samples from all mice sacrificed at 6 dpi were subjected to RT-qPCR to determine the relative expression of viral E and RNA-dependent RNA polymerase (RdRp) genes. As can be seen in FIGS. 60 and 61, the K202.B-treated group was observed to effectively reduce the expression of both viral E and RdRp genes, compared to the PBS-treated group, as measured by RT-qPCR. Particularly, almost no viral gene was detected in the 30 mg/kg K202.B-treated group at 6 dpi.

Figure 62:
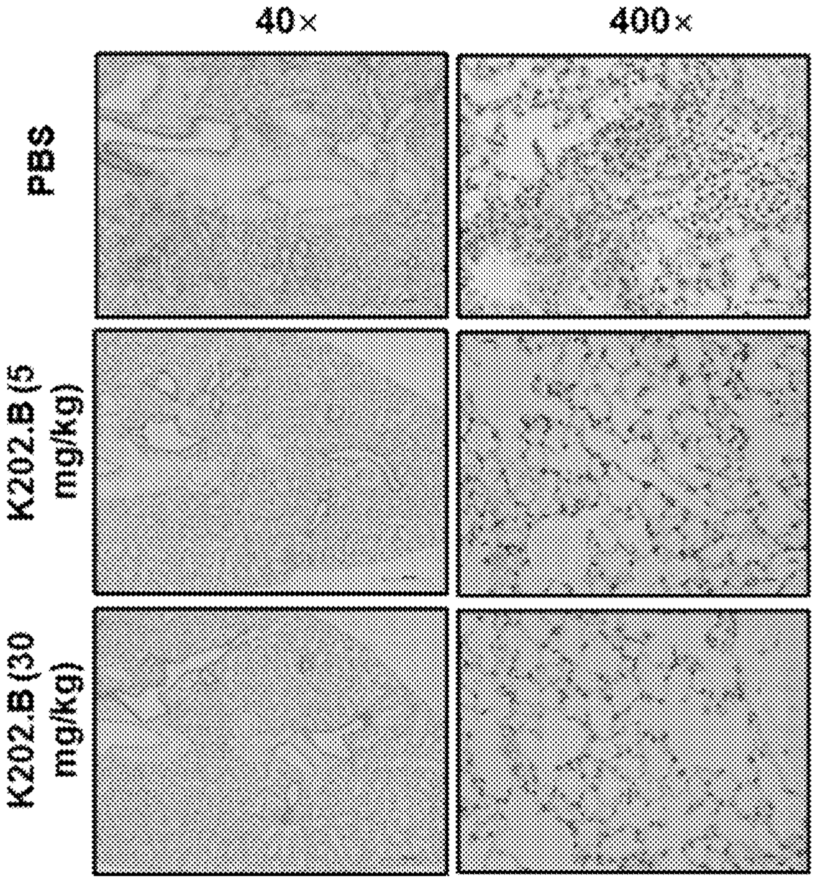

Furthermore, histopathological examination made of lungs from the infected mice at 6 dpi and the results are depicted in FIG. 62 and summarized in Table 10. As can be seen in Table 10, the pathological score in the K202.B-treated group was increased in a dose-dependent manner from 0 point whereas the PBS-treated mice scored 1 to 2 (mostly 2) due to significant pulmonary lesions.

As shown in FIG. 62, histopathological analyses revealed normal features in the K202.B-treated lungs whereas PBS-treated mice exhibited pulmonary edema or alveolar hemorrhage.

TABLE 10

Pathological score analyses of lungs from the SARS-CoV delta variant-infected mice

| Pathological score | Numbers of specimen (n = 7) PBS | K202.B (5 mg/kg) | K202.B (30 mg/kg) |
|---|---|---|---|
| 0 | 0 | 2 (28.57%) | 5 (71.43%) |
| 0.5 | 0 | 0 | 0 |
| 1 | 2 (28.57%) | 5 (71.43%) | 2 (28.58%) |
| 1.5 | 1 (14.29%) | 0 | 0 |
| 2 | 4 (57.14%) | 0 | 0 |
| Mean* | 1.57 | 0.71 | 0.29 |

*Mean = (pathological score × numbers of specimen)/total numbers of specimen

Pathological score = (0, 0%; 1, ≤10%; 2, 10%-50%; 3, ≥50%; +0.5, pulmonary edema or alveolar hemorrhage)

Example III: Materials and Methods

III-1. Cell Culture

The cell lines 293T, K562, and THP-1 were purchased from the American Type Culture Collection (ATCC, Rockville, MD, USA). A purchase was made of CHOZN-GS cells (derived from CHO-K1 and adapted to serum-free and suspension conditions) from Merck (Merck, Whitehouse Station, NJ, USA), Expi293 cells from Thermo Fisher Scientific (Waltham, MA, USA), and human umbilical vein endothelial cells (HUVEC) from Lonza (Basel, Switzerland). 293T cells were cultured in DMEM (Thermo Fisher Scientific) whereas K562 and THP-1 cells were cultured in RPMI media (Thermo Fisher Scientific) media supplemented with 10% (v/v) FBS (Thermo Fisher Scientific) and 100 U/mL penicillin-streptomycin (Thermo Fisher Scientific) at 37° C. in 5% $CO_2$. HUVECs were maintained in EGM-2 (Lonza). Expi293 cells were cultured in Expi293™ Expression Media in shaking incubators at 37° C., 125 rpm, and 8% $CO_2$. CHOZN-GS cells were in EX-CELL Advanced CHO Fed-batch medium (Sigma-Aldrich, Burlington, MA, USA) in a microscale bioreactor Ambr®15 (Sartorius, Göttingen, Germany) at 37° C.

III-2. Surface Plasmon Resonance (SPR)

The binding kinetics of antibodies to SARS-CoV-2 RBDs were analyzed at room temperature on an iMSPR-mini instrument (iCLUEBIO, Seongnam, Republic of Korea) using 10 mM HEPES pH 7.4, 700 mM NaCl, 2 mM $CaCl_2$), 1 mM $MnCl_2$, and 0.005% (v/v) Tween-20 as a running buffer. The recombinant SARS-CoV-2 RBDs (wild-type and variants comprising B.1.1.7 (alpha), B.1.351 (beta), P.1 (gamma), B.1.617.2 (delta), and B.1.617 (kappa)) were covalently immobilized on the surface of a COOH—Au chip (iCLUEBIO) up to 500 response units through standard amine coupling. Antibodies (8, 16, 32, 64, and 128 nM, respectively) were injected onto the surface of a sensor chip at a flow rate of 50 μL/min. Kinetics evaluation data was obtained using a 1:1 binding model.

To evaluate the ability of K202.B to bind to different regions of the RBD, competition experiments were performed. After the immobilization of 5 nM WT-RBD-His on the surface of a COOH—Au chip, a high concentration (512 nM) of K102.1 or K102.2 antibody was added to saturate the corresponding binding sites on the RBD. Then, 128 nM K202.B was added. Conversely, following the addition of 512 nM K202.B to the surface of recombinant WT-RBD-His-immobilized sensor chip, 256 nM K102.1 or K102.2 was subsequently added. Curve fitting and data analysis were performed using the iMSPR analysis software (Tracedrawer; iCLUEBIO).

III-3. SARS-CoV-2 RBD-Human ACE2 Interaction Neutralization Assay

The ability of antibodies to inhibit the interaction of the SARS-CoV-2 RBD with hACE2 was investigated using ELISA. 50 ng of purified Fc-tagged hACE2 (hACE2-Fc) (R&D Systems, Minneapolis, MN, USA) was coated in each well of a 96-well plate and incubated for 2 hours at room temperature. After washing with immunobuffer (BPS Bioscience, San Diego, CA, USA), the plates were blocked with blocking buffer (BPS bioscience) for 1 hour at room temperature. Simultaneously, 25 nM of purified SARS-CoV-2 WT- or variant-RBD-His (alpha, beta, gamma, delta, and kappa) (Sino Biological) was pre-incubated in the presence or absence of mAb or bsAbs (0.006, 0.024, 0.097, 0.39, 1.56, 6.25, 25, and 100 nM) for 1 hour at room temperature.

III-4. Establishment of hACE2-Overexpressing 293T Stable Cell Line (293T/hACE2 Cell Line)

To generate stable 293T/hACE2 cell lines, a pUNO1-hACE2 plasmid (InvivoGen, San Diego, CA, USA) was transfected into 293T cells using Lipofectamine 2000 (Invitrogen) according to the manufacturer's instructions. After 48 hours of transfection, the cells were cultured in a medium containing 20 μg/mL blasticidin (InvivoGen) to select positive cell populations. The expression of hACE2 was determined using immunoblot and immunocytochemical analysis. For immunoblot analysis, 293T and 293T/hACE2 cell lines were lysed with SDS sample buffer, and subjected to immunoblot analysis using a polyclonal anti-hACE2 antibody (R&D Systems). The distribution of hACE2 in the cell membrane was studied through immunocytochemical analysis. Briefly, 293T and 293T/hACE2 cells were plated on Nunc® Lab-Tek® II chamber slides (Thermo Fisher Scientific) coated with poly-L-lysine (0.1 mg/mL) (Sigma-Aldrich, St. Louis, MO, USA). After 24 hours, the cells were fixed with 4% formaldehyde for 10 min and washed twice with PBS.

The cells were blocked using PBS containing 1% (w/v) BSA and incubated with polyclonal anti-hACE2 antibody overnight at 4° C. After washing thrice with PBS, the cells were subsequently incubated with Alexa Fluor 488-labeled anti-goat secondary antibody (Invitrogen) at room temperature for 1 hour, then mounted with mounting solution (Dako North America, Carpinteria, CA, USA). The stained cells were imaged using confocal microscopy (LSM510; Carl Zeiss, Oberkochen, Germany).

III-5. SARS-CoV-2 Pseudotyped Virus Neutralization Assay

Pseudotyped replication-deficient lentiviral particles carrying the SARS-CoV-2 spike(S) protein of the wild-type or D614G variant, and a firefly luciferase reporter gene were prepared using Lenti-X™ SARS-CoV-2 packaging mix according to the manufacturer's instruction (Takara Bio, Kusatsu, Japan). Briefly, the packaging mix was transiently transfected into Expi293T cells with ExpiFectamine 293 reagent. After culturing for 72 hours, the supernatants containing the pseudotyped viruses were collected and centrifuged briefly (500×g for 10 min) to remove cellular debris. Virus titration was measured using Lenti-X GoStix Plus (Takara Bio) according to the manufacturer's instructions. The pseudotyped replication-deficient Moloney murine leukemia virus particles carrying the SARS-CoV-2 S protein of alpha, beta, gamma, delta, or kappa variants and a firefly luciferase reporter gene were obtained from eEnzyme (Gaithersburg, MD, USA).

To determine the neutralization activity of mAbs or bsAbs against pseudotyped virus infection, $1\times10^4$ 293T/hACE2 cells in 50 μL culture medium were seeded in 96-well tissue culture plates overnight. Serial dilutions of the antibodies were pre-incubated at room temperature for 10 min with 50 μL of each pseudotyped virus ($1\times10^7$ PFU/mL), and the mixture was subsequently incubated with the cells for 24 hours. The firefly luciferase reporter gene expression (which is indicative of viral presence) was measured using ONE-Glo luciferase substrate (Promega, Madison, WI, USA). Next, the culture medium was removed and incubated with 100 μL of ONE-Glo substrate. After 5 min, 70 μL supernatant was transferred to white flat-bottom 96-well assay plates (Corning) and the luminescence signal was measured using the Synergy H1 microplate reader. The recorded relative luminescence units were normalized to those derived from cells infected with each SARS-CoV-2 pseudotyped virus in the absence of antibodies. Dose-response curves for $IC_{50}$ values were determined by nonlinear regression (GraphPad Prism 8.0 software).

III-6. In Vivo Mouse Study

For in vivo efficacy studies, 8-week-old female B6.Cg-Tg(K18-ACE2)2Prlmn/J (hACE2) mice (The Jackson Laboratory, CA, USA), were housed in a certified A/BSL3 facility (Korea Zoonosis Research Institute, Iksan, Republic of Korea). All procedures were approved by the Institutional Animal Care and Use Committee (IACUC) at KNOTUS (No. 22-KE-0076), and all experimental protocols requiring biosafety were approved by the Institutional Biosafety Committee of Jeonbuk National University (approval number: JBNU 2020-11-003-003) and performed in a biosafety cabinet at the BL3 and ABL3 facilities of Korea Zoonosis Research Institute at Jeonbuk National University.

The hACE2-transgenic (hACE2-TG) mice (n=7) was intranasally inoculated with 30 μL of wild-type or delta variant virus ($1\times10^4$ PFU) under anesthesia. Three hours after infection, PBS, mAbs, or bsAbs were injected intravenously.

The mice were monitored daily for weight change and clinical severity based on the criteria as shown in the table 11.

TABLE 11

| Score | Description | Appearance & Mobility |
|---|---|---|
| 0 | Healthy | No observable sign of disease |
| 1 | Slightly ruffled | Slightly ruffled coat |
| 2 | Ruffled | Ruffled coat throughout the body and a wet appearance |
| 3 | Sick | Very ruffled coat and slightly closed, inset eyes |
| 4 | Very sick | Very ruffled coat; closed, inset eyes; and moribund state |

The SARS-CoV-2 burden in lung tissues was determined via RT-qPCR. Lung tissues were harvested from hACE2-TG mice 6 days after SARS-CoV-2 wild-type or delta variant infection, and total RNAs were extracted from the collected tissues using Wizol Reagent (Wizbiosolutions, Seongnam, Republic of Korea). The samples were subjected to RT-qPCR using a CFX96 Real-Time PCR Detection System (Bio-Rad Laboratories, Hercules, CA, USA).

Following the reverse transcription of total RNA using a High-Capacity cDNA Reverse Transcription Kit (Applied Biosystems, Foster, CA, USA), the reaction mixture (20 μL total) contained 2 μL of template cDNA, 10 μL of 2× Premix Ex Taq, 200 nM primer, and a probe (E gene: forward primer 5'-ACAGGTACGTTAATAGTTAATAGCGT-3' (SEQ ID NO: 67), reverse primer 5'-ATATTGCAGCAGTACGCACACA-3' (SEQ ID NO: 68), probe 5'-FAM-ACACTAGCCATCCTTACTGCGC TTCG-BHQ1-3' (SEQ ID NO: 69); RdRp gene: forward primer 5'-ATGAGCTTAGTCCTGTTG-3' (SEQ ID NO: 70), reverse primer 5'-CTCCCTTTGTTGTGTTGT-3' (SEQ ID NO: 71), probe 5'-HEX-AGATTGTCTTGTGCTGCCGGTA-BHQ1-3' (SEQ ID NO: 72)). These reactions were denatured at 95° C. for 30 seconds, and then subjected to 45 cycles of 95° C. for 5 seconds and 60° C. for 20 seconds. After completion of the reaction cycles, the temperature was increased from 65 to 95° C. at a rate of 0.2° C./15 seconds and fluorescence was measured every 5 seconds to construct a melting curve. A control sample lacking template DNA was run with each assay. All measurements were performed in duplicate to ensure reproducibility. The authenticity of the amplified product was determined using melting curve analysis. All data were analyzed using Bio-Rad CFX Manager analysis software version 2.1 (Bio-Rad Laboratories). The viral burden was expressed by the copy number of viral RNA per nanogram of total RNA after calculating the absolute copy number of viral RNA in comparison with the standard cDNA template.

Histology

Excised mouse lung tissues were fixed with 4% (v/v) paraformaldehyde (PFA) in PBS and processed for paraffin embedding. The paraffin blocks were sliced into 3 μm-thick sections using a microtome (HistoCore MULTICUT R; Leica, Germany) and mounted on silane-coated glass slides (5116-20F; Muto, Tokyo, Japan). Hematoxylin and eosin, periodic acid-Schiff, and modified Masson's trichrome stains were used to identify histopathological changes in all the organs. The histopathology of the lung tissue was observed using light microscopy (Axio Scope A1; Carl Zeiss). Pathological scores were determined based on the percentage of inflammation area for each section in each group using the following scoring system: 0, no pathological change; 1, affected area (≤10%); 2, affected area (10-50%); 3, affected area (≥50%); an additional 0.5 point was added when pulmonary edema and/or alveolar hemorrhage was observed.

III-7. In Vitro Antibody-Dependent Enhancement Assay

Fifty microliters of each SARS-CoV-2 pseudotyped virus ($1\times10^7$ PFU/mL) was preincubated with different concentrations of K202.B (0.044, 0.138, 0.42, 1.24, 3.7, 11.1, 33.3, and 100 nM) in culture medium. After 30 minutes of incubation at room temperature, the mixture was added to 293T, 293T/hACE2, K562, or THP-1 cells ($1\times10^4$ cells in a 96-well plate). The cells were cultured for 24 hours, and the luciferase activity of infected cells was measured as described in "pseudotyped virus neutralization assay".

III-8. Endothelial Cell Viability Assay

A total of $5\times10^3$ HUVECs were plated in 96-well plates and incubated in the presence or absence of 20 μg/mL K202.B or 36 μg/mL 5-fluorouracil for 24 hours at 37° C. Cell viability was determined using the Cell Counting Kit-8 (Sigma) according to the manufacturer's instructions. The final absorbance was measured at 450 nm using a spectrophotometer (BioTek).

III-9. Flow Cytometry

The effect of K202.B on endothelial cell activation was determined by treating cells with 20 ng/ml of human tumor necrosis factor-α (hTNF-α; Millipore), 20 μg/ml of K202.B, or PBS for 24 hours and fixing with 4% (v/v) PFA. The cells were fixed with 4% (v/v) PFA in PBS and incubated with 10 μg/well of intercellular cell adhesion molecule-1 (ICAM-1; Abcam, Cambridge, MA, USA) or vascular cell adhesion molecule-1 (VCAM-1; Abcam) antibody for 1 hour at 25° C. Then, Alexa Fluor 647-conjugated anti-mouse IgG or anti-rabbit IgG (1:1000; Invitrogen) was incubated for 1 hour at 25° C. All samples were analyzed using flow cytometry with the aid of FlowJo software (TreeStar, Ashland, OR, USA).

III-10. In Vivo Toxicity and Serum Pharmacokinetic Analysis

In vivo toxicity and serum pharmacokinetic studies using animals were approved by the IACUC (Approval No. NCC-21-693) of the National Cancer Center, Republic of Korea. Eight-week-old female Institute of Cancer Research (ICR) mice (Orient Bio Inc., Seongnam, Republic of Korea) were intravenously injected with 5 or 30 mg/kg of K202.B (n=3 per group). At 4, 8, 24, 72, 120, 168, 264, 384, and 504 hours post-inoculation, blood samples (50 μL) were collected from each mouse and centrifuged at 5000×g for 20 min at 4° C. The serum was stored at −80° C. for evaluation of biochemical parameters. Serum levels of glutamic oxaloacetic transaminase (GOT), glutamic pyruvic transaminase (GPT), creatinine (CRE), and blood urea nitrogen (BUN) were measured using a Fuji Dri-Chem 3500 Biochemistry Analyzer (Fujifilm, Tokyo, Japan).

Serum levels of K202.B were determined using a human IgG ELISA kit (Abcam) according to the manufacturer's instructions. Optical density was measured using a Synergy H1 microplate reader, and values were compared to those from a concurrently analyzed standard curve.

III-11. Statistical Analysis

Data were analyzed with GraphPad Prism 8.0 software using two-tailed Student's t-test for comparisons between two groups, and one-way analysis of variance (ANOVA) with Bonferroni's correction for multiple comparisons. All data represent the mean±standard deviation (S.D.). A P-value less than 0.05 was considered statistically significant (*P<0.05, P<0.01, *P<0.001).

What is claimed is:

1. An antibody or an antigen binding fragment thereof specifically binding to SARS-CoV-2 S protein, comprising:

(i) a heavy chain variable region comprising CDR-H1 of SEQ ID NO: 1, CDR-H2 of SEQ ID NO: 2, and CDR-H3 of SEQ ID NO: 3; and a light chain comprising CDR-L1 of SEQ ID NO: 4, CDR-L2 of SEQ ID NO: 5, and CDR-L3 of SEQ ID NO: 6;

(ii) a heavy chain variable region comprising CDR-H1 of SEQ ID NO: 10, CDR-H2 of SEQ ID NO: 11, and CDR-H3 of SEQ ID NO: 12; and a light chain variable region comprising CDR-L1 of SEQ ID NO: 13, CDR-L2 of SEQ ID NO: 14, and CDR-L3 of SEQ ID NO: 15;

(iii) a heavy chain variable region comprising CDR-H1 of SEQ ID NO: 19, CDR-H2 of SEQ ID NO: 20, and CDR-H3 of SEQ ID NO: 21; and a light chain variable region comprising CDR-L1 of SEQ ID NO: 22, CDR-L2 of SEQ ID NO: 23, and CDR-L3 of SEQ ID NO: 24;

(iv) a heavy chain variable region comprising CDR-H1 of SEQ ID NO: 28, CDR-H2 of SEQ ID NO: 29, and CDR-H3 of SEQ ID NO: 30; and a light chain variable region comprising CDR-L1 of SEQ ID NO: 31, CDR-L2 of SEQ ID NO: 32, and CDR-L3 of SEQ ID NO: 33; or (v) a heavy chain variable region comprising CDR-H1 of SEQ ID NO: 37, CDR-H2 of SEQ ID NO: 38, and CDR-H3 of SEQ ID NO: 39; and a light chain variable region comprising CDR-L1 of SEQ ID NO: 40, CDR-L2 of SEQ ID NO: 41, and CDR-L3 of SEQ ID NO: 42.

2. The antibody or antigen binding fragment thereof according to claim 1, wherein the antibody or antigen binding fragment thereof comprises:

(i) the heavy chain variable region of SEQ ID NO: 7 and the light chain variable region of SEQ ID NO: 8;

(ii) the heavy chain variable region of SEQ ID NO: 16 and the light chain variable region of SEQ ID NO: 17;

(iii) the heavy chain variable region of SEQ ID NO: 25 and the light chain variable region of SEQ ID NO: 26;

(iv) the heavy chain variable region of SEQ ID NO: 34 and the light chain variable region of SEQ ID NO: 35; or (v) the heavy chain variable region of SEQ ID NO: 43 and the light chain variable region of SEQ ID NO: 44.

3. The antibody or antigen binding fragment thereof according to claim 1, wherein the antibody or antigen binding fragment thereof comprises:

(i) the amino acid sequence of SEQ ID NO: 9;

(ii) the amino acid sequence of SEQ ID NO: 18;

(iii) the amino acid sequence of SEQ ID NO: 27;

(iv) the amino acid sequence of SEQ ID NO: 36; or (v) the amino acid sequence of SEQ ID NO: 45.

4. The antibody or antigen binding fragment thereof according to claim 1, wherein the SARS-CoV-2 S protein is a receptor binding domain (RBD), an S1 domain, or a full-length spike protein.

5. The antibody or antigen binding fragment thereof according to claim 1, wherein the antibody or the antigen binding fragment thereof is a monoclonal antibody, a polyclonal antibody, scFv, Fab, F(ab), F(ab)2, scFv-Fc, a minibody, a diabody, a triabody, a tetrabody, a bispecific antibody, a multispecific antibody, a human antibody, a humanized antibody, a chimeric antibody, or an antigen binding fragment thereof, each comprising the heavy chain variable region and the light chain variable region.

6. A nucleic acid molecule, comprising a nucleotide sequence coding for the antibody or antigen binding fragment thereof according to claim 1.

7. A recombinant vector carrying the nucleic acid molecule of claim 6.

8. An isolated host cell transformed with the recombinant vector of claim 7.

9. A pharmaceutical composition for prevention or treatment of SARS-CoV-2 infectious disease, the composition comprising the antibody or antigen binding fragment thereof specifically binding to SARS-CoV-2 S protein according to claim 1, and a pharmaceutically acceptable carrier.

10. A composition for detecting SARS-CoV-2 virus, comprising the antibody or the antigen binding fragment thereof specifically binding to SARS-CoV-2 S protein according to claim 1.

11. The composition of claim 10, wherein the composition comprises a pair of the following antibodies or antigen binding fragments thereof specifically binding to SARS-CoV-2 S protein:

(i) antibody or antigen binding fragment thereof comprising HCDR1 comprising the amino acid sequence of SEQ ID NO: 28, HCDR2 comprising the amino acid sequence of SEQ ID NO: 29, HCDR3 comprising the amino acid sequence of SEQ ID NO: 30, LCDR1 comprising the amino acid sequence of SEQ ID NO: 31, LCDR2 comprising the amino acid sequence of SEQ ID NO: 32, and LCDR3 comprising the amino acid sequence of SEQ ID NO: 33; and (ii) antibody or antigen binding fragment thereof comprising HCDR1 comprising the amino acid sequence of SEQ ID NO: 19, HCDR2 comprising the amino acid sequence of SEQ ID NO: 20, HCDR3 comprising the amino acid sequence of SEQ ID NO: 21, LCDR1 comprising the amino acid sequence of SEQ ID NO: 22, LCDR2 comprising the amino acid sequence of SEQ ID NO: 23, and LCDR3 comprising the amino acid sequence of SEQ ID NO: 24.

12. A kit for detecting SARS-CoV-2 virus, comprising the antibody or antigen binding fragment thereof according to claim 1.

13. The kit of claim 12, wherein the kit comprises a pair of the following antibodies or antigen binding fragments thereof specifically binding to SARS-CoV-2 S protein:

(i) antibody or antigen binding fragment thereof comprising HCDR1 comprising the amino acid sequence of SEQ ID NO: 28, HCDR2 comprising the amino acid sequence of SEQ ID NO: 29, HCDR3 comprising the amino acid sequence of SEQ ID NO: 30, LCDR1 comprising the amino acid sequence of SEQ ID NO: 31, LCDR2 comprising the amino acid sequence of SEQ ID NO: 32, and LCDR3 comprising the amino acid sequence of SEQ ID NO: 33; and (ii) antibody or antigen binding fragment thereof comprising HCDR1 comprising the amino acid sequence of SEQ ID NO: 19, HCDR2 comprising the amino acid sequence of SEQ ID NO: 20, HCDR3 comprising the amino acid sequence of SEQ ID NO: 21, LCDR1 comprising the amino acid sequence of SEQ ID NO: 22, LCDR2 comprising the amino acid sequence of SEQ ID NO: 23, and LCDR3 comprising the amino acid sequence of SEQ ID NO: 24.

14. The kit of claim 13, wherein the kit is a sandwich ELISA kit, and wherein one of the antibodies or antigen-binding fragments thereof of (i) and (ii) is used as a capture antibody and the other as a detection antibody.

15. The kit of claim 14, wherein the kit further comprises a signal-detecting antibody conjugated with a label binding to the detection antibody.

16. A bispecific antibody binding specifically to SARS-CoV-2, wherein the bispecific antibody comprises:

(a) an antibody or an antigen binding fragment thereof comprising a heavy chain variable region and a light chain variable region, the heavy chain variable region comprising heavy chain complementarity determining region 1 (HCDR1) having the amino acid sequence of SEQ ID NO: 28, H-CDR2 having the amino acid sequence of SEQ ID NO: 29, and H-CDR3 having the amino acid sequence of SEQ ID NO: 30; and the light chain variable comprising light chain comprising complementarity determining region 1 (L-CDR1) having the amino acid sequence of SEQ ID NO: 31, L-CDR2 having the amino acid sequence of SEQ ID NO: 32, and L-CDR3 having the amino acid sequence of SEQ ID NO: 33; and (b) an antibody or an antigen binding fragment thereof comprising a heavy chain variable region and a light chain variable region, the heavy chain variable region comprising HCDR1 having the amino acid sequence of SEQ ID NO: 19, H-CDR2 having the amino acid sequence of SEQ ID NO: 20, and H-CDR3 having the amino acid sequence of SEQ ID NO: 21; and the light chain variable comprising light chain comprising L-CDR1 having the amino acid sequence of SEQ ID NO: 22, L-CDR2 having the amino acid sequence of SEQ ID NO: 23, and L-CDR3 having the amino acid sequence of SEQ ID NO: 24.

17. The bispecific antibody of claim 16, wherein the heavy chain variable region of (a) comprises the amino acid sequence of SEQ ID NO: 7 and the light chain variable region of (a) comprises the amino acid sequence of SEQ ID NO: 8; and the heavy chain variable region of (b) comprises the amino acid sequence of SEQ ID NO: 17 and the light chain variable region of (b) comprises the amino acid sequence of SEQ ID NO: 18.

18. A pharmaceutical composition comprising the bispecific antibody of claim 16 and a pharmaceutically acceptable carrier for treating SARS-CoV-2 infectious disease.

19. The pharmaceutical composition of claim 18, wherein the SARS-CoV-2 is a variant having, on the amino acid sequence of RBD, a mutation selected from the group consisting of N354D/D364Y, V367F, W436R, R408I, G476S, V483A, V341I, F342L, A435S, and a combination thereof.

20. The pharmaceutical composition of claim 18, wherein the SARS-CoV-2 is selected from the group consisting of a wild type, an alpha variant, a beta variant, a gamma variant, a delta variant, and a kappa variant.

* * * * *

SEQUENCE LISTING

```
Sequence total quantity: 72
SEQ ID NO: 1            moltype = AA  length = 10
FEATURE                 Location/Qualifiers
source                  1..10
                        mol_type = protein
                        organism = synthetic construct
SEQUENCE: 1
GFTFSDYSMS                                                  10

SEQ ID NO: 2            moltype = AA  length = 17
FEATURE                 Location/Qualifiers
source                  1..17
                        mol_type = protein
                        organism = synthetic construct
SEQUENCE: 2
GIYHSDGSKY YADSVKG                                          17

SEQ ID NO: 3            moltype = AA  length = 7
FEATURE                 Location/Qualifiers
source                  1..7
                        mol_type = protein
                        organism = synthetic construct
SEQUENCE: 3
FDPVFDY                                                     7

SEQ ID NO: 4            moltype = AA  length = 13
FEATURE                 Location/Qualifiers
source                  1..13
                        mol_type = protein
                        organism = synthetic construct
SEQUENCE: 4
TGSSSNIGSN AVN                                              13

SEQ ID NO: 5            moltype = AA  length = 7
FEATURE                 Location/Qualifiers
```

-continued

```
source                 1..7
                       mol_type = protein
                       organism = synthetic construct
SEQUENCE: 5
ADSNRPS                                                     7

SEQ ID NO: 6           moltype = AA  length = 9
FEATURE                Location/Qualifiers
source                 1..9
                       mol_type = protein
                       organism = synthetic construct
SEQUENCE: 6
GAWDASLSA                                                   9

SEQ ID NO: 7           moltype = AA  length = 116
FEATURE                Location/Qualifiers
source                 1..116
                       mol_type = protein
                       organism = synthetic construct
SEQUENCE: 7
EVQLLESGGG LVQPGGSLRL SCAASGFTFS DYSMSWVRQA PGKGLEWVSG IYHSDGSKYY  60
ADSVKGRFTI SRDNSKNTLY LQMNSLRAED TAVYYCARFD PVFDYWGQGT LVTVSS      116

SEQ ID NO: 8           moltype = AA  length = 110
FEATURE                Location/Qualifiers
source                 1..110
                       mol_type = protein
                       organism = synthetic construct
SEQUENCE: 8
QSVLTQPPSA SGTPGQRVTI SCTGSSSNIG SNAVNWYQQL PGTAPKLLIY ADSNRPSGVP  60
DRFSGSKSGT SASLAISGLR SEDEADYYCG AWDASLSAYV FGGGTKLTVL             110

SEQ ID NO: 9           moltype = AA  length = 241
FEATURE                Location/Qualifiers
source                 1..241
                       mol_type = protein
                       organism = synthetic construct
SEQUENCE: 9
EVQLLESGGG LVQPGGSLRL SCAASGFTFS DYSMSWVRQA PGKGLEWVSG IYHSDGSKYY  60
ADSVKGRFTI SRDNSKNTLY LQMNSLRAED TAVYYCARFD PVFDYWGQGT LVTVSSGGGG  120
SGGGGSGGGG SQSVLTQPPS ASGTPGQRVT ISCTGSSSNI GSNAVNWYQQ LPGTAPKLLI  180
YADSNRPSGV PDRFSGSKSG TSASLAISGL RSEDEADYYC GAWDASLSAY VFGGGTKLTV  240
L                                                           241

SEQ ID NO: 10          moltype = AA  length = 10
FEATURE                Location/Qualifiers
source                 1..10
                       mol_type = protein
                       organism = synthetic construct
SEQUENCE: 10
GFTFSDYSMS                                                  10

SEQ ID NO: 11          moltype = AA  length = 17
FEATURE                Location/Qualifiers
source                 1..17
                       mol_type = protein
                       organism = synthetic construct
SEQUENCE: 11
GIYHSDGSKY YADSVKG                                          17

SEQ ID NO: 12          moltype = AA  length = 7
FEATURE                Location/Qualifiers
source                 1..7
                       mol_type = protein
                       organism = synthetic construct
SEQUENCE: 12
FDPVFDY                                                     7

SEQ ID NO: 13          moltype = AA  length = 13
FEATURE                Location/Qualifiers
source                 1..13
                       mol_type = protein
                       organism = synthetic construct
SEQUENCE: 13
SGSSSNIGSN AVS                                              13

SEQ ID NO: 14          moltype = AA  length = 7
FEATURE                Location/Qualifiers
source                 1..7
```

```
                        mol_type = protein
                        organism = synthetic construct
SEQUENCE: 14
DNNHRPS                                                       7

SEQ ID NO: 15           moltype = AA  length = 9
FEATURE                 Location/Qualifiers
source                  1..9
                        mol_type = protein
                        organism = synthetic construct
SEQUENCE: 15
GSWDDSLNA                                                     9

SEQ ID NO: 16           moltype = AA  length = 116
FEATURE                 Location/Qualifiers
source                  1..116
                        mol_type = protein
                        organism = synthetic construct
SEQUENCE: 16
EVQLLESGGG LVQPGGSLRL SCAASGFTFS DYSMSWVRQA PGKGLEWVSG IYHSDGSKYY  60
ADSVKGRFTI SRDNSKNTLY LQMNSLRAED TAVYYCARFD PVFDYWGQGT LVTVSS      116

SEQ ID NO: 17           moltype = AA  length = 110
FEATURE                 Location/Qualifiers
source                  1..110
                        mol_type = protein
                        organism = synthetic construct
SEQUENCE: 17
QSVLTQPPSA SGTPGQRVTI SCSGSSSNIG SNAVSWYQQL PGTAPKLLIY DNNHRPSGVP  60
DRFSGSKSGT SASLAISGLR SEDEADYYCG SWDDSLNAYV FGGGTKLTVL            110

SEQ ID NO: 18           moltype = AA  length = 241
FEATURE                 Location/Qualifiers
source                  1..241
                        mol_type = protein
                        organism = synthetic construct
SEQUENCE: 18
EVQLLESGGG LVQPGGSLRL SCAASGFTFS DYSMSWVRQA PGKGLEWVSG IYHSDGSKYY  60
ADSVKGRFTI SRDNSKNTLY LQMNSLRAED TAVYYCARFD PVFDYWGQGT LVTVSSGGGG  120
SGGGGSGGGG SQSVLTQPPS ASGTPGQRVT ISCSGSSSNI GSNAVSWYQQ LPGTAPKLLI  180
YDNNHRPSGV PDRFSGSKSG TSASLAISGL RSEDEADYYC GSWDDSLNAY VFGGGTKLTV  240
L                                                             241

SEQ ID NO: 19           moltype = AA  length = 10
FEATURE                 Location/Qualifiers
source                  1..10
                        mol_type = protein
                        organism = synthetic construct
SEQUENCE: 19
GFTFSSYDMS                                                    10

SEQ ID NO: 20           moltype = AA  length = 17
FEATURE                 Location/Qualifiers
source                  1..17
                        mol_type = protein
                        organism = synthetic construct
SEQUENCE: 20
GISYSGGSTY YADSVKG                                            17

SEQ ID NO: 21           moltype = AA  length = 12
FEATURE                 Location/Qualifiers
source                  1..12
                        mol_type = protein
                        organism = synthetic construct
SEQUENCE: 21
DVNFVPLVTF DY                                                 12

SEQ ID NO: 22           moltype = AA  length = 13
FEATURE                 Location/Qualifiers
source                  1..13
                        mol_type = protein
                        organism = synthetic construct
SEQUENCE: 22
TGSSSNIGSN SVT                                                13

SEQ ID NO: 23           moltype = AA  length = 7
FEATURE                 Location/Qualifiers
source                  1..7
                        mol_type = protein
```

```
                         organism = synthetic construct
SEQUENCE: 23
DDNQRPS                                                           7

SEQ ID NO: 24            moltype = AA  length = 9
FEATURE                  Location/Qualifiers
source                   1..9
                         mol_type = protein
                         organism = synthetic construct
SEQUENCE: 24
GTWDYSLSA                                                         9

SEQ ID NO: 25            moltype = AA  length = 121
FEATURE                  Location/Qualifiers
source                   1..121
                         mol_type = protein
                         organism = synthetic construct
SEQUENCE: 25
EVQLLESGGG LVQPGGSLRL SCAASGFTFS SYDMSWVRQA PGKGLEWVSG ISYSGGSTYY  60
ADSVKGRFTI SRDNSKNTLY LQMNSLRAED TAVYYCARDV NFVPLVTFDY WGQGTLVTVS  120
S                                                                 121

SEQ ID NO: 26            moltype = AA  length = 110
FEATURE                  Location/Qualifiers
source                   1..110
                         mol_type = protein
                         organism = synthetic construct
SEQUENCE: 26
QSVLTQPPSA SGTPGQRVTL SCTGSSSNIG SNSVTWYQQL PGTAPKLLIY DDNQRPSGVP  60
DRFSGSKSGT SASLAISGLR SEDEADYYCG TWDYSLSAYV FGGGTKLTVL            110

SEQ ID NO: 27            moltype = AA  length = 246
FEATURE                  Location/Qualifiers
source                   1..246
                         mol_type = protein
                         organism = synthetic construct
SEQUENCE: 27
EVQLLESGGG LVQPGGSLRL SCAASGFTFS SYDMSWVRQA PGKGLEWVSG ISYSGGSTYY  60
ADSVKGRFTI SRDNSKNTLY LQMNSLRAED TAVYYCARDV NFVPLVTFDY WGQGTLVTVS  120
SGGGGSGGGG SGGGGSQSVL TQPPSASGTP GQRVTLSCTG SSSNIGSNSV TWYQQLPGTA  180
PKLLIYDDNQ RPSGVPDRFS GSKSGTSASL AISGLRSEDE ADYYCGTWDY SLSAYVFGGG  240
TKLTVL                                                            246

SEQ ID NO: 28            moltype = AA  length = 10
FEATURE                  Location/Qualifiers
source                   1..10
                         mol_type = protein
                         organism = synthetic construct
SEQUENCE: 28
GFTFSDYAMS                                                        10

SEQ ID NO: 29            moltype = AA  length = 17
FEATURE                  Location/Qualifiers
source                   1..17
                         mol_type = protein
                         organism = synthetic construct
SEQUENCE: 29
WIYSGSGNKY YADSVKG                                                17

SEQ ID NO: 30            moltype = AA  length = 18
FEATURE                  Location/Qualifiers
source                   1..18
                         mol_type = protein
                         organism = synthetic construct
SEQUENCE: 30
FPIARTSNSQ SSYDGMDV                                               18

SEQ ID NO: 31            moltype = AA  length = 13
FEATURE                  Location/Qualifiers
source                   1..13
                         mol_type = protein
                         organism = synthetic construct
SEQUENCE: 31
SGSSSNIGSN AVS                                                    13

SEQ ID NO: 32            moltype = AA  length = 7
FEATURE                  Location/Qualifiers
source                   1..7
                         mol_type = protein
```

```
                      organism = synthetic construct
SEQUENCE: 32
ADNKRPS                                                        7

SEQ ID NO: 33         moltype = AA  length = 9
FEATURE               Location/Qualifiers
source                1..9
                      mol_type = protein
                      organism = synthetic construct
SEQUENCE: 33
GAWDSSLNA                                                      9

SEQ ID NO: 34         moltype = AA  length = 127
FEATURE               Location/Qualifiers
source                1..127
                      mol_type = protein
                      organism = synthetic construct
SEQUENCE: 34
EVQLLESGGG LVQPGGSLRL SCAASGFTFS DYAMSWVRQA PGKGLEWVSW IYSGSGNKYY  60
ADSVKGRFTI SRDNSKNTLY LQMNSLRAED TAVYYCARFP IARTSNSQSS YDGMDVWGQG  120
TLVTVSS                                                        127

SEQ ID NO: 35         moltype = AA  length = 110
FEATURE               Location/Qualifiers
source                1..110
                      mol_type = protein
                      organism = synthetic construct
SEQUENCE: 35
QSVLTQPPSA SGTPGQRVTI SCSGSSSNIG SNAVSWYQQL PGTAPKLLIY ADNKRPSGVP  60
DRFSGSKSGT SASLAISGLR SEDEADYYCG AWDSSLNAYV FGGGTKLTVL            110

SEQ ID NO: 36         moltype = AA  length = 252
FEATURE               Location/Qualifiers
source                1..252
                      mol_type = protein
                      organism = synthetic construct
SEQUENCE: 36
EVQLLESGGG LVQPGGSLRL SCAASGFTFS DYAMSWVRQA PGKGLEWVSW IYSGSGNKYY  60
ADSVKGRFTI SRDNSKNTLY LQMNSLRAED TAVYYCARFP IARTSNSQSS YDGMDVWGQG  120
TLVTVSSGGG GSGGGGSGGG GSQSVLTQPP SASGTPGQRV TISCSGSSSN IGSNAVSWYQ  180
QLPGTAPKLL IYADNKRPSG VPDRFSGSKS GTSASLAISG LRSEDEADYY CGAWDSSLNA  240
YVFGGGTKLT VL                                                  252

SEQ ID NO: 37         moltype = AA  length = 10
FEATURE               Location/Qualifiers
source                1..10
                      mol_type = protein
                      organism = synthetic construct
SEQUENCE: 37
GFTFSDYAMS                                                     10

SEQ ID NO: 38         moltype = AA  length = 17
FEATURE               Location/Qualifiers
source                1..17
                      mol_type = protein
                      organism = synthetic construct
SEQUENCE: 38
AIYPGGGSTY YADSVKG                                             17

SEQ ID NO: 39         moltype = AA  length = 7
FEATURE               Location/Qualifiers
source                1..7
                      mol_type = protein
                      organism = synthetic construct
SEQUENCE: 39
NLFGFDY                                                        7

SEQ ID NO: 40         moltype = AA  length = 13
FEATURE               Location/Qualifiers
source                1..13
                      mol_type = protein
                      organism = synthetic construct
SEQUENCE: 40
TGSSSNIGSN AVY                                                 13

SEQ ID NO: 41         moltype = AA  length = 7
FEATURE               Location/Qualifiers
source                1..7
                      mol_type = protein
```

```
                          organism = synthetic construct
SEQUENCE: 41
DDSNRPS                                                                   7

SEQ ID NO: 42             moltype = AA  length = 9
FEATURE                   Location/Qualifiers
source                    1..9
                          mol_type = protein
                          organism = synthetic construct
SEQUENCE: 42
GSWDDSLSA                                                                 9

SEQ ID NO: 43             moltype = AA  length = 116
FEATURE                   Location/Qualifiers
source                    1..116
                          mol_type = protein
                          organism = synthetic construct
SEQUENCE: 43
EVQLLESGGG LVQPGGSLRL SCAASGFTFS DYAMSWVRQA PGKGLEWVSA IYPGGGSTYY  60
ADSVKGRFTI SRDNSKNTLY LQMNSLRAED TAVYYCARNL FGFDYWGQGT LVTVSS      116

SEQ ID NO: 44             moltype = AA  length = 110
FEATURE                   Location/Qualifiers
source                    1..110
                          mol_type = protein
                          organism = synthetic construct
SEQUENCE: 44
QSVLTQPPSA SGTPGQRVTI SCTGSSSNIG SNAVYWYQQL PGTAPKLLIY DDSNRPSGVP  60
DRFSGSKSGT SASLAISGLR SEDEADYYCG SWDDSLSAYV FGGGTKLTVL             110

SEQ ID NO: 45             moltype = AA  length = 241
FEATURE                   Location/Qualifiers
source                    1..241
                          mol_type = protein
                          organism = synthetic construct
SEQUENCE: 45
EVQLLESGGG LVQPGGSLRL SCAASGFTFS DYAMSWVRQA PGKGLEWVSA IYPGGGSTYY  60
ADSVKGRFTI SRDNSKNTLY LQMNSLRAED TAVYYCARNL FGFDYWGQGT LVTVSSGGGG  120
SGGGGSGGGG SQSVLTQPPS ASGTPGQRVT ISCTGSSSNI GSNAVYWYQQ LPGTAPKLLI  180
YDDSNRPSGV PDRFSGSKSG TSASLAISGL RSEDEADYYC GSWDDSLSAY VFGGGTKLTV  240
L                                                                  241

SEQ ID NO: 46             moltype = DNA  length = 723
FEATURE                   Location/Qualifiers
source                    1..723
                          mol_type = other DNA
                          organism = synthetic construct
SEQUENCE: 46
gaggtgcagc tgttggagtc tgggggaggc ttggtacagc ctggggggtc cctgagactc  60
tcctgtgcag cctctggatt cacctttagc gattattcta tgagctgggt ccgccaggct  120
ccagggaagg ggctggagtg ggtctcaggg atctatcata gtgatggtag taaatattac  180
gctgattctg taaaaggtcg gttcaccatc tccagagaca attccaagaa cacgctgtat  240
ctgcaaatga acagcctgag agccgaggac acggccgtgt attactgtgc gagatttgat  300
cctgttttcg actactgggg ccagggtaca ctggtcaccg tgagctcagg tggaggcggt  360
tcaggcggag gtggatccgg cggtggcgga tcgcagtctg tgctgactca gccaccctca  420
gcgtctggga cccccgggca gagggtcacc atctcttgta ctggctcttc atctaatatt  480
ggcagtaatg ctgtcaactg gtaccagcag ctcccaggaa cggcccccaa actcctcatc  540
tatgctgata gtaatcggcc aagcggggtc cctgaccgat tctctggctc caagtctggc  600
acctcagcct ccctggccat cagtgggctc cggtccgagg atgaggctga ttattactgt  660
ggtgcttggg atgctagcct gagtgcttat gtcttcggcg gaggcaccaa gctgacggtc  720
cta                                                                723

SEQ ID NO: 47             moltype = DNA  length = 723
FEATURE                   Location/Qualifiers
source                    1..723
                          mol_type = other DNA
                          organism = synthetic construct
SEQUENCE: 47
gaggtgcagc tgttggagtc tgggggaggc ttggtacagc ctggggggtc cctgagactc  60
tcctgtgcag cctctggatt cacctttagc gattattcta tgagctgggt ccgccaggct  120
ccagggaagg ggctggagtg ggtctcaggg atctatcata gtgatggtag taaatattac  180
gctgattctg taaaaggtcg gttcaccatc tccagagaca attccaagaa cacgctgtat  240
ctgcaaatga acagcctgag agccgaggac acggccgtgt attactgtgc gagatttgat  300
cctgttttcg actactgggg ccagggtaca ctggtcaccg tgagctcagg tggaggcggt  360
tcaggcggag gtggatccgg cggtggcgga tcgcagtctg tgctgactca gccaccctca  420
gcgtctggga cccccgggca gagggtcacc atctcttgta gtggctcttc atctaatatt  480
ggcagtaatg ctgtctcctg gtaccagcag ctcccaggaa cggcccccaa actcctcatc  540
tatgataata atcatcggcc aagcggggtc cctgaccgat tctctggctc caagtctggc  600
acctcagcct ccctggccat cagtgggctc cggtccgagg atgaggctga ttattactgt  660
```

```
ggttcttggg atgatagcct gaatgcttat gtcttcggcg gaggcaccaa gctgacggtc  720
cta                                                                723

SEQ ID NO: 48          moltype = DNA  length = 738
FEATURE                Location/Qualifiers
source                 1..738
                       mol_type = other DNA
                       organism = synthetic construct
SEQUENCE: 48
gaggtgcagc tgttggagtc tgggggaggc ttggtacagc ctggggggtc cctgagactc  60
tcctgtgcag cctctggatt cacctttagc agttatgata tgagctgggt ccgccaggct  120
ccagggaagg ggctggagtg ggtctcaggg atctcttata gtggtggtag tacatattac  180
gctgattctg taaaaggtcg gttcaccatc tccagagaca attccaagaa cacgctgtat  240
ctgcaaatga acagcctgag agccgaggac acggccgtgt attactgtgc gagagatgtt  300
aattttgttc cgttggttac gttcgactac tggggccagg gtacactggt caccgtgagc  360
tcaggtggag gcggttcagg cggaggtgga tccggcggtg gcggatcgca gtctgtgctg  420
actcagccac cctcagcgtc tgggaccccc gggcagaggg tcaccctctc ttgtactggc  480
tcttcatcta atattggcag taattctgtc acctggtacc agcagctccc aggaacggcc  540
cccaaactcc tcatctatga tgataatcag cggccgagcg gggtccctga ccgattctct  600
ggctccaagt ctggcacctc agcctccctg gccatcagtg ggctccggtc cgaggatgag  660
gctgattatt actgtggtac ttgggattat agcctgagtg cttatgtctt cggcggaggc  720
accaagctga cggtccta                                                738

SEQ ID NO: 49          moltype = DNA  length = 756
FEATURE                Location/Qualifiers
source                 1..756
                       mol_type = other DNA
                       organism = synthetic construct
SEQUENCE: 49
gaggtgcagc tgttggagtc tgggggaggc ttggtacagc ctggggggtc cctgagactc  60
tcctgtgcag cctctggatt cacctttagc gattatgcta tgagctgggt ccgccaggct  120
ccagggaaag ggctggagtg ggtctcatgg atctattctg gtagtggtaa taaatattac  180
gctgattctg taaaaggtcg gttcaccatc tccagagaca attccaagaa cacgctgtat  240
ctgcaaatga acagcctgag agccgaggac acggccgtgt attactgtgc gagatttcct  300
attgctcgta cttctaatag tcagtcttct tatgatggta tggacgtctg gggccagggt  360
acactggtca ccgtgagctc aggtggaggc ggttcaggcg gaggtggatc cggcggtggc  420
ggatcgcagt ctgtgctgac tcagccaccc tcagcgtctg ggacccccgg gcagagggtc  480
accatctctt gtagtggctc ttcatctaat attggcagta atgctgtctc ctggtaccag  540
cagctcccag gaacggcccc caaactcctc atctatgctg ataataagcg gccaagcggg  600
gtccctgacc gattctctgg ctccaagtct ggcacctcag cctccctggc catcagtggg  660
ctccggtccg aggatgaggc tgattattac tgtggtgctt gggattctag cctgaatgct  720
tatgtcttcg gcggaggcac caagctgacg gtccta                            756

SEQ ID NO: 50          moltype = DNA  length = 723
FEATURE                Location/Qualifiers
source                 1..723
                       mol_type = other DNA
                       organism = synthetic construct
SEQUENCE: 50
gaggtgcagc tgttggagtc tgggggaggc ttggtacagc ctggggggtc cctgagactc  60
tcctgtgcag cctctggatt cacctttagc gattatgcta tgagctgggt ccgccaggct  120
ccagggaagg ggctggagtg ggtctcagcg atctatcctg gtggtggtag tacatattac  180
gctgattctg taaaaggtcg gttcaccatc tccagagaca attccaagaa cacgctgtat  240
ctgcaaatga acagcctgag agccgaggac acggccgtgt attactgtgc gagaaatctg  300
tttgggttcg actactgggg ccagggtaca ctggtcaccg tgagctcagg tggaggcggt  360
tcaggcggag gtggatccgg cggtggcgga tcgcagtctg tgctgactca gccaccctca  420
gcgtctggga cccccgggca gagggtcacc atctcttgta ctggctcttc atctaatatt  480
ggcagtaatg ctgtctactg gtaccagcag ctcccaggaa cggcccccaa actcctcatc  540
tatgatgata gtaatcggcc aagcggggtc cctgaccgat tctctggctc caagtctggc  600
acctcagcct ccctggccat cagtgggctc cggtccgagg atgaggctga ttattactgt  660
ggttcttggg atgatagcct gagtgcttat gtcttcggcg gaggcaccaa gctgacggtc  720
cta                                                                723

SEQ ID NO: 51          moltype = AA  length = 157
FEATURE                Location/Qualifiers
source                 1..157
                       mol_type = protein
                       organism = synthetic construct
SEQUENCE: 51
RVTSVRNTNC GVNATRASVY AWNRKRSNCV ADYSVYNSAS STKCYGVSTK NDCTNVYADS  60
VRGDVRAGTG KADYNYKDDT GCVAWNSNND SKVGGNYNYY RRKSNKRDST YAGSTCNGVG  120
NCYSYGTNGV GYYRVVVSHA ATVCGKKSTN VKNKCVN                            157

SEQ ID NO: 52          moltype = AA  length = 458
FEATURE                Location/Qualifiers
source                 1..458
                       mol_type = protein
                       organism = synthetic construct
SEQUENCE: 52
```

```
SCVNTTRTAY TNSTRGVYYD KVRSSVHSTD SNVTWHAHVS GTNGTKRDNV NDGVYASTKS  60
NRGWGTTDSK TSVNNATNVV KVCCNDGVYY HKNNKSWMSR VYSSANNCTY VSMDGKGNKN  120
RVKNDGYKYS KHTNVRDGSA VDGNTRTAHR SYTGDSSSGW TAGAAAYYVG YRTKYNNGTT  180
DAVDCADSTK CTKSTVKGYT SNRVTSVRNT NCGVNATRAS VYAWNRKRSN CVADYSVYNS  240
ASSTKCYGVS TKNDCTNVYA DSVRGDVRAG TGKADYNYKD DTGCVAWNSN NDSKVGGNYN  300
YYRRKSNKRD STYAGSTCNG VGNCYSYGTN GVGYYRVVVS HAATVCGKKS TNVKNKCVNN  360
NGTGTGVTSN KKGRDADTTD AVRDTDTCSG GVSVTGTNTS NVAVYDVNCT VVAHADTTWR  420
VYSTGSNVTR AGCGAHVNNS YCDGAGCASY TTNSRRAR                         458

SEQ ID NO: 53          moltype = AA  length = 381
FEATURE                Location/Qualifiers
source                 1..381
                       mol_type = protein
                       organism = synthetic construct
SEQUENCE: 53
SVASSAYTMS GANSVAYSNN SATNTSVTTV SMTKTSVDCT MYCGDSTCSN YGSCTNRATG  60
AVDKNTVAVK YKTKDGGNSD SKSKRSDNKV TADAGKYGDC GDAARDCAKN GTVTDMAYTS  120
AAGTTSGWTG AGAAAMMAYR NGGVTNVYNK ANNSAGKDSS STASAGKDVV NNAANTVKSS  180
NGASSVNDSR DKVAVDRTGR STYVTRAARA SANAATKMSC VGSKRVDCGK GYHMSSAHGV  240
VHVTYVAKNT TAACHDGKAH RGVVSNGTHW VTRNYTTDNT VSGNCDVVGV NNTVYDDSKD  300
KYKNHTSDVD GDSGNASVVN KDRNVAKNNS DGKYYKWWYW GAGAVMVTMC CMTSCCSCKG  360
CCSCGSCCKD DDSVKGVKHY T                                            381

SEQ ID NO: 54          moltype = AA  length = 844
FEATURE                Location/Qualifiers
source                 1..844
                       mol_type = protein
                       organism = synthetic construct
SEQUENCE: 54
MVVVSSCVNT TRTAYTNSTR GVYYDKVRSS VHSTDSNVTW HAHVSGTNGT KRDNVNDGVY  60
ASTKSNRGWG TTDSKTSVNN ATNVVKVCCN DGVYYHKNNK SWMSRVYSSA NNCTYVSMDG  120
KGNKNRVKND GYKYSKHTNV RDGSAVDGNT RTAHRSYTGD SSSGWTAGAA AYYVGYRTKY  180
NNGTTDAVDC ADSTKCTKST VKGYTSNRVT SVRNTNCGVN ATRASVYAWN RKRSNCVADY  240
SVYNSASSTK CYGVSTKNDC TNVYADSVRG DVRAGTGKAD YNYKDDTGCV AWNSNNDSKV  300
GGNYNYYRRK SNKRDSTYAG STCNGVGNCY SYGTNGVGYY RVVVSHAATV CGKKSTNVKN  360
KCVNNNGTGT GVTSNKKGRD ADTTDAVRDT DTCSGGVSVT GTNTSNVAVY DVNCTVVAHA  420
DTTWRVYSTG SNVTRAGCGA HVNNSYCDGA GCASYTTNSR RARSVASSAY TMSGANSVAY  480
SNNSATNTSV TTVSMTKTSV DCTMYCGDST CSNYGSCTNR ATGAVDKNTV AVKYKTKDGG  540
NSDSKSKRSD NKVTADAGKY GDCGDAARDC AKNGTVTDMA YTSAAGTTSG WTGAGAAAMM  600
AYRNGGVTNV YNKANNSAGK DSSSTASAGK DVVNNAANTV KSSNGASSVN DSRDKVAVDR  660
TGRSTYVTRA ARASANAATK MSCVGSKRVD CGKGYHMSSA HGVVHVTYVA KNTTAACHDG  720
KAHRGVVSNG THWVTRNYTT DNTVSGNCDV VGVNNTVYDD SKDKYKNHTS DVDGDSGNAS  780
VVNKDRNVAK NNSDGKYYKW WYWGAGAVMV TMCCMTSCCS CKGCCSCGSC CKDDDSVKGV  840
KHYT                                                               844

SEQ ID NO: 55          moltype = AA  length = 222
FEATURE                Location/Qualifiers
source                 1..222
                       mol_type = protein
                       organism = synthetic construct
SEQUENCE: 55
RVVPSGDVVR FPNITNLCPF GEVFNATKFP SVYAWERKKI SNCVADYSVL YNSTFFSTFK  60
CYGVSATKLN DLCFSNVYAD SFVVKGDDVR QIAPGQTGVI ADYNYKLPDD FMGCVLAWNT  120
RNIDATSTGN YNYKYRYLRH GKLRPFERDI SNVPFSPDGK PCTPPALNCY WPLNDYGFYT  180
TTGIGYQPYR VVVLSFELLN APATVCGPKL STDLIKNQCV NF                     222

SEQ ID NO: 56          moltype = AA  length = 223
FEATURE                Location/Qualifiers
source                 1..223
                       mol_type = protein
                       organism = synthetic construct
SEQUENCE: 56
RVQPTESIVR FPNITNLCPF GEVFNATRFA SVYAWNRKRI SNCVADYSVL YNSASFSTFK  60
CYGVSPTKLN DLCFTNVYAD SFVIRGDEVR QIAPGQTGKI ADYNYKLPDD FTGCVIAWNS  120
NNLDSKVGGN YNYLYRLFRK SNLKPFERDI STEIYQAGST PCNGVEGFNC YFPLQSYGFQ  180
PTNGVGYQPY RVVVLSFELL HAPATVCGPK KSTNLVKNKC VNF                    223

SEQ ID NO: 57          moltype = AA  length = 223
FEATURE                Location/Qualifiers
source                 1..223
                       mol_type = protein
                       organism = synthetic construct
SEQUENCE: 57
RVQPTESIVR FPNITNLCPF GEVFNATRFA SVYAWNRKRI SNCVADYSVL YNSASFSTFK  60
CYGVSPTKLN DLCFTNVYAD SFVIRGDEVR QIAPGQTGKI ADYNYKLPDD FTGCVISWNS  120
NNLDSKVGGN YNYLYRLFRK SNLKPFERDI STEIYQAGST PCNGVEGFNC YFPLQSYGFQ  180
PTNGVGYQPY RVVVLSFELL HAPATVCGPK KSTNLVKNKC VNF                    223

SEQ ID NO: 58          moltype = AA  length = 223
```

```
FEATURE                 Location/Qualifiers
source                  1..223
                        mol_type = protein
                        organism = synthetic construct
SEQUENCE: 58
RVQPTESIVR FPNITNLCPF GEVFNATRFA SVYAWDRKRI SNCVADYSVL YNSASFSTFK  60
CYGVSPTKLN DLCFTNVYAD SFVIRGDEVR QIAPGQTGKI ADYNYKLPDD FTGCVIAWNS  120
NNLDSKVGGN YNYLYRLFRK SNLKPFERDI STEIYQAGST PCNGVEGFNC YFPLQSYGFQ  180
PTNGVGYQPY RVVVLSFELL HAPATVCGPK KSTNLVKNKC VNF                    223

SEQ ID NO: 59           moltype = AA  length = 223
FEATURE                 Location/Qualifiers
source                  1..223
                        mol_type = protein
                        organism = synthetic construct
SEQUENCE: 59
RVQPTESIVR FPNITNLCPF GEVFNATRFA SVYAWNRKRI SNCVADYSVL YNSASFSTFK  60
CYGVSPTKLN DLCFTNVYAD SFVIRGDEVR QIAPGQTGKI ADYNYKLPDD FTGCVIAWNS  120
NNLDSKVGGN YNYLYRLFRK SNLKPFERDI STEIYQASST PCNGVEGFNC YFPLQSYGFQ  180
PTNGVGYQPY RVVVLSFELL HAPATVCGPK KSTNLVKNKC VNF                    223

SEQ ID NO: 60           moltype = AA  length = 223
FEATURE                 Location/Qualifiers
source                  1..223
                        mol_type = protein
                        organism = synthetic construct
SEQUENCE: 60
RVQPTESIVR FPNITNLCPF GEVFNATRFA SVYAWNRKRI SNCVADYSVL YNSASFSTFK  60
CYGVSPTKLN DLCFTNVYAD SFVIRGDEVR QIAPGQTGKI ADYNYKLPDD FTGCVIAWNS  120
NNLDSKVGGN YNYLYRLFRK SNLKPFERDI STEIYQAGST PCNGAEGFNC YFPLQSYGFQ  180
PTNGVGYQPY RVVVLSFELL HAPATVCGPK KSTNLVKNKC VNF                    223

SEQ ID NO: 61           moltype = AA  length = 223
FEATURE                 Location/Qualifiers
source                  1..223
                        mol_type = protein
                        organism = synthetic construct
SEQUENCE: 61
RVQPTESIVR FPNITNLCPF GEVLNATRFA SVYAWNRKRI SNCVADYSVL YNSASFSTFK  60
CYGVSPTKLN DLCFTNVYAD SFVIRGDEVR QIAPGQTGKI ADYNYKLPDD FTGCVIAWNS  120
NNLDSKVGGN YNYLYRLFRK SNLKPFERDI STEIYQAGST PCNGVEGFNC YFPLQSYGFQ  180
PTNGVGYQPY RVVVLSFELL HAPATVCGPK KSTNLVKNKC VNF                    223

SEQ ID NO: 62           moltype = AA  length = 223
FEATURE                 Location/Qualifiers
source                  1..223
                        mol_type = protein
                        organism = synthetic construct
SEQUENCE: 62
RVQPTESIVR FPNITNLCPF GEIFNATRFA SVYAWNRKRI SNCVADYSVL YNSASFSTFK  60
CYGVSPTKLN DLCFTNVYAD SFVIRGDEVR QIAPGQTGKI ADYNYKLPDD FTGCVIAWNS  120
NNLDSKVGGN YNYLYRLFRK SNLKPFERDI STEIYQAGST PCNGVEGFNC YFPLQSYGFQ  180
PTNGVGYQPY RVVVLSFELL HAPATVCGPK KSTNLVKNKC VNF                    223

SEQ ID NO: 63           moltype = AA  length = 223
FEATURE                 Location/Qualifiers
source                  1..223
                        mol_type = protein
                        organism = synthetic construct
SEQUENCE: 63
RVQPTESIVR FPNITNLCPF GEVFNATRFA SVYAWNRKRI SNCVADYSVL YNSASFSTFK  60
CYGVSPTKLN DLCFTNVYAD SFVIRGDEVR QIAPGQTGKI ADYNYKLPDD FTGCVIAWNS  120
NNLDSKVGGN YNYLYRLFRK SNLKPFERDI STEIYQAGST PCNGVEGFNC YFPLQSYGFQ  180
PTYGVGYQPY RVVVLSFELL HAPATVCGPK KSTNLVKNKC VNF                    223

SEQ ID NO: 64           moltype = AA  length = 223
FEATURE                 Location/Qualifiers
source                  1..223
                        mol_type = protein
                        organism = synthetic construct
SEQUENCE: 64
RVQPTESIVR FPNITNLCPF GEVFNATRFA SVYAWNRKRI SNCVADYSVL YNSASFSTFK  60
CYGVSPTKLN DLCFTNVYAD SFVIRGDEVR QIAPGQTGKI ADYNYKLPDD FTGCVIAWNS  120
NNLDSKVGGN YNYRYRLFRK SNLKPFERDI STEIYQAGSK PCNGVEGFNC YFPLQSYGFQ  180
PTNGVGYQPY RVVVLSFELL HAPATVCGPK KSTNLVKNKC VNF                    223

SEQ ID NO: 65           moltype = AA  length = 451
FEATURE                 Location/Qualifiers
source                  1..451
```

```
                        mol_type = protein
                        organism = synthetic construct
SEQUENCE: 65
EVQLLESGGG LVQPGGSLRL SCAASGFTFS DYAMSWVRQA PGKGLEWVSW IYSGSGNKYY  60
ADSVKGRFTI SRDNSKNTLY LQMNSLRAED TAVYYCARFP IARTSNSQSS YDGMDVWGQG  120
TLVTVSSAST KGPSVFPLAP CSRSTSESTA ALGCLVKDYF PEPVTVSWNS GALTSGVHTF  180
PAVLQSSGLY SLSSVVTVPS SSLGTKTYTC NVDHKPSNTK VDKRVESKYG PPCPPCPPCP  240
APEFLGGPSV FLFPPKPKDT LMISRTPEVT CVVVDVSQED PEVQFNWYVD GVEVHNAKTK  300
PREEQFNSTY RVVSVLTVLH QDWLNGKEYK CKVSNKGLPS SIEKGQPREP QVYTLPPSQE  360
EMTKNQVSLT CLVKGFYPSD IAVEWESNGQ PENNYKTTPP VLDSDGSFFL YSRLTVDKSR  420
WQEGNVFSCS VMHEALHNHY TQKSLSLSLG K                                451

SEQ ID NO: 66           moltype = AA  length = 215
FEATURE                 Location/Qualifiers
source                  1..215
                        mol_type = protein
                        organism = synthetic construct
SEQUENCE: 66
QSVLTQPPSA SGTPGQRVTI SCSGSSSNIG SNAVSWYQQL PGTAPKLLIY ADNKRPSGVP  60
DRFSGSKSGT SASLAISGLR SEDEADYYCG AWDSSLNAYV FGGGTKLTVL VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                            215

SEQ ID NO: 67           moltype = DNA  length = 26
FEATURE                 Location/Qualifiers
source                  1..26
                        mol_type = other DNA
                        organism = synthetic construct
SEQUENCE: 67
acaggtacgt taatagttaa tagcgt                                      26

SEQ ID NO: 68           moltype = DNA  length = 22
FEATURE                 Location/Qualifiers
source                  1..22
                        mol_type = other DNA
                        organism = synthetic construct
SEQUENCE: 68
atattgcagc agtacgcaca ca                                          22

SEQ ID NO: 69           moltype = DNA  length = 26
FEATURE                 Location/Qualifiers
source                  1..26
                        mol_type = other DNA
                        organism = synthetic construct
SEQUENCE: 69
acactagcca tccttactgc gcttcg                                      26

SEQ ID NO: 70           moltype = DNA  length = 18
FEATURE                 Location/Qualifiers
source                  1..18
                        mol_type = other DNA
                        organism = synthetic construct
SEQUENCE: 70
atgagcttag tcctgttg                                               18

SEQ ID NO: 71           moltype = DNA  length = 18
FEATURE                 Location/Qualifiers
source                  1..18
                        mol_type = other DNA
                        organism = synthetic construct
SEQUENCE: 71
ctccctttgt tgtgttgt                                               18

SEQ ID NO: 72           moltype = DNA  length = 22
FEATURE                 Location/Qualifiers
source                  1..22
                        mol_type = other DNA
                        organism = synthetic construct
SEQUENCE: 72
agattgtctt gtgctgccgg ta                                          22
```